(12) United States Patent
Kim et al.

(10) Patent No.: US 11,033,571 B2
(45) Date of Patent: Jun. 15, 2021

(54) PHARMACEUTICAL COMPOSITION FOR PREVENTING OR TREATING HEPATITIS B

(71) Applicant: AM SCIENCES INC, Seoul (KR)

(72) Inventors: Kyun Hwan Kim, Seoul (KR); Doo Hyun Kim, Seoul (KR); Yeong Min Park, Seoul (KR)

(73) Assignee: AM SCIENCES INC, Seoul (KR)

( * ) Notice: Subject to any disclaimer, the term of this patent is extended or adjusted under 35 U.S.C. 154(b) by 39 days.

(21) Appl. No.: 16/469,488

(22) PCT Filed: Dec. 13, 2017

(86) PCT No.: PCT/KR2017/014662
§ 371 (c)(1),
(2) Date: Jun. 13, 2019

(87) PCT Pub. No.: WO2018/110980
PCT Pub. Date: Jun. 21, 2018

(65) Prior Publication Data
US 2019/0343864 A1 Nov. 14, 2019

(30) Foreign Application Priority Data
Dec. 13, 2016 (KR) .................... 10-2016-0169681

(51) Int. Cl.
*A61K 31/713* (2006.01)
*A61P 31/20* (2006.01)
*A61K 9/51* (2006.01)

(52) U.S. Cl.
CPC .......... *A61K 31/713* (2013.01); *A61K 9/5161* (2013.01); *A61P 31/20* (2018.01)

(58) Field of Classification Search
None
See application file for complete search history.

(56) References Cited

U.S. PATENT DOCUMENTS

| 8,642,752 | B2 * | 2/2014 | Swayze | A61P 1/16 536/24.5 |
| 2003/0206887 | A1 | 11/2003 | Morrissey et al. | |
| 2004/0127446 | A1 * | 7/2004 | Blatt | C07H 21/00 514/44 R |
| 2013/0288380 | A1 | 10/2013 | Miyoshi | |
| 2015/0176007 | A1 * | 6/2015 | Prakash | C07H 21/04 536/17.1 |
| 2015/0265672 | A1 | 9/2015 | Guo et al. | |
| 2016/0040166 | A1 | 2/2016 | Tonelli et al. | |
| 2016/0235863 | A1 * | 8/2016 | Gao | C08B 37/003 |

FOREIGN PATENT DOCUMENTS

| CN | 1580070 A | * | 2/2005 |
| JP | 2014-513954 A | | 6/2014 |
| KR | 10-2011-0127086 A | | 11/2011 |
| KR | 10-2014-0130514 A | | 11/2014 |
| KR | 10-2015-0022911 A | | 3/2015 |
| WO | WO-2012/084993 A2 | | 6/2012 |
| WO | WO-2012/145697 A1 | | 10/2012 |

OTHER PUBLICATIONS

Machine translation of CN-1580070 specification and claims, 7 pages.*
Cai et al., "Identification of disubstituted sulfonamide compounds as specific inhibitors of hepatitis B virus covalently closed circular DNA formation," Antimicrob Agents Chemother. 56(8):4277-88 (2012).
Harris et al., "G-quadruplexes in pathogens: a common route to virulence control?" PLoS Pathog. 11(2):e1004562 (2015) (15 pages).
International Search Report dated Mar. 19, 2018 for International Patent Application No. PCT/KR2017/014662, Kim et al., "Pharmaceutical Composition for Preventing or Treating Hepatitis B," filed Dec. 13, 2017 (10 pages).
Jenkins et al., NCBI, GenBank Accession No. KY003230.1 dated Nov. 26, 2016, retrieved on Jun. 12, 2019 (3 pages).
Métifiot et al., "G-quadruplexes in viruses: function and potential therapeutic applications," Nucleic Acids Res. 42(20):12352-66 (2014).
Pollicino et al., "Hepatitis B virus replication is regulated by the acetylation status of hepatitis B virus cccDNA-bound H3 and H4 histones," Gastroenterology. 130(3):823-37 (2006).
Urban et al., "The replication cycle of hepatitis B virus," J Hepatol. 52(2):282-4 (2010).
Examination Report dated Jun. 19, 2020 for Canadian Patent Application No. 3,047,076, Kim et al., "Pharmaceutical Composition for Preventing or Treating Hepatitis B," filed Dec. 13, 2017 (7 pages).
Examination Report No. 1 dated May 15, 2020 for Australian Patent Application No. 2017375819, Kim et al., "Pharmaceutical composition for preventing or treating hepatitis B," filed Dec. 13, 2017 (8 pages).
Extended European Search Report dated Jul. 7, 2020 for European Patent Application No. 17881424.0, Kim et al., "Pharmaceutical composition for preventing or treating hepatitis B," filed Dec. 13, 2017 (10 pages).

* cited by examiner

*Primary Examiner* — Tracy Vivlemore
(74) *Attorney, Agent, or Firm* — Clark & Elbing LLP; Susan M. Michaud

(57) ABSTRACT

The present invention relates to a pharmaceutical composition for treating or preventing hepatitis B, comprising: at least one oligonucleotide selected from the group consisting an oligonucleotide represented by a nucleic acid sequence of SEQ ID NO: 1, 2, or 6 or a nucleic acid sequence complementary thereto; and an oligonucleotide having at least one chemical modification on the oligonucleotide, as an active ingredient, and a method for screening a therapeutic agent for hepatitis B according to the formation of a G-quadruplex by HBV and a candidate material. The pharmaceutical composition forms a G-quadruplex with HBV and reduces cccDNA (covalently closed circular DNA) and thus can be used in the treatment or prevention of hepatitis B.

19 Claims, 34 Drawing Sheets

Specification includes a Sequence Listing.

FIG. 12C
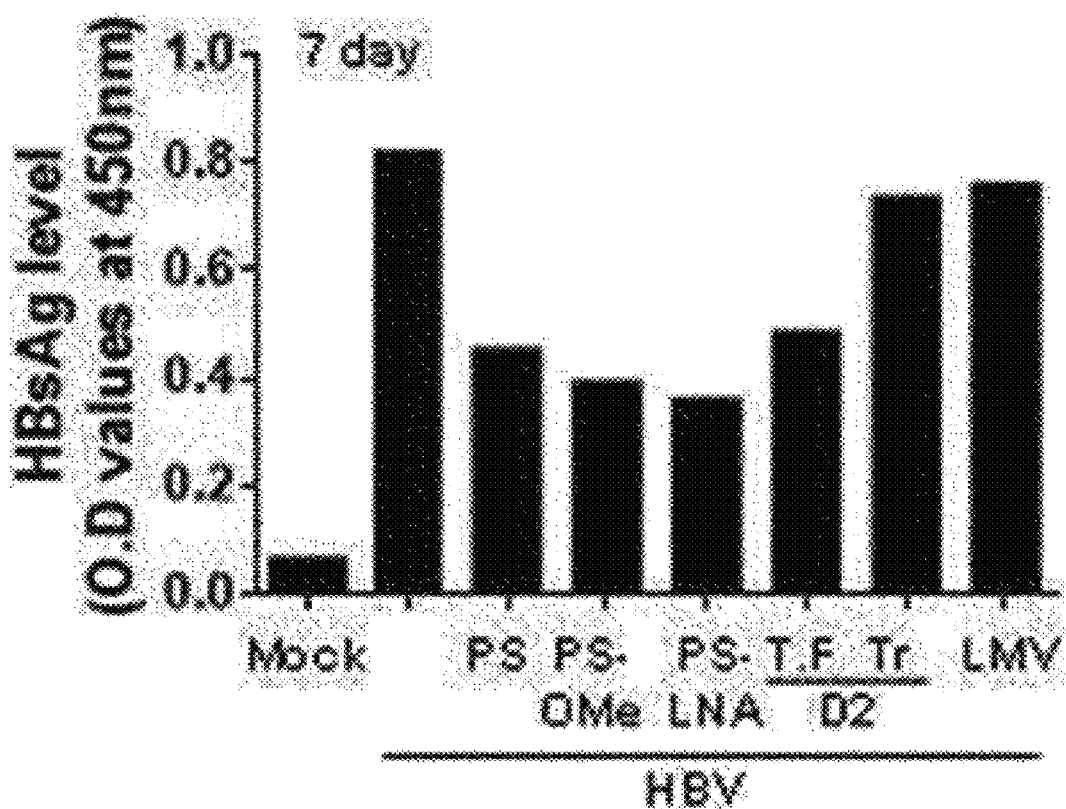
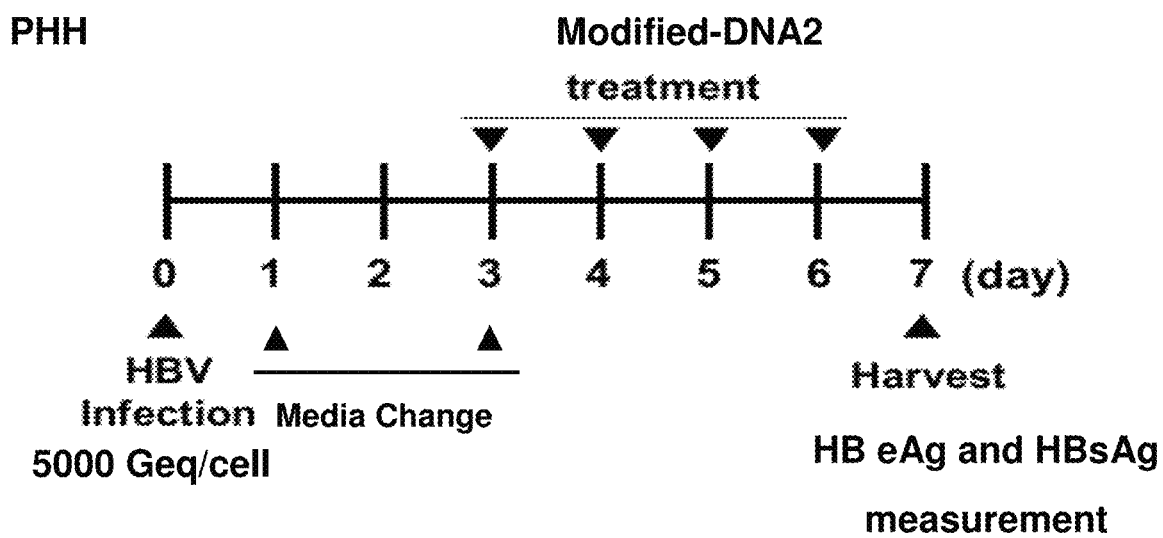
FIG. 13A

FIG. 13B
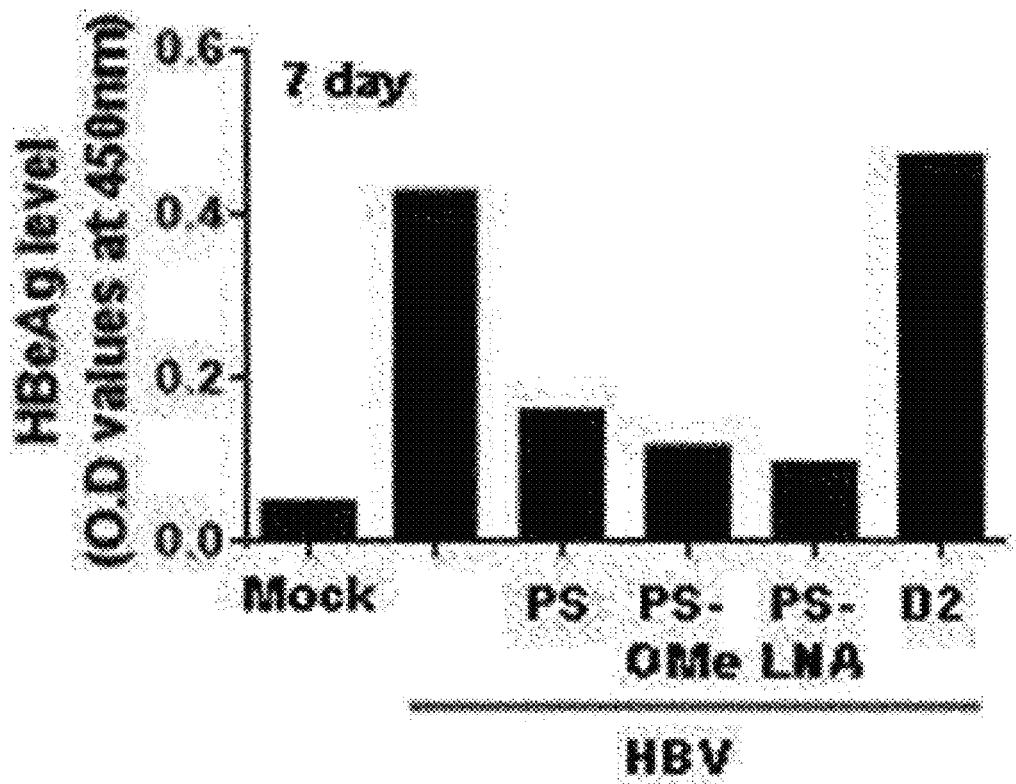
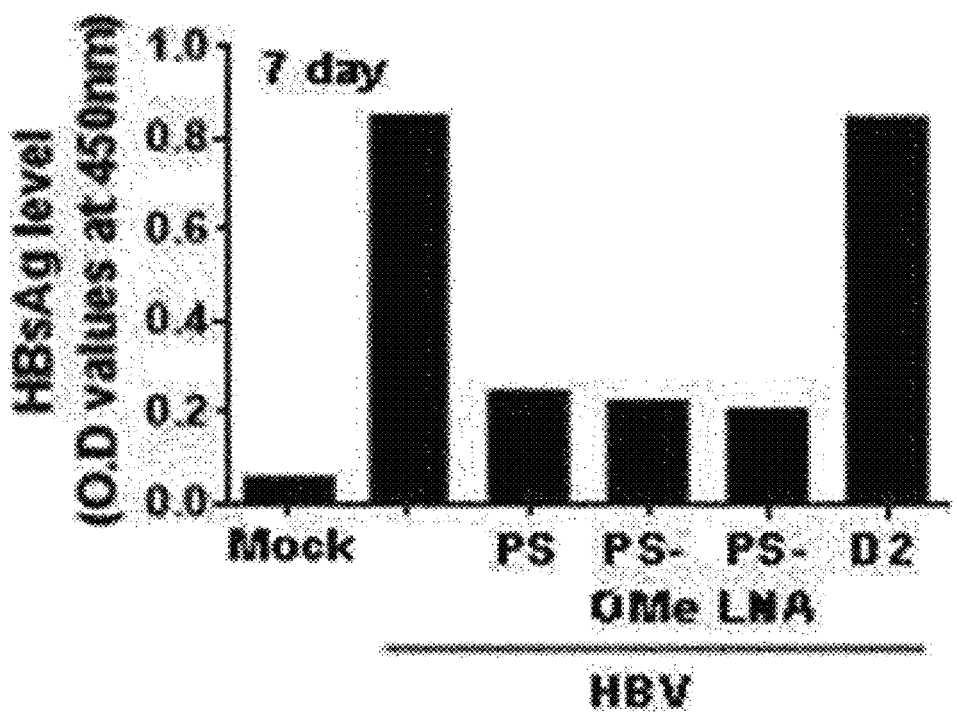
FIG. 13C

FIG. 21D
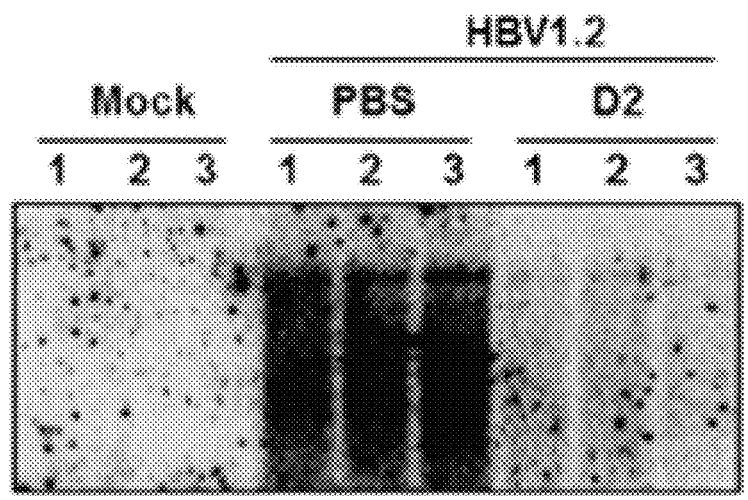
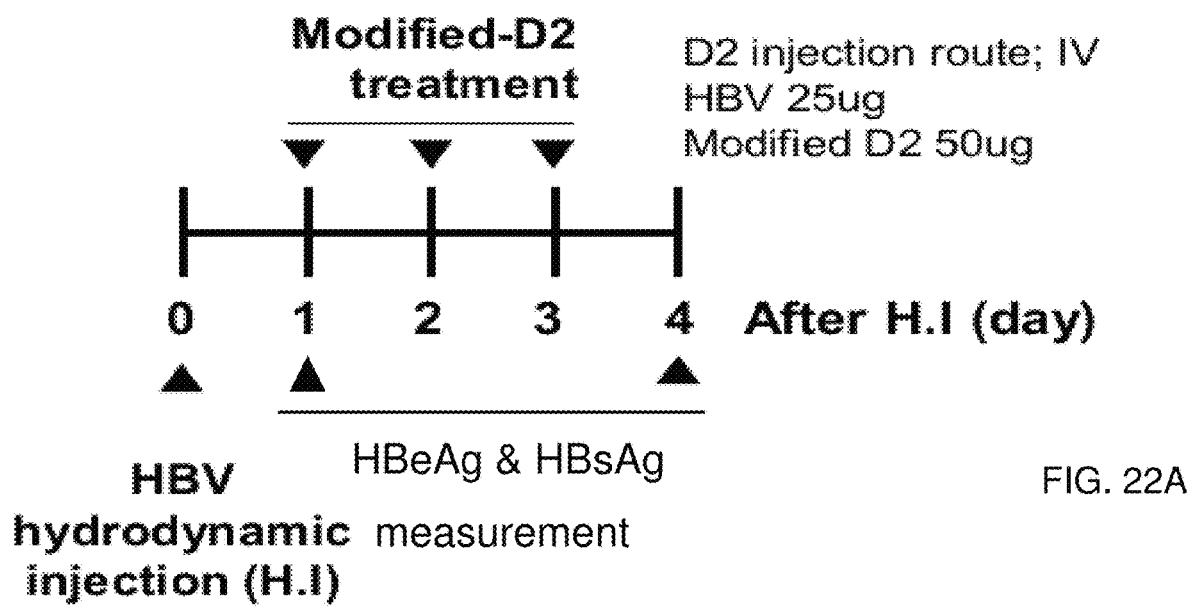
FIG. 22A

FIG. 22B
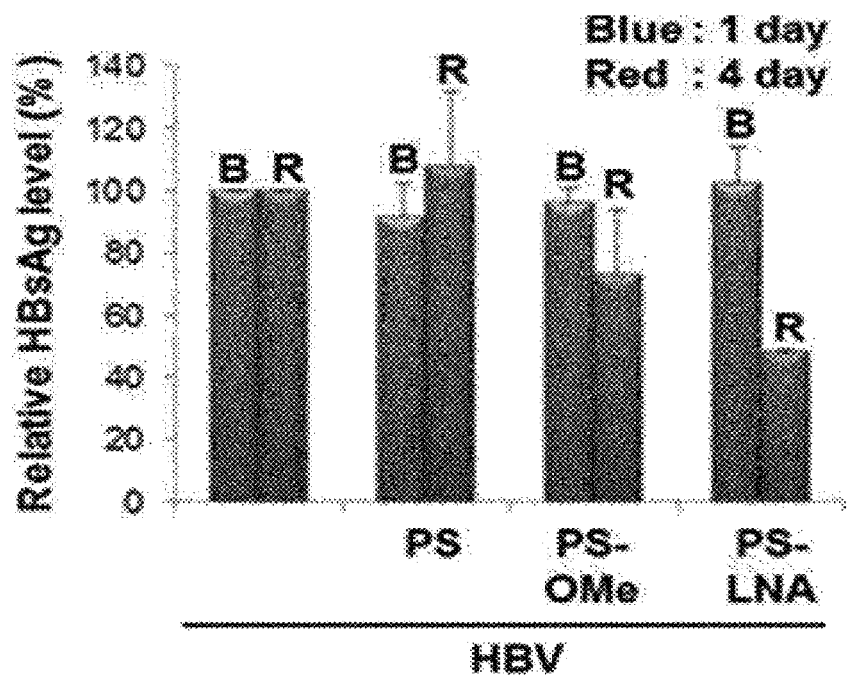
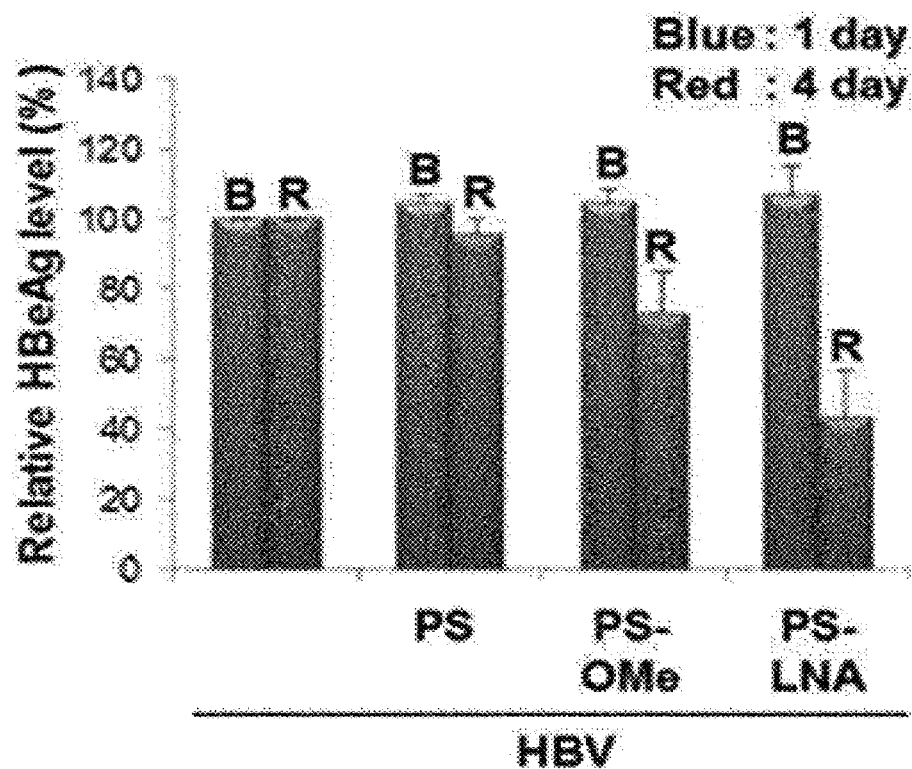
FIG. 22C

FIG. 22D
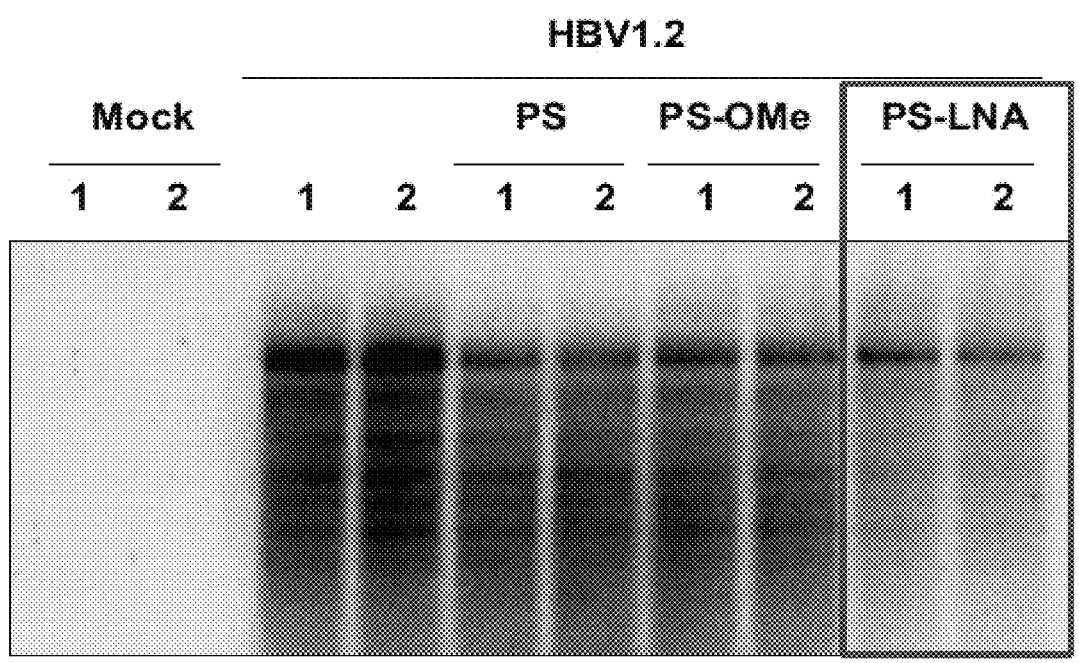
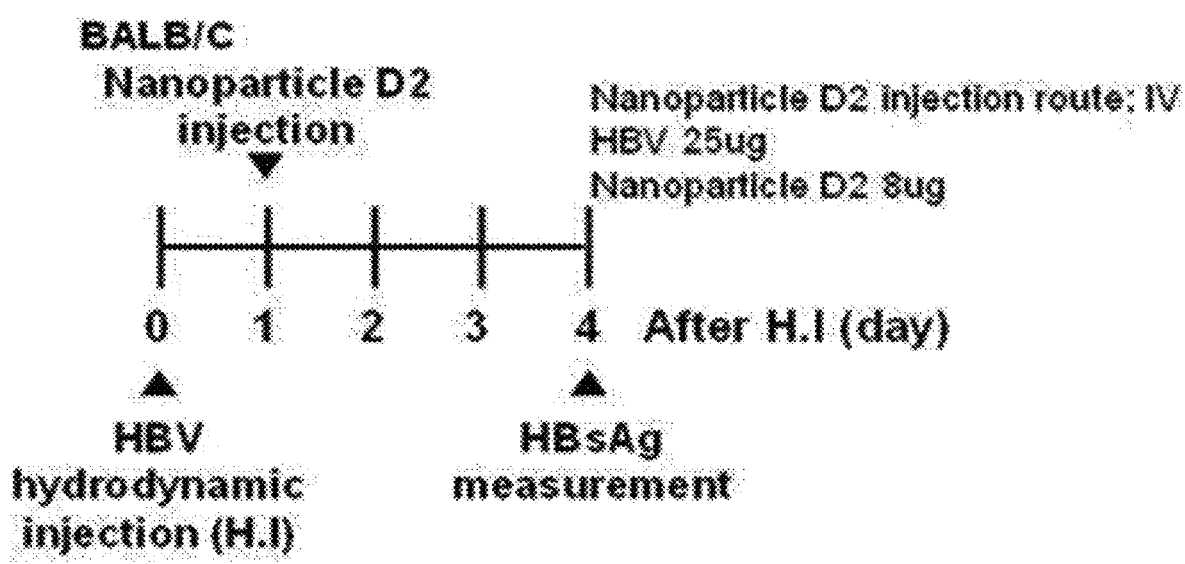
FIG. 23A

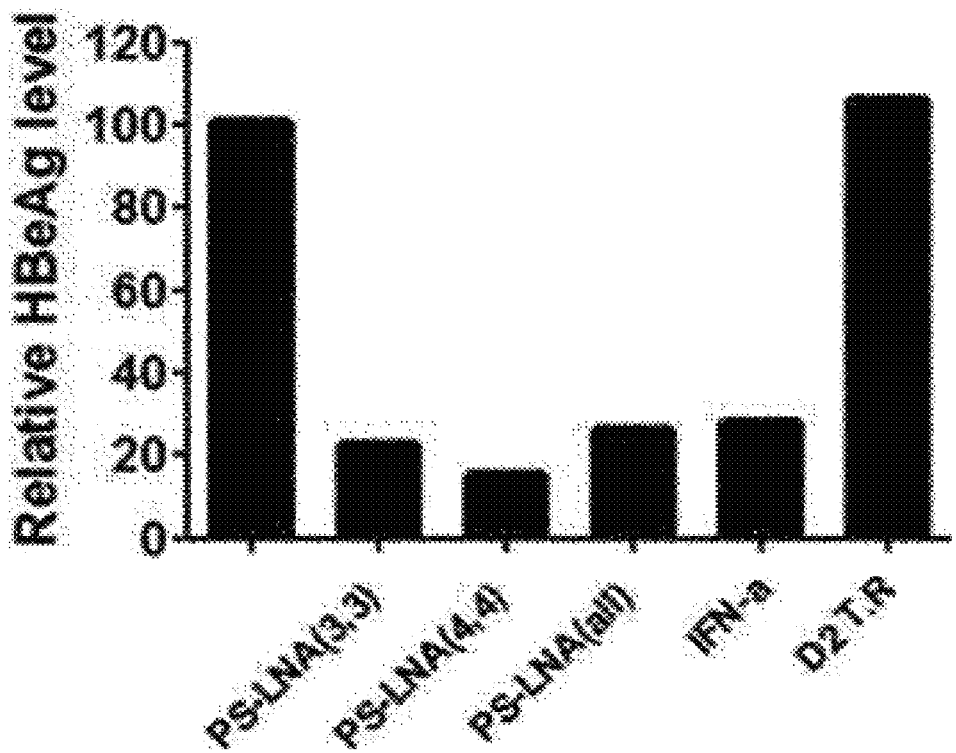
FIG. 24B
FIG. 24C
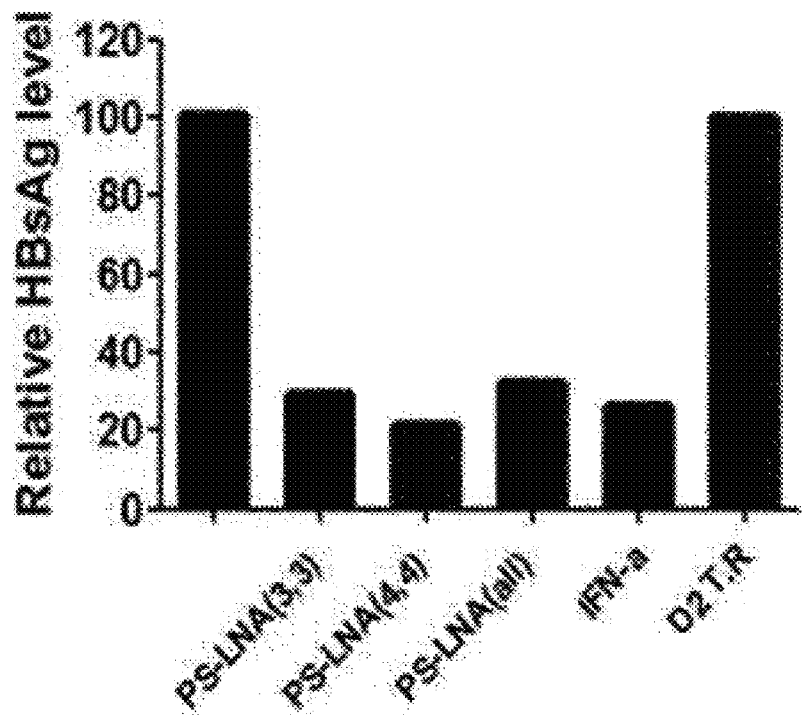

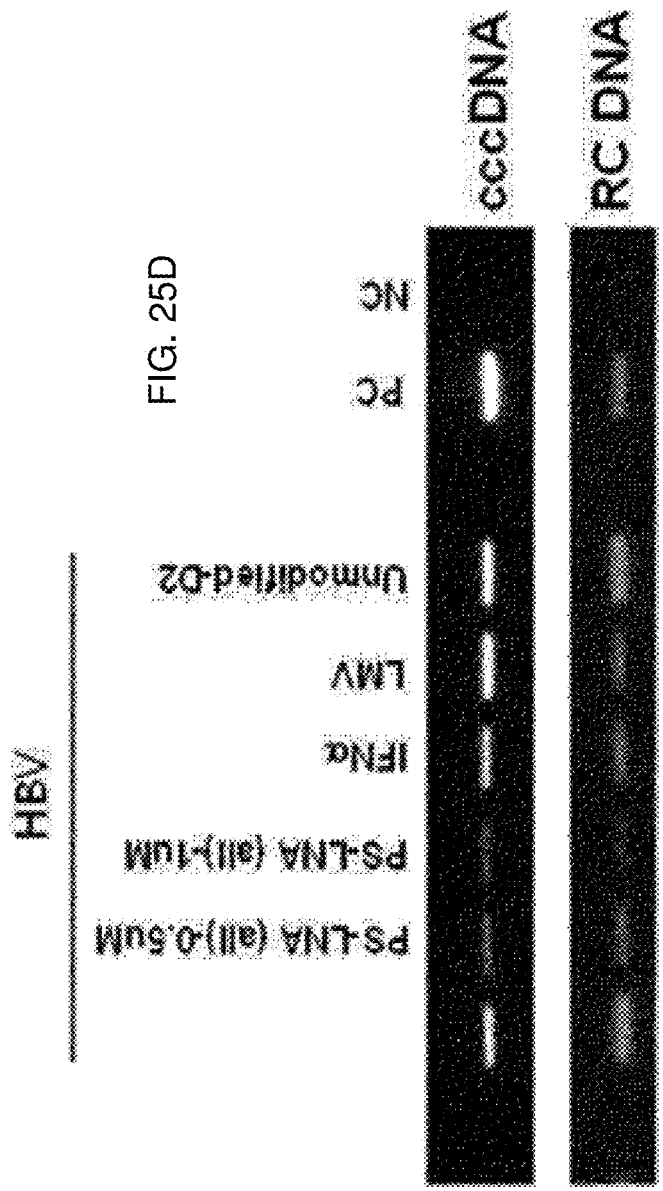

PHARMACEUTICAL COMPOSITION FOR PREVENTING OR TREATING HEPATITIS B

SEQUENCE LISTING

The instant application contains a Sequence Listing which has been submitted electronically in ASCII format and is hereby incorporated by reference in its entirety. Said ASCII copy, created on Jun. 12, 2019 is named 51393-002001 Sequence Listing 6.12.19 ST25 and is 69,843 bytes in size.

TECHNICAL FIELD

The present invention relates to a method for treating hepatitis B by administering an oligonucleotide for preventing or treating hepatitis B and a pharmaceutical composition including the oligonucleotide.

BACKGROUND ART

Among virus infections, hepatitis B virus (hereinafter referred to as HBV) has the most harmful effect on humans, afflicting more than 350 million people worldwide. When an individual is infected with HBV, it can cause liver diseases such as chronic hepatitis, cirrhosis, hepatocellular carcinoma, etc., and in severe cases, viral liver diseases can lead to death. HBV has a DNA genome, and it is one of the viruses having the smallest genome known so far (Ganem and Prince *N Engl J Med* (2004) 350, 1118-1129).

Currently, the rate of new infections has been significantly decreasing since the development of vaccines that can prevent HBV infection, but the infection status is still critical in underdeveloped countries. In addition, there are many patients who are infected with HBV before vaccination, causing a large number of social problems.

HBV is a virus having a 3.2 kb double-stranded DNA genome, and the DNA is surrounded by a capsid protein, while the capsid protein is surrounded by a surface protein. HBV has prominent features in that it shows hepatotropism, provokes persistent infection in a non-cytotoxic state, and has very restricted host tropism; it is not infectious to animals other than humans and chimpanzees (Ganem and Prince *N Engl J Med* (2004) 350, 1118-1129).

After HBV infection, the capsid is disassembled and the gene is delivered to the nucleus, where the double-stranded DNA is converted to cccDNA (covalently closed circular DNA). The cccDNA has an important role in the HBV life cycle, serving as a template for transcription of HBV. Recent studies have demonstrated that cccDNA is encapsidated by histones and can be modulated by various modifications of the histones (Pollicino et al. *Gastroenterology* (2006) 130, 823-837). The cccDNA, which exists as an episomal minichromosome, is known to be a major cause of chronic infection not only because it produces all RNAs of HBV, but also, the current anti-HBV therapeutic agents cannot eliminate cccNDA (Urban et al. *J Hepatol* (2010) 52, 282-284).

The viral RNA produced from cccDNA creates the core, surface, polymerase, etc., and encapsidation is performed based on pregenomic RNA that can be transformed to genomic DNA in the cytoplasm. HBV virions that have been successfully transformed to DNA from the pregenomic RNA are budded. After budding, the virions are steadily proliferated by infecting or reinfecting peripheral hepatocytes (Urban et al. *J Hepatol* (2010) 52, 282-284).

All currently used hepatitis B therapeutic agents are nucleic acid derivatives, and they work by interfering with the new DNA strand of the virus, when the pregenomic RNA is transformed to DNA by a polymerase in the capsid, and eventually terminate the synthesis. Thus, all currently available therapeutic agents targeting this part induce drug resistance when a mutation occurs in the active site of the RT (reverse transcriptase) domain of HBV polymerase, and therefore, it is difficult to provide a complete cure due to these drug-resistant mutations in long-term treatment (Zoulim and Locarnini, *Gastroenterology* (2009) 137, 1593-1608 e1591-1592).

Nucleic acid analogs that are currently approved by the FDA as therapeutic agents for chronic hepatitis B include lamivudine, adefovir, entecavir, telbivudine, clevudine, and tenofovir, and since these are all polymerase inhibitors, they cannot completely cure chronic hepatitis.

In 2014, Lucifora et al. reported that IFN-α and lymphotoxin b receptor (LTbR) can up-regulate APOBEC3A or APOBEC3B and selectively remove cccDNA without apoptosis. However, it may be difficult to apply practically because large amounts must be used.

A cell-based cccDNA assay was constructed and 85,000 compounds were screened. As a result, it was found that two disubstituted sulfonamides (DSS), named CCC-0975 and CCC-0346, were able to reduce cccDNA to some extent, but the effect is still insufficient for development as a drug, and also, the mechanism of action is unknown (Cal et al. *Antimicrob Agents Chemother*. (2012) August; 56(8):4277-88).

Therefore, new treatments are needed to treat HBV infection. In this regard, the present inventors analyzed the genome of HBV, and thus discovered a part capable of forming a G-quadruplex and developed a technique of regulating the activity of the HBV gene and removing the cccDNA of HBV. The G-quadruplex is a four-stranded helical DNA structure formed based on the bonding between four guanines (Metifiot et al. *Nucleic Acids Res.* 2014 Nov. 10; 42(20):12352-66. Epub 2014 Oct. 20).

DISCLOSURE

Technical Problem

It is one object of the present invention to provide a pharmaceutical composition for treating or preventing hepatitis B, including: at least one oligonucleotide selected from the group consisting of an oligonucleotide represented by a nucleic acid sequence of SEQ ID NO: 1, 2, or 6 or a complimentary nucleic acid sequence thereof; and an oligonucleotide having at least one chemical modification on the oligonucleotide, as an active ingredient.

Further, it is another object of the present invention to provide a method for treating or preventing hepatitis B, including: administering an effective dose of the pharmaceutical composition to an individual.

Furthermore, it is still another object of the present invention to provide a method for screening a therapeutic agent for hepatitis B, including: contacting hepatitis B virus (HBV) with a candidate material and confirming whether HBV forms a G-quadruplex with the candidate material.

Technical Solution

In one aspect, there is provided a pharmaceutical composition for treating or preventing hepatitis B, including: at least one oligonucleotide selected from the group consisting of an oligonucleotide represented by a nucleic acid sequence of SEQ ID NO: 1, 2, or 6 or a complimentary nucleic acid sequence thereof; and an oligonucleotide having at least one chemical modification on the oligonucleotide, as an active ingredient.

In some embodiments, the oligonucleotide having a chemical modification may have at least one chemically modified internucleoside linkage.

In some embodiments, the oligonucleotide having a chemically modified internucleoside linkage may have a chemical modification in which the phosphate group of a nucleotide is chemically modified with phosphorothioate, phosphorodithioate, phosphoramidate, or boranophosphate.

In some embodiments, the oligonucleotide having a chemical modification may have at least one chemically modified sugar moiety.

In some embodiments, the sugar moiety may be modified such that the —H group at the 2' position of the pentose in a nucleotide is substituted with methoxyethyl (MOE), dimethylaminooxyethoxy (DMAOE), dimethylaminoethoxyethyl (DMAEOE), methyl (OMe), aminopropoxy (AP), or fluoro (F), or the sugar moiety may be substituted with F-ANA.

In some embodiments, the sugar moiety may be chemically modified in the form of LNA (locked nucleic acid) or PNA (peptide nucleic acid).

In some embodiments, the oligonucleotide may be in a state where GalNAc (N-acetylgalactosamine) is bound to the 3' or 5' end via a linker.

In some embodiments, the oligonucleotide having a chemical modification may have two or more chemical modifications selected from the group consisting of a chemical modification of the internucleoside linkage and a chemical modification of the sugar moiety.

In some embodiments, the oligonucleotide having two or more chemical modifications may have a chemical modification in which the phosphate group of a nucleotide is chemically modified with phosphorothioate, phosphorodithioate, phosphoramidate, or boranophosphate, and may further have a chemical modification in which the —H group at the 2' position of the pentose in a nucleotide is substituted with methoxyethyl (MOE), dimethylaminooxyethoxy (DMAOE), dimethylaminoethoxyethyl (DMAEOE), methyl (OMe), aminopropoxy (AP), or fluoro (F), or the sugar moiety of the nucleotide may be substituted with F-ANA.

In some embodiments, the oligonucleotide having two or more chemical modifications may have a chemical modification in which the phosphate group of a nucleotide is chemically modified with phosphorothioate, phosphorodithioate, phosphoramidate, or boranophosphate, and may further have a chemical modification in which the sugar moiety is chemically modified in the form of LNA (locked nucleic acid) or PNA (peptide nucleic acid).

In some embodiments, the oligonucleotide having two or more chemical modifications may have a chemical modification in which the phosphate group of a nucleotide is chemically modified with phosphorothioate, phosphorodithioate, phosphoramidate, or boranophosphate, and may be further in a state where GalNAc (N-acetylgalactosamine) is bound to the 3' or 5' end via a linker.

In some embodiments, the oligonucleotide may form a G-quadruplex with HBV.

In some embodiments, the pharmaceutical composition for treating or preventing hepatitis B may reduce cccDNA (covalently closed circular DNA) of HBV.

In some embodiments, the pharmaceutical composition for treating or preventing hepatitis B may further include a pharmaceutically acceptable carrier.

In some embodiments, the pharmaceutically acceptable carrier may include chitosan nanoparticles, colloidal dispersion systems, macromolecule complexes, nanocapsules, nanoparticles, microspheres, beads, and oil-in-water emulsions, micelles, mixed micelles, or liposomes, but is not limited thereto.

In some embodiments, the pharmaceutically acceptable carrier may be a chitosan nanoparticle, and the chitosan may have a molecular weight of 50 kDa to 190 kDa.

In some embodiments, the pharmaceutical composition for treating or preventing hepatitis B may be administered orally or parenterally to an individual.

In some embodiments, the pharmaceutical composition for treating or preventing hepatitis B may be administered intraperitoneally, intravenously, percutaneously, sublingually, intramuscularly, intranasally, or subcutaneously to an individual.

The oligonucleotide disclosed herein may be used in the prevention and/or treatment of hepatitis B, and in the manufacture of pharmaceuticals for treatment thereof.

In another aspect, there is provided a method for treating or preventing hepatitis B, including: administering an effective dose of a pharmaceutical composition for treating or preventing hepatitis B including at least one oligonucleotide selected from the group consisting of an oligonucleotide represented by a nucleic acid sequence of SEQ ID NO: 1, 2, or 6 or a complimentary nucleic acid sequence thereof; and an oligonucleotide having at least one chemical modification on the oligonucleotide, as an active ingredient, to an individual.

In some embodiments, the oligonucleotide having a chemical modification may have at least one chemically modified internucleoside linkage.

In some embodiments, the oligonucleotide having a chemically modified internucleoside linkage may have a chemical modification in which the phosphate group of a nucleotide is chemically modified with phosphorothioate, phosphorodithioate, phosphoramidate, or boranophosphate.

In some embodiments, the oligonucleotide having a chemical modification may have at least one chemically modified sugar moiety.

In some embodiments, the sugar moiety may be modified such that the —H group at the 2' position of the pentose in a nucleotide is substituted with methoxyethyl (MOE), dimethylaminooxyethoxy (DMAOE), dimethylaminoethoxyethyl (DMAEOE), methyl (OMe), aminopropoxy (AP), or fluoro (F), or the sugar moiety may be substituted with F-ANA.

In some embodiments, the sugar moiety may be chemically modified in the form of LNA (locked nucleic acid) or PNA (peptide nucleic acid).

In some embodiments, the oligonucleotide may be in a state where GalNAc (N-acetylgalactosamine) is bound to the 3' or 5' end via a linker.

In some embodiments, the oligonucleotide having a chemical modification may have two or more chemical modifications selected from the group consisting of a chemical modification of the internucleoside linkage and a chemical modification of the sugar moiety.

In some embodiments, the oligonucleotide having two or more chemical modifications may have a chemical modification in which the phosphate group of a nucleotide is chemically modified with phosphorothioate, phosphorodithioate, phosphoramidate, or boranophosphate, and may further have a chemical modification in which the —H group at the 2' position of the pentose in a nucleotide is substituted with methoxyethyl (MOE), dimethylaminooxyethoxy (DMAOE), dimethylaminoethoxyethyl (DMAEOE), methyl (OMe), aminopropoxy (AP), or fluoro (F), or the sugar moiety of the nucleotide may be substituted with F-ANA.

In some embodiments, the oligonucleotide having two or more chemical modifications may have a chemical modification in which the phosphate group of a nucleotide is chemically modified with phosphorothioate, phosphorodithioate, phosphoramidate, or boranophosphate, and may further have a chemical modification in which the sugar moiety is chemically modified in the form of LNA (locked nucleic acid) or PNA (peptide nucleic acid).

In some embodiments, the oligonucleotide having two or more chemical modifications may have a chemical modification in which the phosphate group of a nucleotide is chemically modified with phosphorothioate, phosphorodithioate, phosphoramidate, or boranophosphate, and may be further in a state where GalNAc (N-acetylgalactosamine) is bound to the 3' or 5' end via a linker.

In some embodiments, the oligonucleotide may form a G-quadruplex with HBV.

In some embodiments, the pharmaceutical composition for treating or preventing hepatitis B may reduce cccDNA (covalently closed circular DNA) of HBV.

In some embodiments, the pharmaceutical composition for treating or preventing hepatitis B may further include a pharmaceutically acceptable carrier.

In some embodiments, the pharmaceutically acceptable carrier may include chitosan nanoparticles, colloidal dispersion systems, macromolecule complexes, nanocapsules, nanoparticles, microspheres, beads, and oil-in-water emulsions, micelles, mixed micelles, or liposomes, but is not limited thereto.

In some embodiments, the pharmaceutically acceptable carrier may be a chitosan nanoparticle, and the chitosan may have a molecular weight of 50 kDa to 190 kDa.

In some embodiments, the pharmaceutical composition for treating or preventing hepatitis B may be administered orally or parenterally to an individual.

In some embodiments, the pharmaceutical composition for treating or preventing hepatitis B may be administered intraperitoneally, intravenously, percutaneously, sublingually, intramuscularly, intranasally, or subcutaneously to an individual.

In still another aspect, there is provided a method for screening a therapeutic agent for hepatitis B, including: contacting hepatitis B virus (HBV) with a candidate material and confirming whether the HBV forms a G-quadruplex with the candidate material.

In some embodiments, the method may include selecting the candidate material as a therapeutic agent for hepatitis B if HBV forms a G-quadruplex with the candidate material.

In some embodiments, the formation of G-quadruplex may be confirmed by electrophoretic mobility shift assay (EMSA), circular dichroism (CD), nuclear magnetic resonance (NMR), and a method of using G-quadruplex-specific antibodies.

In some embodiments, the candidate material may include 4 or more guanines (G).

In some embodiments, the candidate material may suppress HBV expression by binding with an enhancer II region of HBV and forming a G-quadruplex.

Advantageous Effects

The pharmaceutical composition for treating or preventing hepatitis B including an oligonucleotide represented by a nucleic acid sequence of SEQ ID NO: 1, 2, or 6, or a complimentary nucleic acid sequence thereof and an oligonucleotide having at least one chemical modification on the oligonucleotide, as an active ingredient, forms a G-quadruplex, thereby reducing cccDNA (covalently closed circular DNA) of HBV, and thus can be used for the treatment and prevention of hepatitis B, or for screening a therapeutic agent for hepatitis B.

BRIEF DESCRIPTION OF DRAWINGS

FIGS. 2A and 2B show the secretion rate of HBeAg and HBsAg of HBV 1.2 plasmid, respectively, ands FIG. 2C shows the results of HBV DNA Southern blot.

FIGS. 12B and 12C show the analysis results of HBV protein expression upon treatment with the modified oligonucleotides. PS represents a D2 modified with phosphorothioate, PS-OMe represents a D2 modified with phosphorothioate and O-methyl, and PS-LNA represents a D2 modified with phosphorothioate and LNA. Transfection (D1, T.F) of D2 was used as a positive control for anti-HBV effect. Unmodified D2 treatment (D2 Tr) was used as a negative control. LMV is lamivudine.

FIG. 13A schematically shows HBV transfection and viral protein analysis of PHHs (primary human hepatocytes). FIGS. 13B and 13C show the analysis results of HBV protein expression upon treatment with modified oligonucleotides. PS represents a D2 modified with phosphorothioate, PS-OMe represents a D2 modified with phosphorothioate and O-methyl, and PS-LNA represents a D2 modified with phosphorothioate and LNA. Transfection (D1, T.F) of D2 was used as a positive control for anti-HBV effect. Unmodified D2 treatment (D2 Tr) was used as a negative control.

Figure 14:
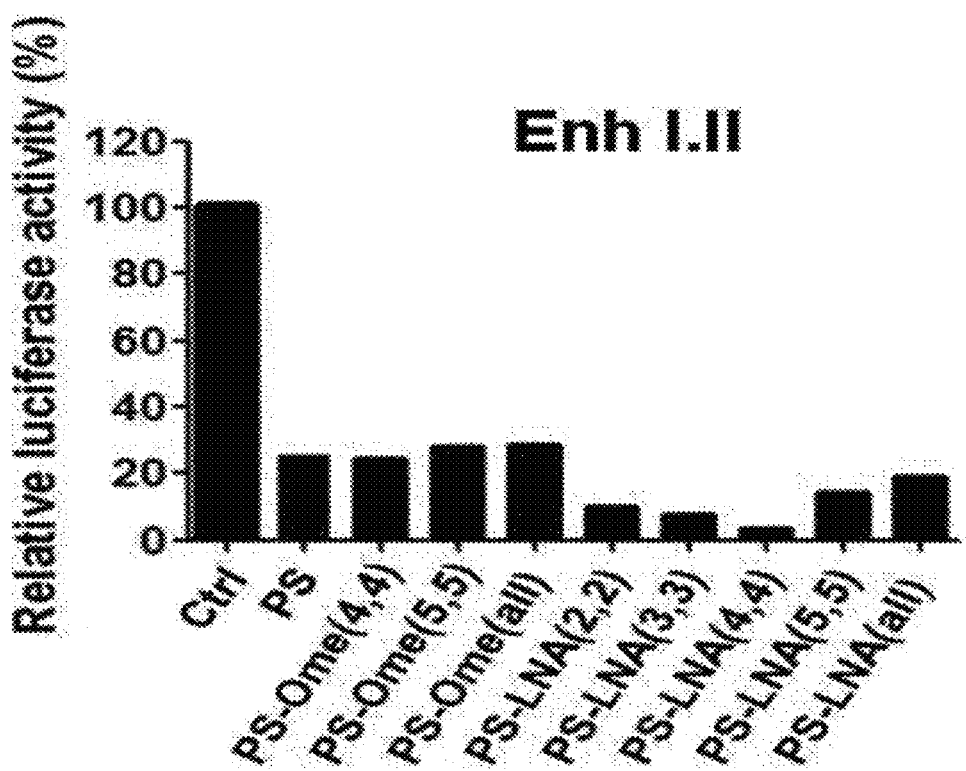

FIG. 14 shows the results of luciferase assay, illustrating the anti-HBV activity of modified D2. PS represents a D2 whose backbone is modified with PS, PS-Ome (4,4) represents a D2 whose backbone is PS and in which 4 nucleotides at each of the 5' and 3' ends are modified with O-Methyl, PS-Ome (5,5) represents a D2 whose backbone is PS and in which 5 nucleotides at each of the 5' and 3' ends are modified with O-Methyl, PS-Ome (all) represents a D2 whose backbone is PS and in which all nucleotides are modified with O-Methyl, PS-LNA (2,2) represents a D2 whose backbone is PS and in which 2 nucleotides at each of the 5' and 3' ends are modified with LNA, PS-LNA (3,3) represents a D2 whose backbone is PS and in which 3 nucleotides at each of the 5' and 3' ends are modified with LNA, PS-LNA (4,4) represents a D2 whose backbone is PS and in which 4 nucleotides at each of the 5' and 3' ends are modified with LNA, PS-LNA (5,5) represents a D2 whose backbone is PS and in which 5 nucleotides at each of the 5' and 3' ends are modified with LNA, and PS-LNA (all) represents a D2 whose backbone is PS and in which all nucleotides are modified with LNA.

Figure 15:
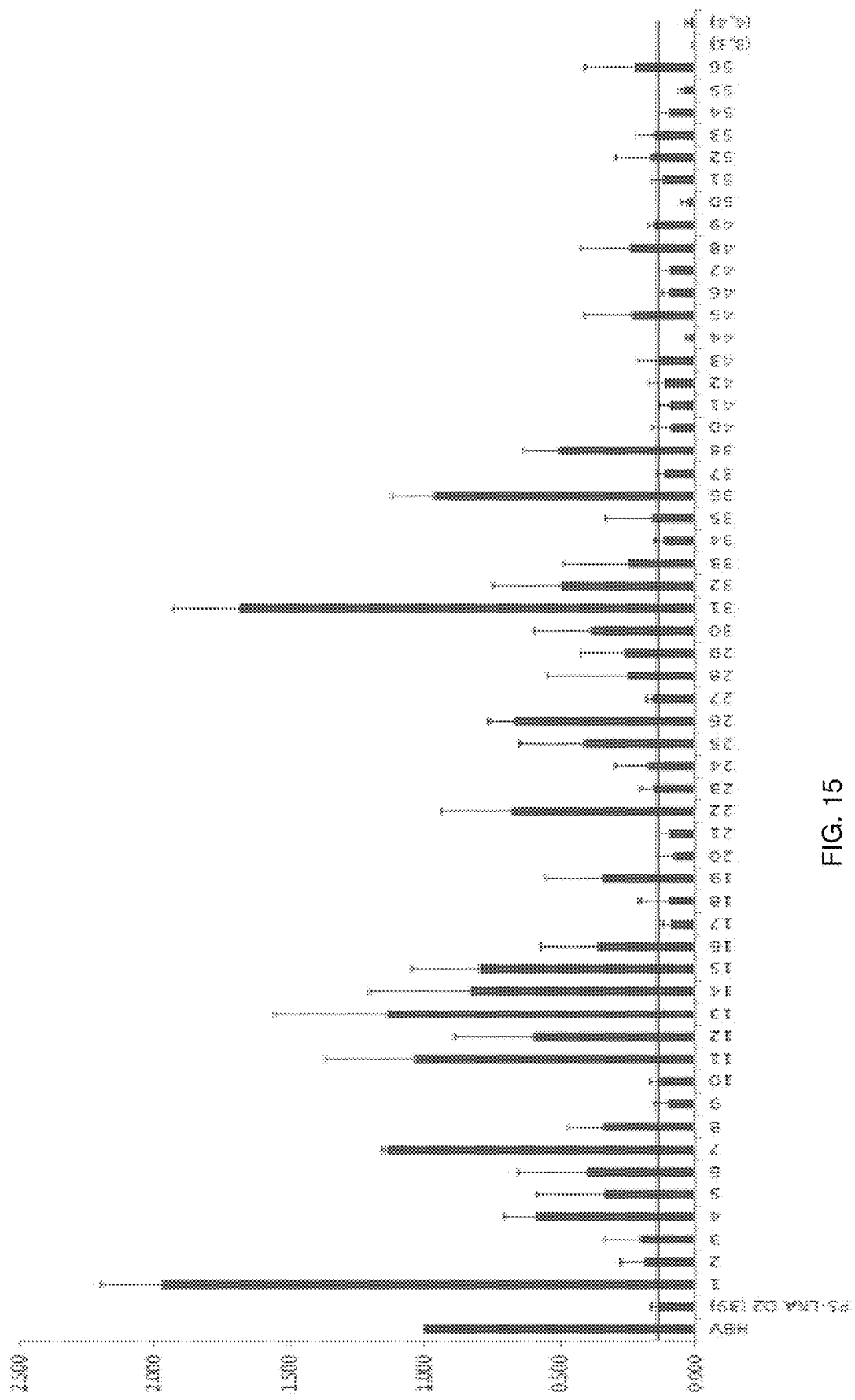

FIG. 15 shows the HBeAg inhibitory activity of 58 modified oligonucleotides in HepG2 cells.

Figure 16:
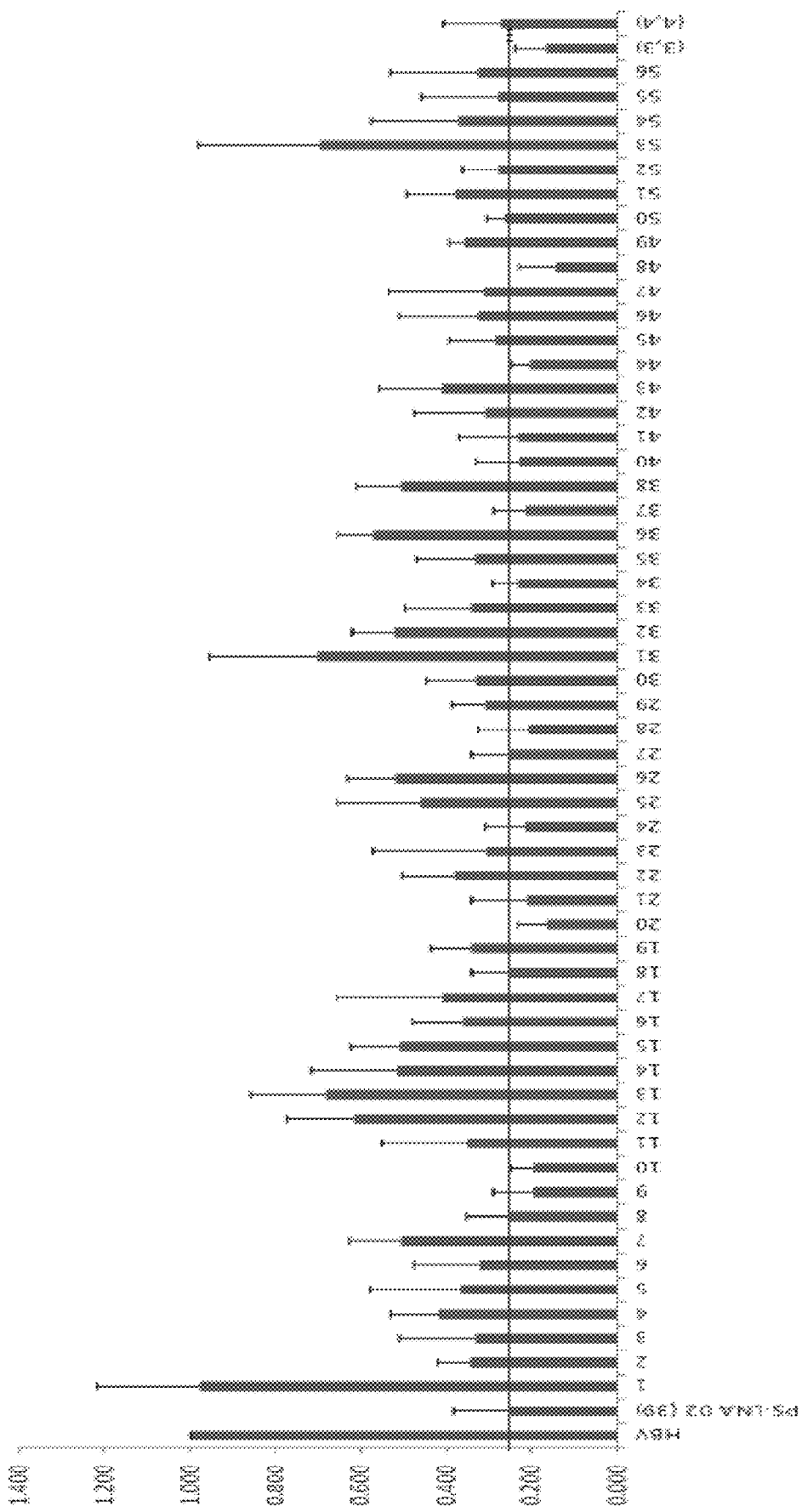

FIG. 16 shows the HBsAg inhibitory activity of 58 modified oligonucleotides in HepG2 cells.

Figure 17:
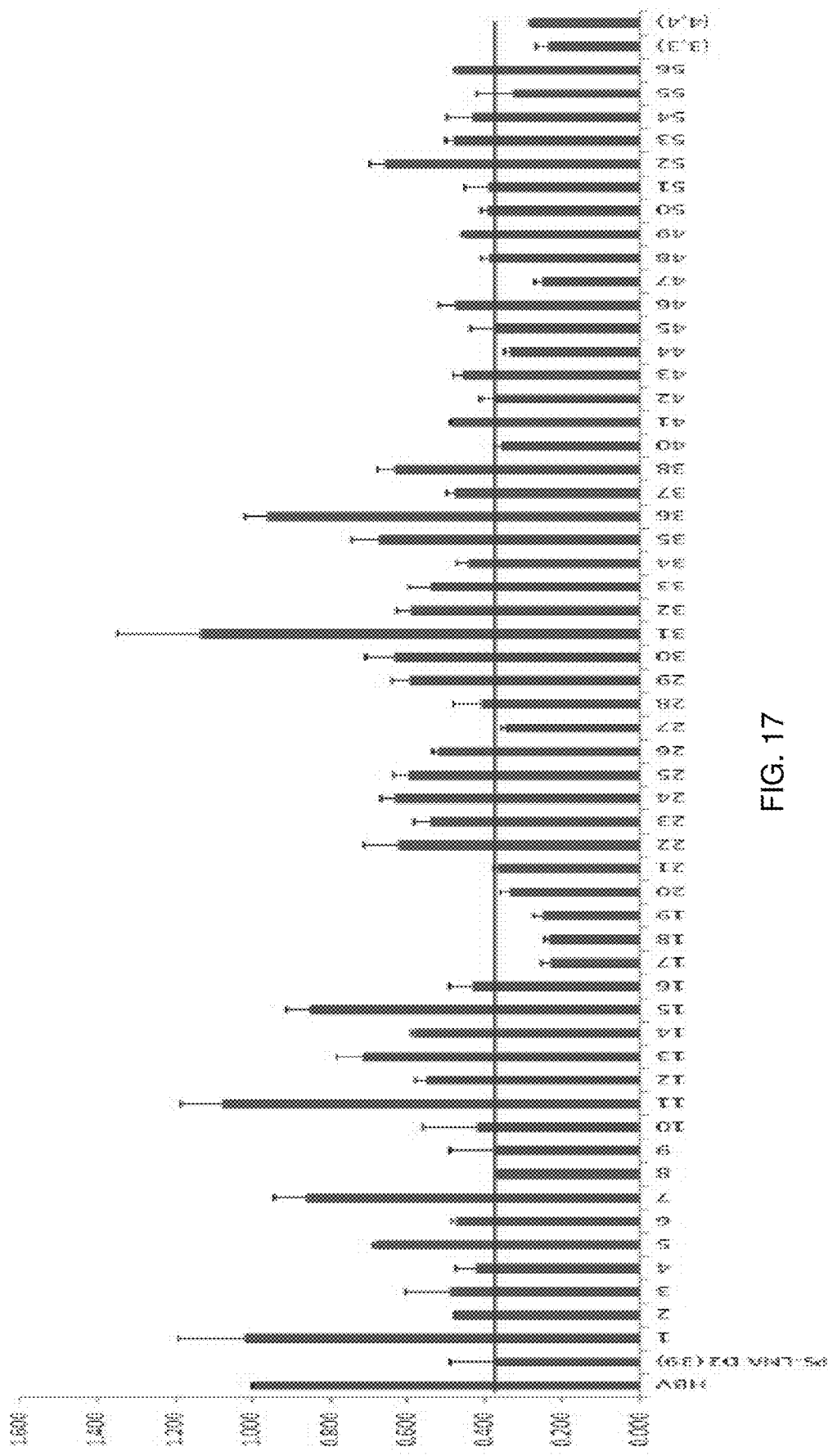

FIG. 17 shows the HBeAg inhibitory activity of 58 modified oligonucleotides in HepG2-NTCP cells.

Figure 18:
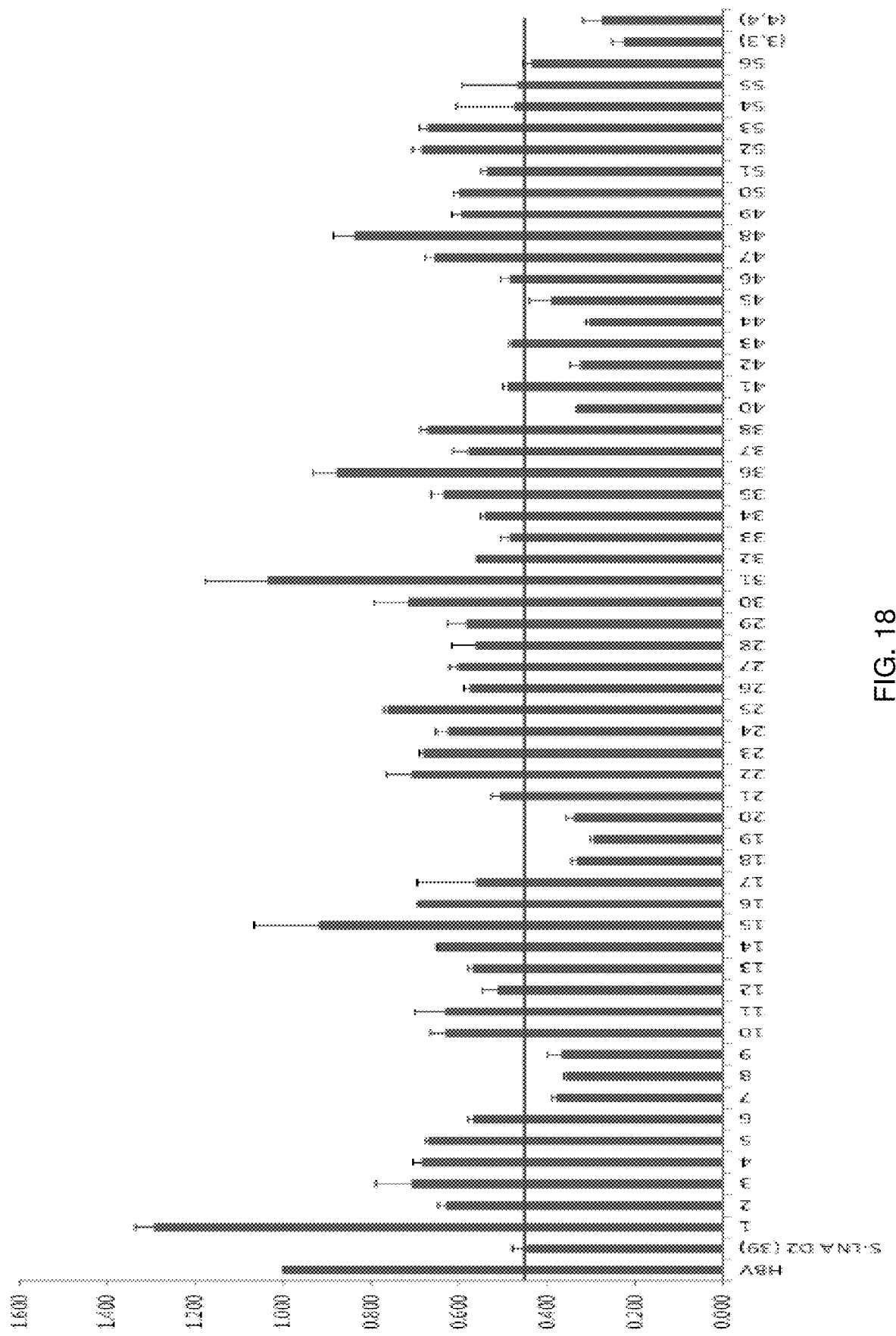

FIG. 18 shows the HBsAg inhibitory activity of 58 modified oligonucleotides in HepG2-NTCP cells.

Figure 19:
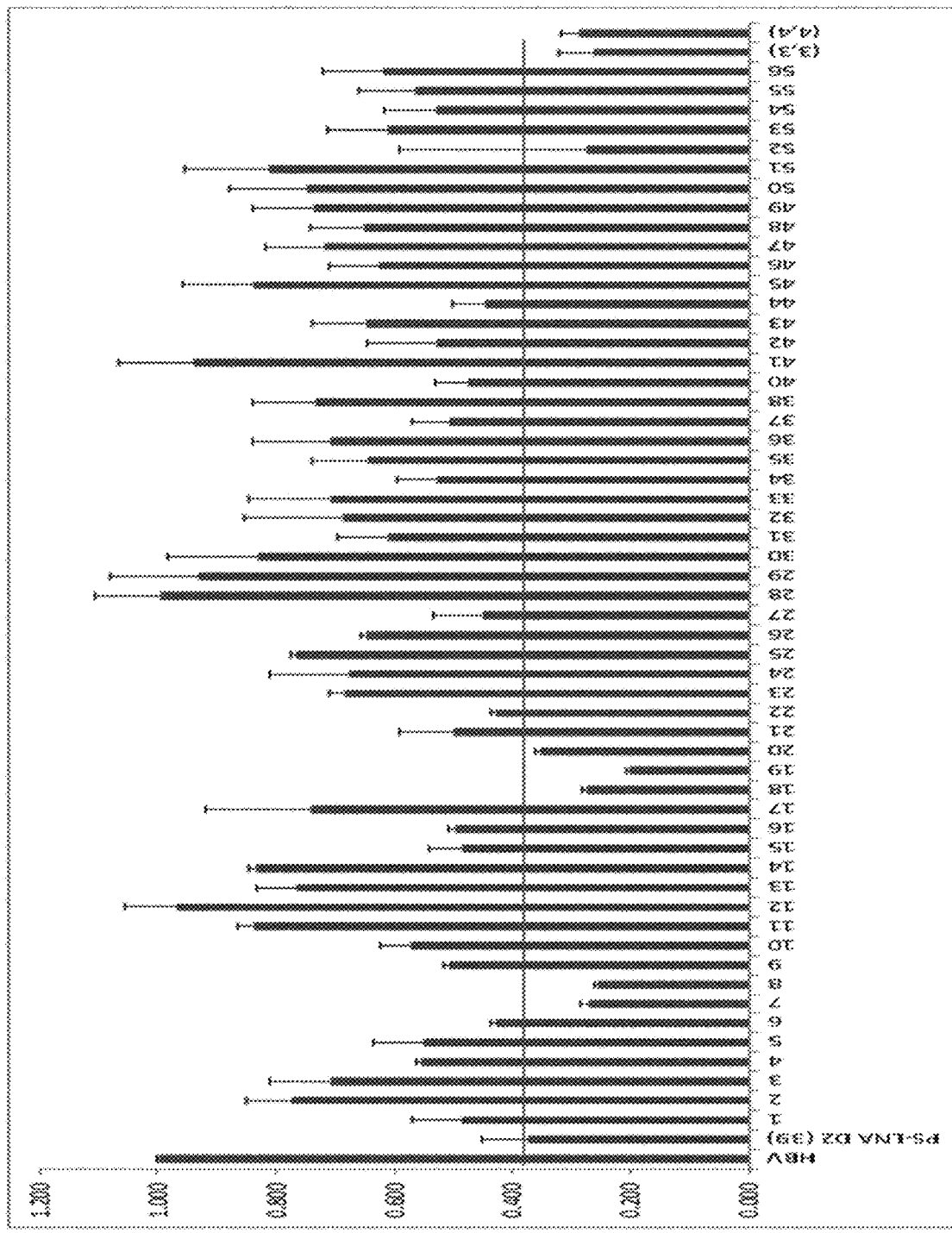

FIG. 19 shows the HBeAg inhibitory activity of 58 modified oligonucleotides in PHH cells.

Figure 20:
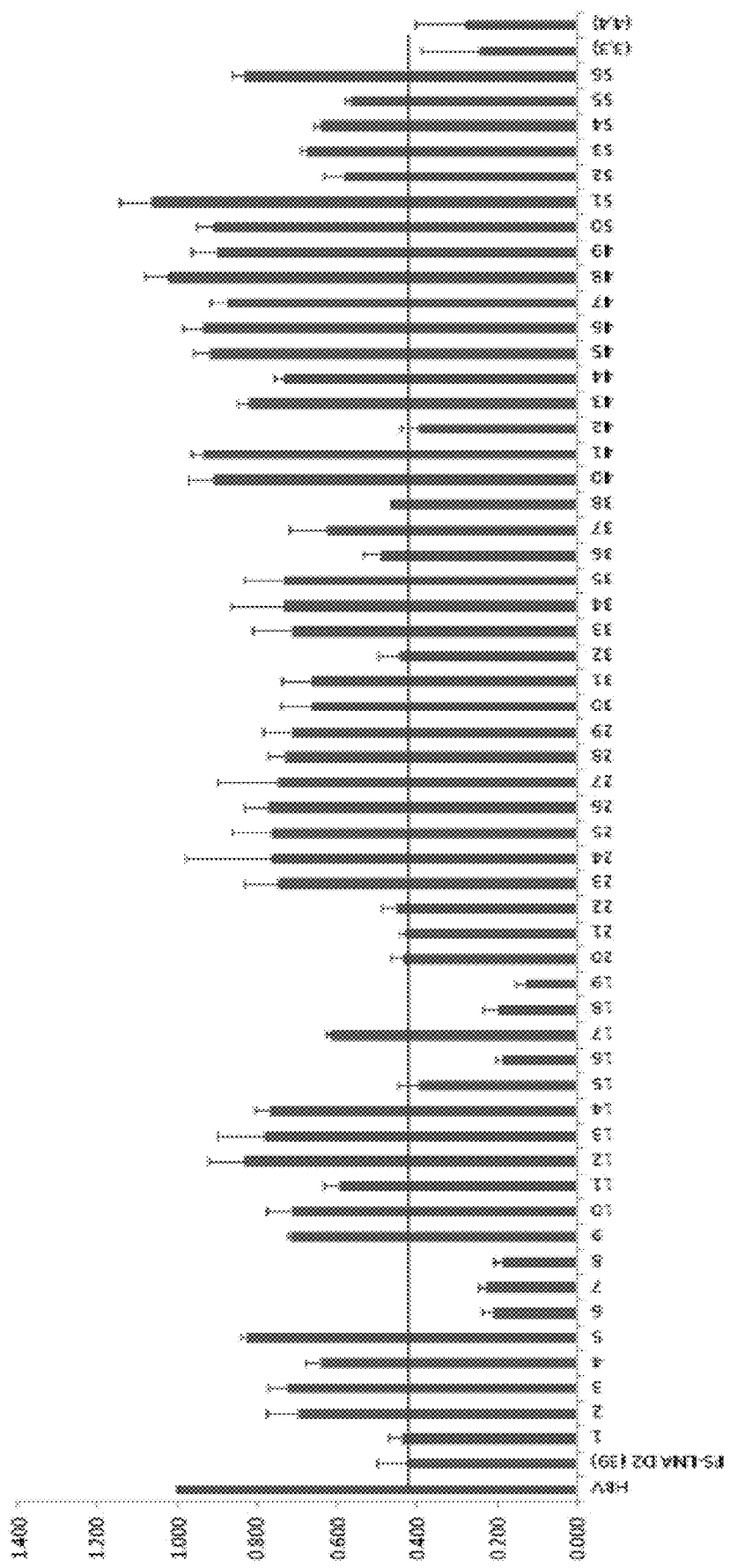

FIG. 20 shows the HBsAg inhibitory activity of 58 modified oligonucleotides in PHH cells.

Figure 21A:
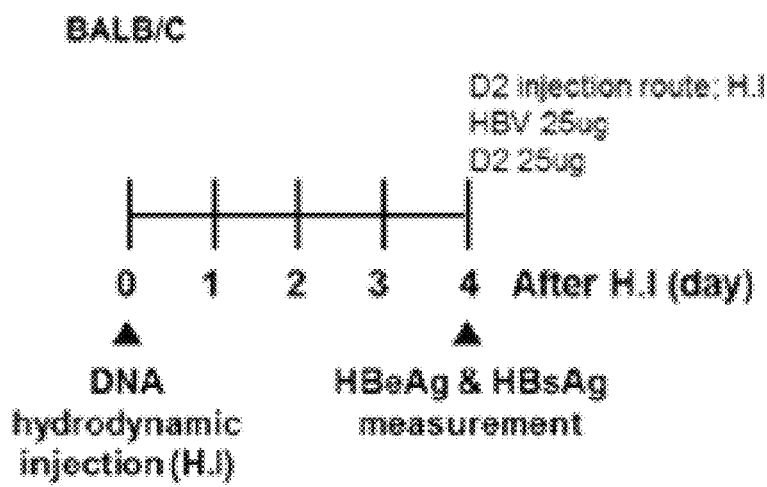
Figure 21B:
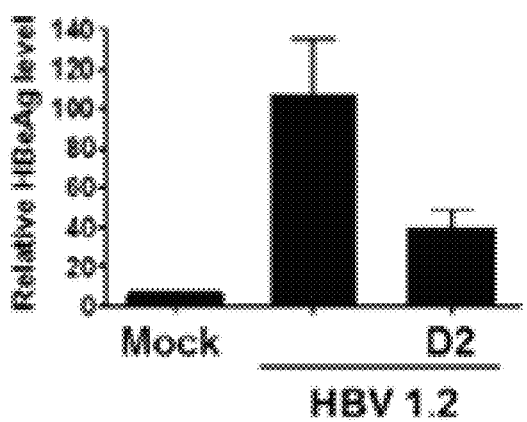
Figure 21C:
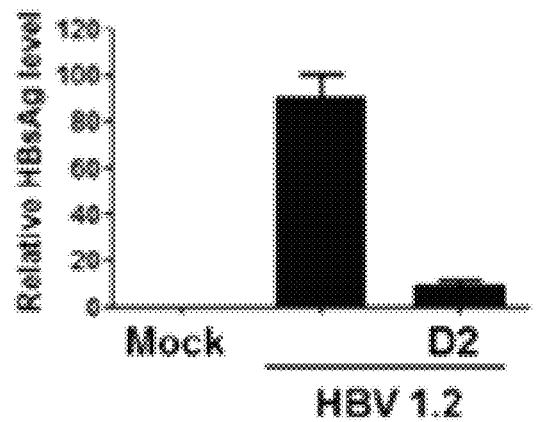

FIGS. 21A-21C show that the oligonucleotides inhibit HBV in an in vivo model. FIG. 21A is a schematic illustration of an in vivo experimental schedule, and FIGS. 21B and 21C are the measurement results of the viral proteins HBeAg and HBsAg, respectively. Mock, the first bar of FIGS. 21B and 21C, represents a control mouse, the second bar represents an experimental group containing HBV with an empty vector, and the third bar represents an experimental group containing HBV DNA and D2. FIG. 21D shows confirmation that HBV DNA was greatly reduced in the mice injected with D2 oligonucleotides using Southern blot.

FIGS. 22A-22D show that the modified oligonucleotides inhibit HBV when injected intravenously into an in vivo model. FIG. 22A is a schematic illustration of an in vivo intravenous (IV) injection experimental schedule, and FIGS. 22B and 22C are the measurement results of viral proteins HBeAg and HBsAg, respectively. FIG. 22D is the result confirmed by Southern blot, and each numerical value indicates the number on the mouse used in the experiment. PS represents a D2 whose backbone is modified with PS, PS-OMe represents a D2 whose backbone is PS and in which all nucleotides are modified with O-methyl, and PS-LNA represents a D2 whose backbone is PS and in which all nucleotides are modified with LNA.

Figure 23B:
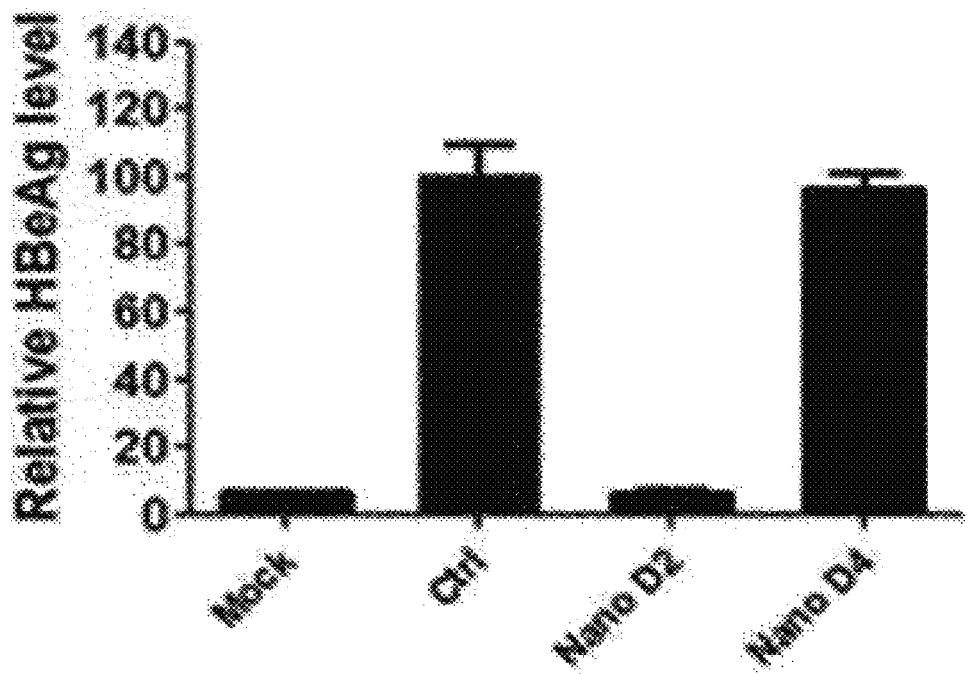
Figure 23C:
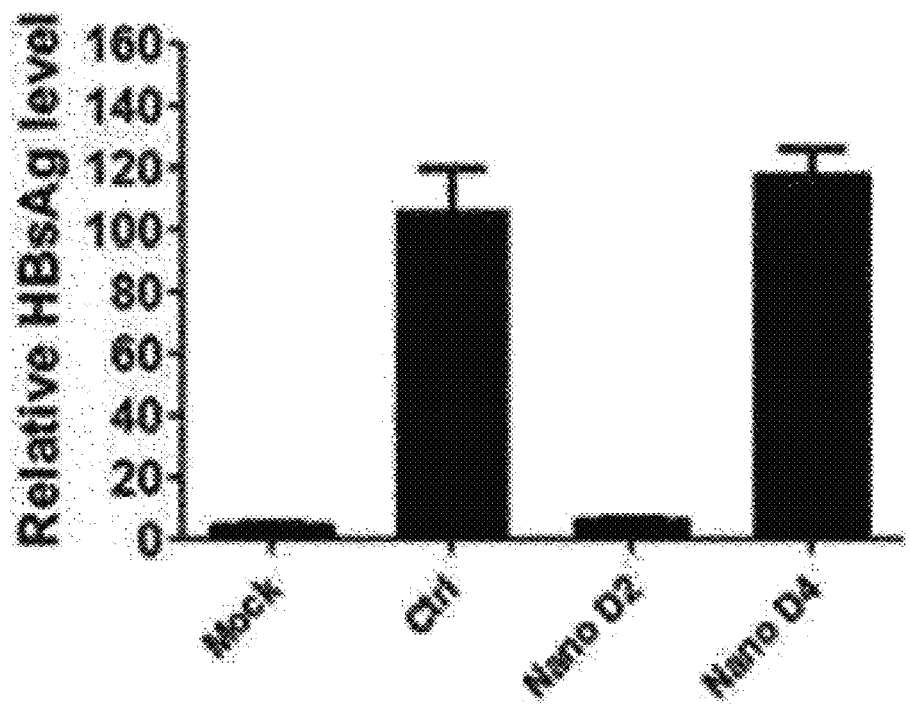
Figure 23D:
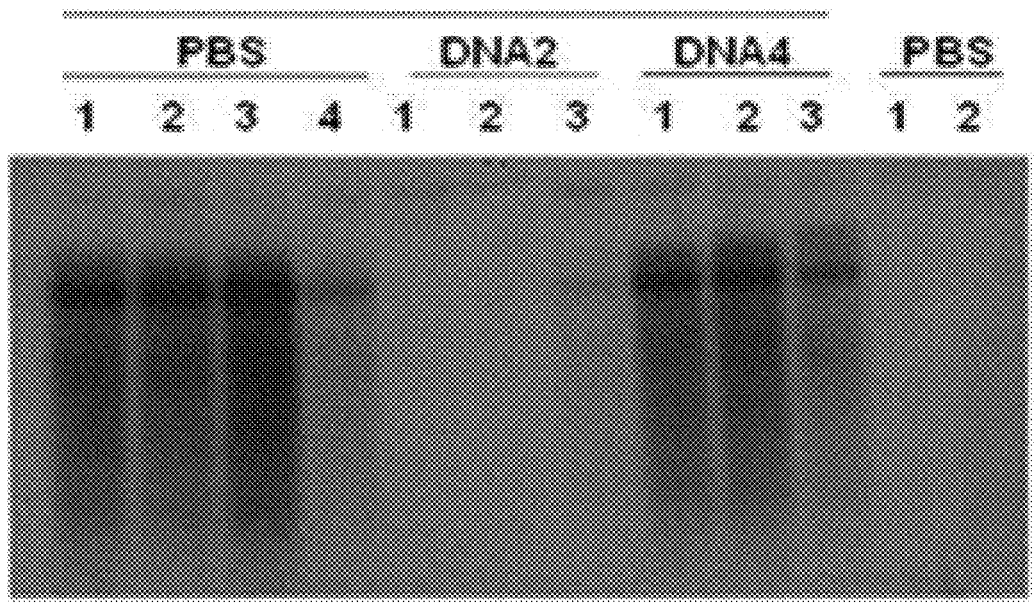

FIGS. 23A-23D show HBV inhibition when the modified oligonucleotides are encapsidated with nanoparticles (chitosan) and then injected intravenously into an in vivo model. FIG. 23A is a schematic illustration of an in vivo intravenous (IV) injection experimental schedule, FIGS. 23B and 23C are the measurement results of viral proteins HBeAg and HBsAg, respectively, and FIG. 23D is the result confirmed by Southern blot.

Figure 24A:
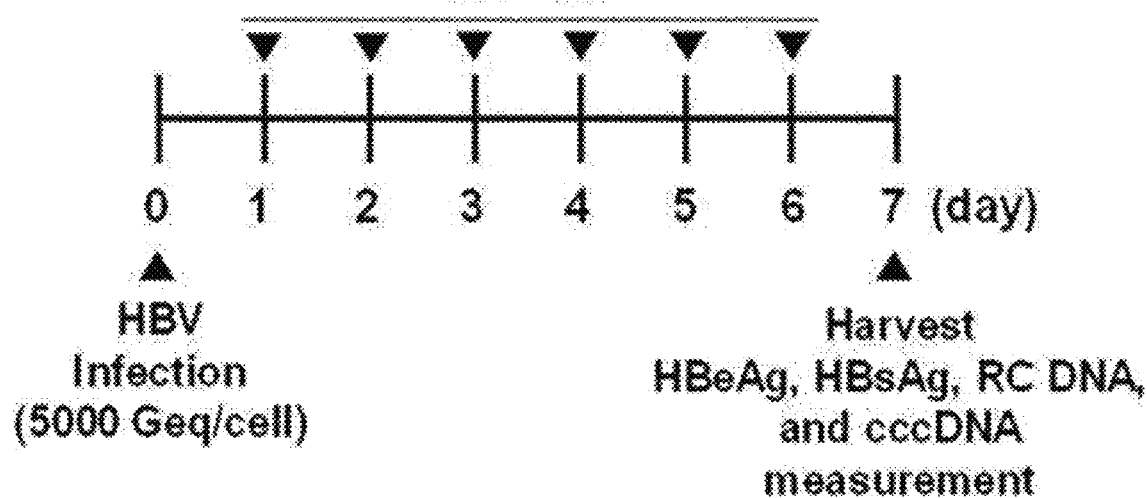
Figure 24D:
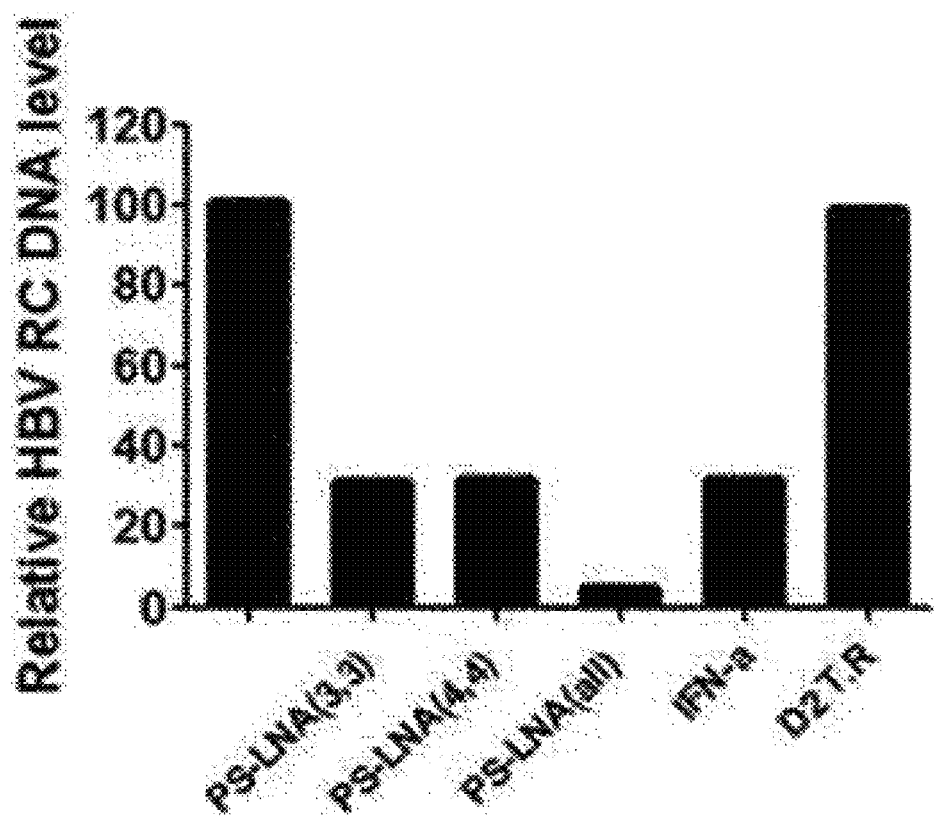
Figure 24E:
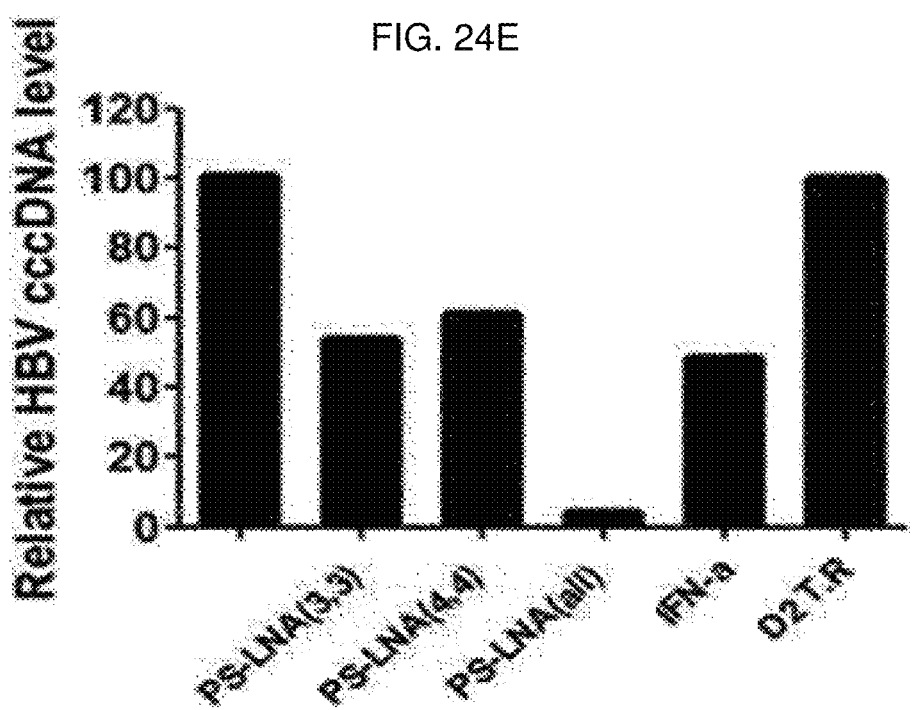

FIGS. 24A-24E show HBV inhibition when cells were treated with the modified oligonucleotides from the beginning. FIG. 24A is a schematic illustration of a procedure for transfecting PHH with HBV, FIGS. 24B and 24C are results of confirming that the modified oligonucleotides have a superior effect of removing cccDNA, and FIGS. 24D and 24E are the results of quantitative evaluation by real-time PCR.

Figure 25A:
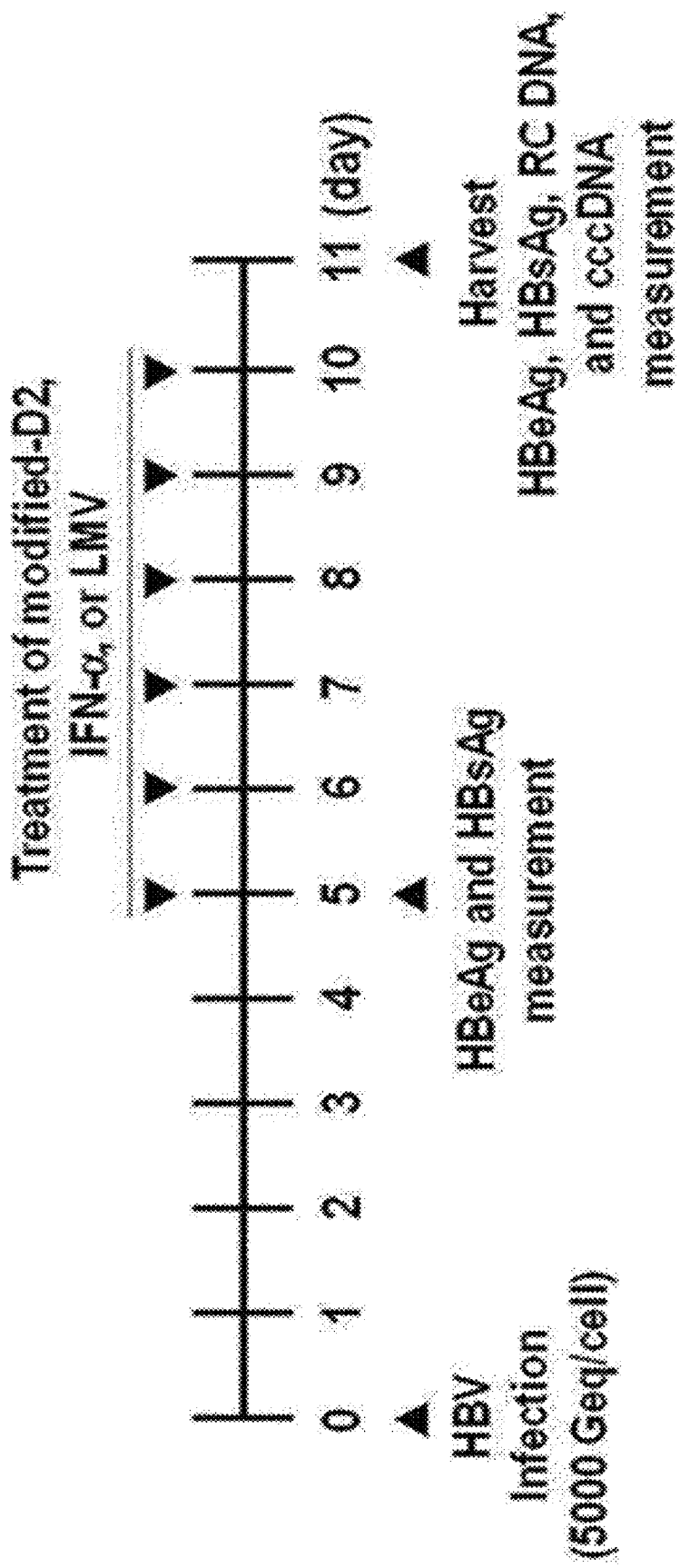
Figure 25C:
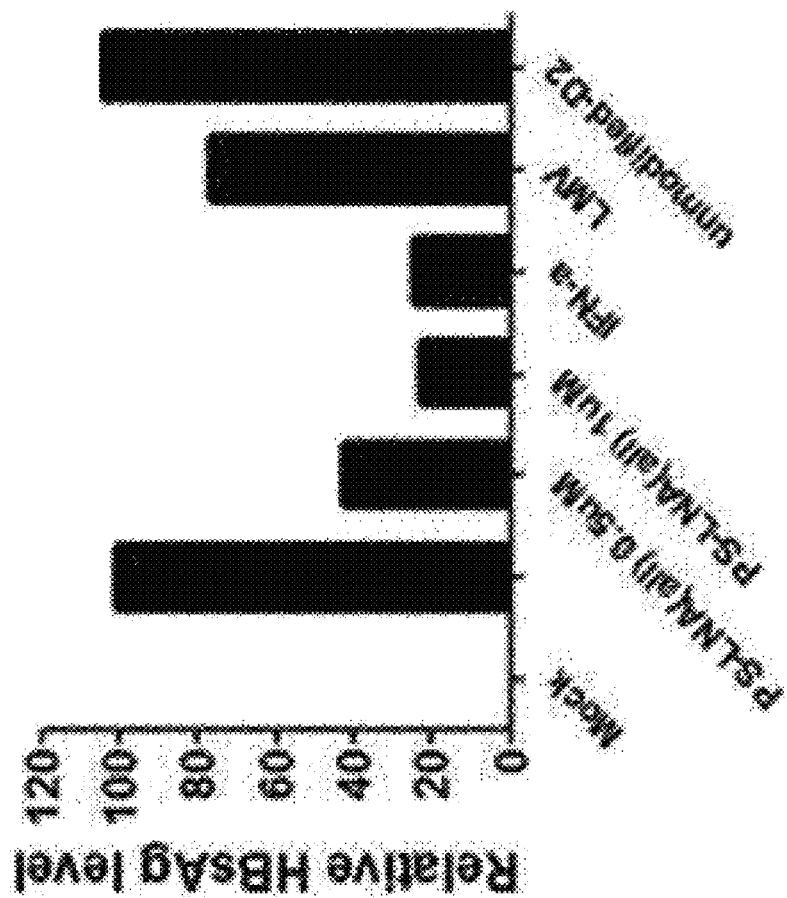
Figure 25B:
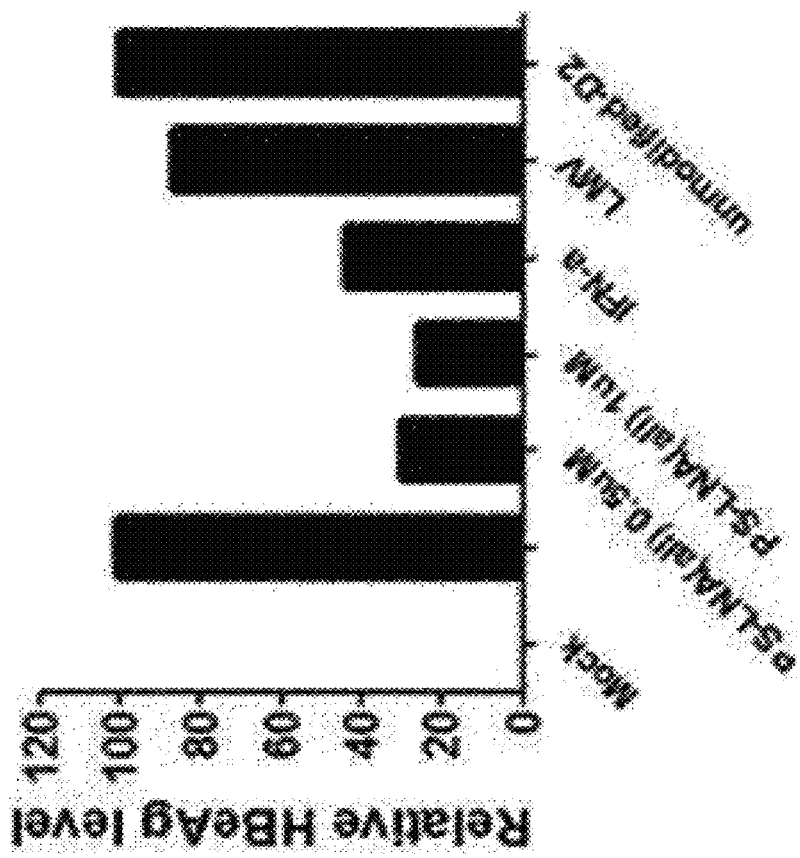

FIGS. 25A-25D show HBV inhibition when cells were treated with the modified oligonucleotides in a re-transfection condition. FIG. 25A is a schematic illustration of a procedure for transfecting PHH with HBV, FIGS. 25B and 25C are the results of treating the modified oligonucleotides at different concentrations, and FIG. 25D is the result of confirming the difference in the amount of DNA through electrophoresis after general PCR.

Figure 26A:
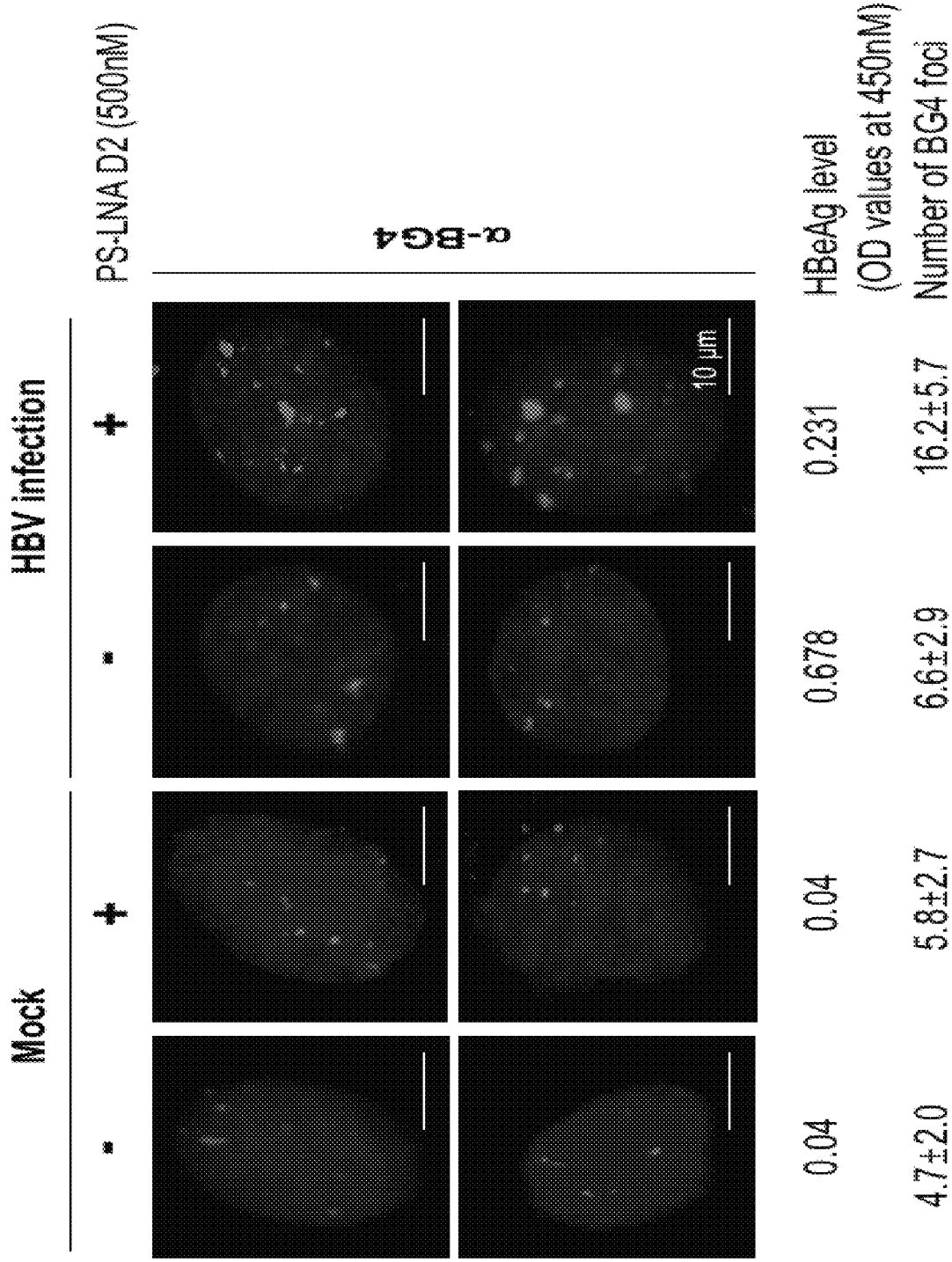
Figure 26B:
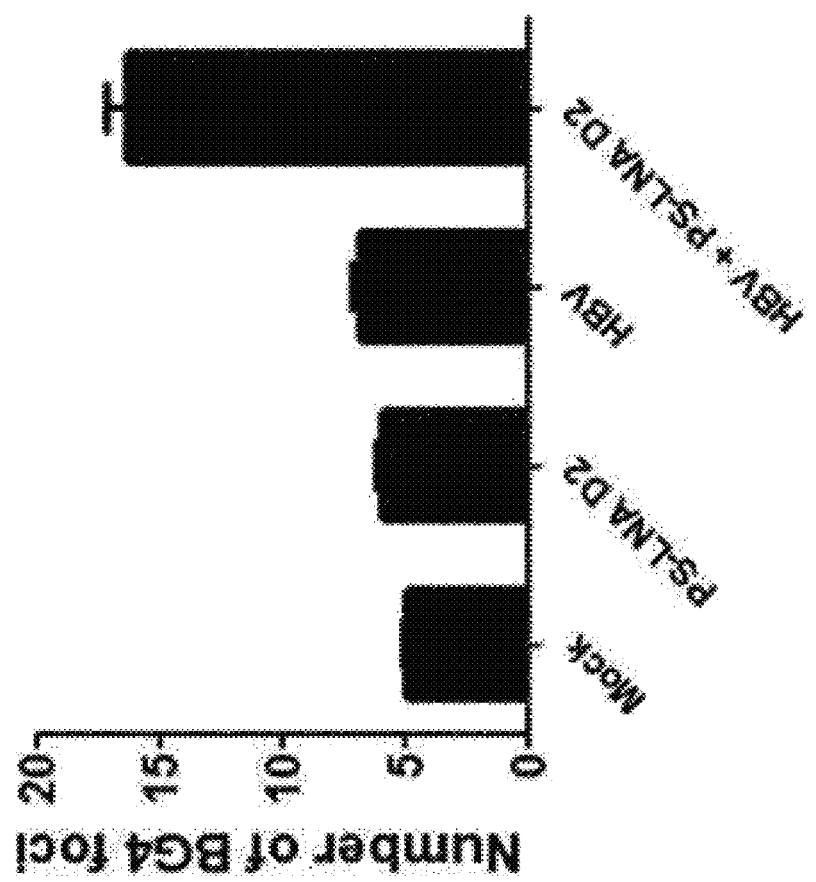

FIGS. 26A-26B show the results of confirming whether the modified oligonucleotides efficiently recognize cccDNA in HepG2-NTCP and form a G-quadruplex. FIG. 26A confirms that D2 and cccDNA formed a G-quadruplex by BG4 antibodies recognizing the G-quadruplex when cells were treated with HBV cccDNA produced by transfection in NTCP and the modified oligonucleotides, and FIG. 26B shows the number of foci by BG4.

DETAILED DESCRIPTION OF EMBODIMENTS

In an embodiment, there is provided a pharmaceutical composition for treating or preventing hepatitis B, including: at least one oligonucleotide selected from the group consisting of an oligonucleotide represented by a nucleic acid sequence of SEQ ID NO: 1, 2, or 6, or a complimentary nucleic acid sequence thereof; and an oligonucleotide having at least one chemical modification on the oligonucleotide, as an active ingredient.

According to Examples below, it was confirmed that the production of HBV protein was inhibited when the oligonucleotide having the nucleic acid sequence of SEQ ID NO: 1, 2, or 6 was treated to an HBV-transfected liver cancer cell line and injected into an HBV mouse model. Thus, it was confirmed that the oligonucleotide having the nucleic acid sequence of SEQ ID NO: 1, 2, or 6 has an antiviral effect against HBV. Therefore, a nucleic acid sequence complementary to the oligonucleotide having the nucleic acid sequence of SEQ ID NO: 1, 2, or 6 may also have an antiviral effect against HBV.

In another embodiment, in order to facilitate cell penetration of oligonucleotides, oligonucleotides having at least one chemical modification on the oligonucleotide represented by the nucleic acid sequence of SEQ ID NO: 1, 2, or 6 were synthesized and treated to an HBV-transfected liver cancer cell line and to an HBV-transfected mouse model. As a result, it was confirmed that the production of HBV protein was inhibited, thereby confirming that the oligonucleotides having at least one chemical modification have an excellent antiviral effect against HBV despite the chemical modification.

Accordingly, one or more oligonucleotides selected from the group consisting of an oligonucleotide represented by a nucleic acid sequence of SEQ ID NO: 1, 2, or 6 or a nucleic acid sequence complementary thereto; and an oligonucleotide having at least one chemical modification on the oligonucleotide may be used as an active ingredient of pharmaceuticals for the treatment or prevention of hepatitis B.

In the pharmaceutical composition, the oligonucleotides having a chemical modification may have at least one chemically modified internucleoside linkage, or at least one chemically modified sugar moiety.

In an embodiment, the oligonucleotide refers to, but is not limited to, a polymer consisting of about 5 to 40, for example, 10 to 13 nucleotides.

A nucleotide is composed of a base, a pentose, and a phosphate group (phosphate). The base may be a purine (adenine or guanine) or a pyrimidine (cytosine, thymine, or uracil). Further, the pentose may be ribose, deoxyribose, arabinose, xylose, lyxose, allose, altose, glucose, mannose, gulose, idose, galactose, talose, or a stabilized modified form of the sugars.

For example, when the pentose is deoxyribose, the nucleotide can be represented by the following Chemical Formula 1.

[Chemical Formula 1]

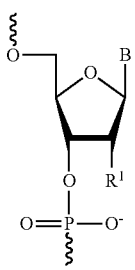

in the Chemical Formula 1,
B is a base, and $R^1$ is —H.

The chemical modification will be described in more detail as follows. The chemically modified oligonucleotides may include various chemical modifications involving internucleoside linkages, ribose units, and/or natural nucleoside bases (adenine, guanine, cytosine, thymine, etc.) as compared to natural oligonucleotides. The modification can occur during or after the synthesis of oligonucleotides. During synthesis, the modified base may be incorporated internally or at its terminus. After synthesis, the modification may be performed using an activating group (via an amino modifier, via a 3' or 5' hydroxyl group, or via a phosphate group). Methods for modifying oligonucleotides are well known to one of ordinary skill in the art.

In some embodiments, the oligonucleotides having a chemical modification may have a chemically modified internucleoside linkage.

The chemical modification of the internucleoside linkage means that the oxygen in the phosphate group linking the nucleosides to one another is replaced by one or more other substituents.

In some embodiments, a stabilized sugar phosphate backbone of a nucleic acid molecule where the oxygen in the phosphate group not participating in the internucleoside linkage is replaced by sulfur is referred to as "phosphorothioate backbone". In addition to the phosphorothioate, the phosphate group of a nucleotide may also be substituted with phosphorodithioate, phosphoramidate, or boranophosphate, but is not limited thereto. The backbone of phosphorothioate, phosphorodithioate, phosphoramidate, or boranophosphate is represented by the following Chemical Formulae 2 to 5, respectively.

[Chemical Formula 2]

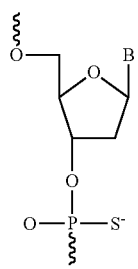

[Chemical Formula 3]

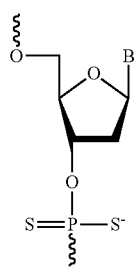

[Chemical Formula 4]

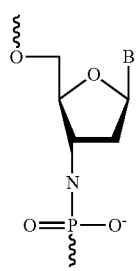

[Chemical Formula 5]

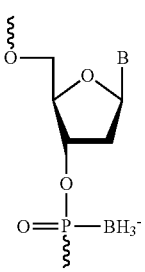

in the Chemical Formulae 2 to 5, B is a base.

In some embodiments, the oligonucleotide having a chemical modification may have at least one chemically modified sugar moiety.

The chemical modification of the sugar moiety means that the pentose in a nucleotide is chemically modified.

The chemical modification of the sugar moiety includes, for example, a substitution of the —H group at the 2' position of the pentose in a nucleotide with another substituent, or a modification in the basic structure of the pentose.

The chemical modification of the sugar moiety in which the —H group at the 2' position of the pentose in the nucleotide is substituted with another substituent means that $R^1$ at the 2' position of the pentose of Chemical Formula 1 below is substituted with another substituent other than —H.

[Chemical Formula 1]

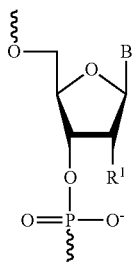

in the Chemical Formula 1,

B is a base, and $R^1$ is —H.

In some embodiments, the sugar moiety is not limited to the —H group at the 2' position of the pentose in the nucleotide, but may be modified by substitution with methoxyethoxy [2'-O—CH$_2$CH$_2$OCH$_3$, 2'-O-(2-methoxyethyl); MOE], Chemical Formula 6), dimethylaminooxyethoxy ([2'-O(CH$_2$)$_2$ON(CH$_3$)$_2$; DMAOE], Chemical Formula 7), dimethylaminoethyloxyethyl ([2'-OCH$_2$CH$_2$—O—CH$_2$CH$_2$—N(CH$_3$)$_2$; DMAEOE], Chemical Formula 8), methoxy ([2'-OCH$_3$; OMe], Chemical Formula 9), aminopropoxy ([2'-OCH$_2$CH$_2$CH$_2$NH$_2$; AP], Chemical Formula 10) or fluoro (2'-F, Chemical Formula 11), or the sugar moiety may be modified by substitution with F-ANA (2'-F-β-D-arabinofuranosyl, Chemical Formula 12).

[Chemical Formula 6]

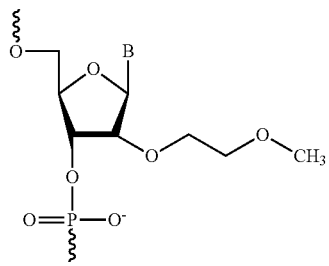

[Chemical Formula 7]

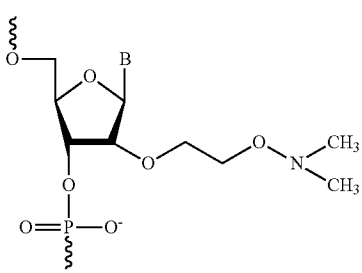

[Chemical Formula 8]

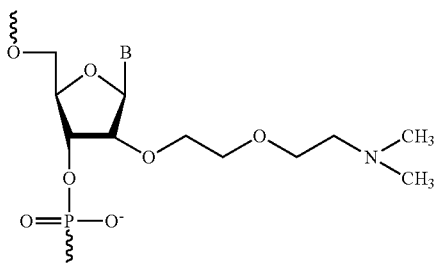

[Chemical Formula 9]

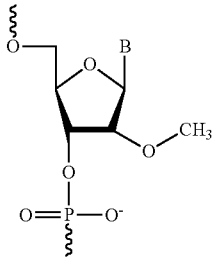

[Chemical Formula 10]

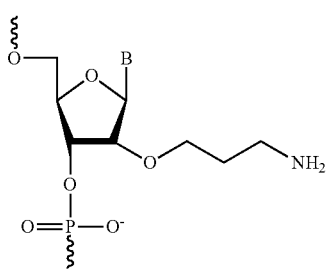

[Chemical Formula 11]

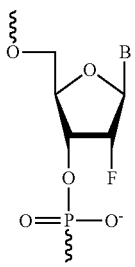

[Chemical Formula 12]

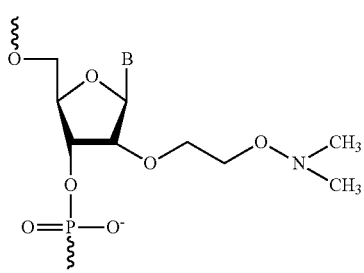

in the Chemical Formulae 6 to 12, B is a base.

In some embodiments, the modification of the basic structure of the pentose in the nucleotide may include a chemical modification of the pentose in the nucleotide in the form of LNA (locked nucleic acid) or PNA (peptide nucleic acid).

LNA (locked nucleic acid) is also known as 'locked nucleic acid' or 'bicyclic nucleoside', and includes a nucleoside including a covalent bridge between 2' position and 4' position of the pentose of the nucleotide. LNA is represented by Chemical Formula 13.

[Chemical Formula 13]

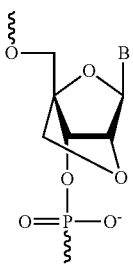

in the Chemical Formula 13, B is a base.

PNA (peptide nucleic acid) is also known as 'peptide nucleic acid', where the base in the basic backbone of the nucleotide is retained, and binds directly or indirectly to an aza-nitrogen atom of an amide in the basic backbone. PNA may be represented by Chemical Formula 14 below.

[Chemical Formula 14]

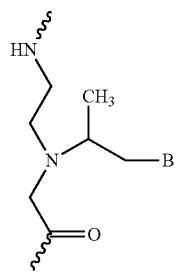

in the Chemical Formula 14, B is a base.

In some embodiments, the oligonucleotide may be in a state where GalNAc (N-acetylgalactosamine) is bound to the 3' or 5' end via a linker.

The GalNAc may be introduced as needed to the linker moiety linked to the end of the oligonucleotide; for example, 1, 2, or 3 units may be introduced, but the GalNAc is not limited thereto.

Since GalNAc binds to the asialoglycoprotein receptor of hepatocytes, techniques enabling a liver specific delivery by binding GalNAc, as a liver targeting moiety, to the ends of oligonucleotides have been developed. Since the oligonucleotides require a liver specific delivery, it is possible to further chemically modify the oligonucleotides utilizing such known GalNAc binding techniques.

In some embodiments, the oligonucleotide having a chemical modification may have at least two chemical modifications selected from the group consisting of a chemical modification of the internucleoside linkage and a chemical modification of the sugar moiety.

The chemical modification of the sugar moiety may be the same or different.

In some embodiments, one or more nucleotides of the oligonucleotide may include a chemical modification of the sugar moiety, and may be bound by an internucleoside linkage having a chemical modification. The chemical modification of one nucleotide is independent of the chemical modification of other nucleotides present within the same oligonucleotide.

In some embodiments, all nucleotides of the oligonucleotide may include a chemical modification of the sugar moiety.

In some embodiments, the oligonucleotide having a chemical modification may be modified from the nucleotide by at least 50%, at least 60%, at least 70%, at least 80%, at least 90%, at least 95%, or 100%.

For example, the oligonucleotide having two or more chemical modifications may be one in which the phosphate group of the nucleotide is chemically modified with phosphorothioate, phosphorodithioate, phosphoramidate, or boranophosphate, and further, the —H group at the 2' position of the pentose in the nucleotide is substituted with methoxyethyl (MOE), dimethylaminooxyethoxy (DMAOE), dimethylaminoethoxyethyl (DMAEOE), methyl (OMe), aminopropoxy (AP), or fluoro (F), or the sugar moiety of the nucleotide is substituted with F-ANA.

In another embodiment, the oligonucleotide having two or more chemical modifications may be one in which the phosphate group of the nucleotide is chemically modified with phosphorothioate, phosphorodithioate, phosphoramidate, or boranophosphate, and further, the sugar moiety is chemically modified in the form of LNA (locked nucleic acid) or PNA (peptide nucleic acid).

In some embodiments, the 5' end of the oligonucleotide may include 1, 2, 3, 4, or 5 contiguous chemical modifications.

In some embodiments, the 3' end of the oligonucleotide may include 1, 2, 3, 4, or 5 contiguous chemical modifications.

In some embodiments, the oligonucleotide may include 1, 2, 3, 4, or 5 contiguous chemical modifications at the 5' and 3' ends.

For example, as can be seen from the following embodiments, the oligonucleotide may be PS-OMe (4,4) in which the entire backbone is modified to a phosphorothioate (PS) backbone and four nucleotides at each of the 5' and 3' ends of the oligonucleotide are replaced with O-methyl; or PS-OMe (5,5) in which 5 nucleotides at the 5' and 3' ends of the oligonucleotide are modified with O-methyl.

In another embodiment, the oligonucleotide may be PS-LNA (2,2) whose entire backbone is phosphorothioate (PS) and in which 2 nucleotides at each of the 5' and 3' ends are modified with LNA; PS-LNA (3,3) in which 3 nucleotides at each of the 5' and 3' ends are modified with LNA; PS-LNA (4,4) in which 4 nucleotides at each of the 5' and 3' ends are modified with LNA; or PS-LNA (5,5) in which 5 nucleotides at each of the 5' and 3' ends are modified with LNA.

In some embodiments, the oligonucleotide may include an oligonucleotide represented by a nucleic acid sequence of SEQ ID NO: 1, or an oligonucleotide complementary thereto.

In some embodiments, the oligonucleotide may include an oligonucleotide represented by a nucleic acid sequence of SEQ ID NO: 2, or an oligonucleotide complementary thereto.

In some embodiments, the oligonucleotide may include an oligonucleotide represented by a nucleic acid sequence of SEQ ID NO: 6, or an oligonucleotide complementary thereto.

In an embodiment, the oligonucleotides represented by the nucleic acid sequences of SEQ ID NOs: 20 to 57 were used as the oligonucleotides having the chemical modifications, but are not limited thereto.

In some embodiments, the oligonucleotide can form a G-quadruplex with HBV.

In the double helix DNA according to the Watson-Crick model, adenine pairs with thymine and guanine pairs with cytosine by hydrogen bonds. However, according to Hoogsteen, four guanines in guanine-rich regions are held together by hydrogen bonds in a plane to form a quartet, and three quartets are vertically stacked to form a structure, which has been proposed as a G-quadruplex. In general, it has been reported that guanines exist as G-quadruplex structures in a gene having many guanine-rich regions.

In some embodiments, it was confirmed that the oligonucleotide binds to HBV to form a G-quadruplex, thereby inhibiting HBV activity (see Example 3).

The oligonucleotides may be used to inhibit the expression of HBV in individuals, such as cells, tissues, etc.

In some embodiments, a composition, i.e., a pharmaceutical composition may be formulated for administration to an individual using the oligonucleotide. The formulation may include a pharmaceutically acceptable excipient. Pharmaceutically acceptable excipients are substances from which active pharmaceutical ingredients (e.g., oligonucleotides, therapeutic agents, etc.) are excluded. Excipients do not exhibit an effect at added doses.

In an embodiment, there is provided a pharmaceutical composition for treating or preventing hepatitis B including at least one of the oligonucleotides.

The oligonucleotide may be described as an "antiviral oligonucleotide" or "anti-HBV oligonucleotide".

In some embodiments, the pharmaceutical composition for treating or preventing hepatitis B may inhibit HBV activity by reducing cccDNA (covalently closed circular DNA) of HBV.

Therefore, there is provided a pharmaceutical composition including the "antiviral oligonucleotide".

The pharmaceutical composition may include the oligonucleotide or oligonucleotides, and contain other materials that do not interfere with use as an antiviral agent in vivo. Such other materials may include, but are not limited to, diluents, excipients, carrier materials, and/or other antiviral materials.

In an embodiment, the oligonucleotides may be formulated as various pharmaceutical compositions. Pharmaceutical compositions will be prepared in a form appropriate for the intended use. In general, preparation of compositions that are essentially free of pyrogens, as well as other impurities that could be harmful to humans or animals will be needed. Exemplary delivery/formulation systems include chitosan nanoparticles, colloidal dispersion systems, macromolecule complexes, nanocapsules, nanoparticles, microspheres, beads, and lipid-based systems including oil-in-water emulsions, micelles, mixed micelles, and liposomes.

In some embodiments, the pharmaceutically acceptable carrier may be a chitosan nanoparticle, and the chitosan may have a molecular weight of 50 kDa to 190 kDa.

The composition or formulation may employ a plurality of therapeutic oligonucleotides, including at least one described herein. For example, the composition or formulation may employ at least 1, 2, or 3 antiviral oligonucleotides described herein.

In some embodiment, the oligonucleotide may be used in combination with other therapeutic agents. The combinations may also be achieved by contacting the cell with one or more distinct compositions or formulations at the same time. Alternatively, the combinations may be administered sequentially.

In some embodiments, the oligonucleotide may be formulated for conventional subcutaneous or intravenous administration, for example, by formulating with an appropriate aqueous diluent, including sterile water and normal saline.

The pharmaceutical composition and formulation may employ appropriate salts and buffers to render delivery vehicles stable and allow for uptake by target cells. In an embodiment, the pharmaceutical composition includes an effective amount of the delivery vehicle including an inhibitor oligonucleotide (e.g., liposomes, nanoparticles, or other complexes), and is dissolved or dispersed in a pharmaceutically acceptable carrier or aqueous medium. The "pharmaceutically acceptable" or "pharmacologically acceptable" refers to a molecular entity or composition that does not produce adverse, allergic, or other untoward reactions when administered to an animal or a human.

As used herein, the "pharmaceutically acceptable carrier" may include one or more solvents, buffers, solutions, dispersion media, coatings, antibacterial and antifungal agents, isotonic and absorption delaying agents, etc., acceptable for use in formulating pharmaceuticals, such as pharmaceuticals suitable for administration to humans. The use of such media and agents for pharmaceutically active substances is well known in the art. Supplementary active ingredients may also be incorporated into the composition.

Administration or delivery of the pharmaceutical composition may be via any route so long as the target tissue is available via the same route. For example, the administration may be topical or by intradermal, subcutaneous, intramuscular, intraperitoneal, intraarterial, intracoronary, intrathecal, or intravenous injection, or by direct injection into a target tissue (e.g., cardiac tissue). The stability and/or potency of the oligonucleotides disclosed herein allows for convenient routes of administration, including subcutaneous, intradermal, intravenous, and intramuscular routes. Further, the pharmaceutical composition including the oligonucleotides described herein may be administered by catheter systems or systems that isolate coronary circulation for delivering therapeutic agents to the heart. Various catheter systems for delivering therapeutic agents to the heart and coronary vasculature are known in the art.

The oligonucleotide and the pharmaceutical composition may be contained in a kit, a container, a pack, or a dispenser.

In some embodiments, the pharmaceutical composition including at least one of the oligonucleotides is effective in inhibiting HBV expression in cells, tissues, or individuals. In addition, the composition or formulation may also be administered parenterally, intraperitoneally, intravenously, percutaneously, sublingually, intramuscularly, intranasally, or subcutaneously. For example, solutions of the conjugates as free bases or pharmacologically acceptable salts may be prepared in water suitably mixed with a surfactant, such as hydroxypropylcellulose. Dispersions may also be prepared in glycerol, liquid polyethylene glycols, and mixtures thereof and in oils.

Under ordinary conditions of storage and use, these preparations generally contain a preservative to prevent the growth of microorganisms. The pharmaceutical forms suitable for injectable use or catheter delivery include, for example, sterile aqueous solutions or dispersions and sterile powders for extemporaneous preparations of sterile injectable solutions or dispersions. In general, these preparations are sterile and fluid to the extent that easy injectability exists. Preparations should be stable under the conditions of manufacture and storage, and should be preserved against the contaminating action of microorganisms, such as bacteria and fungi. Appropriate solvents or dispersion media may contain, for example, water, ethanol, polyols (e.g., glycerol, propylene glycol, liquid polyethylene glycol, etc.), suitable mixtures thereof, and vegetable oils. The proper fluidity may be maintained, for example, by the use of a coating, such as lecithin, by the maintenance of the required particle size in the case of dispersion and by the use of surfactants. The prevention of the action of microorganisms may be achieved by various antibacterial and antifungal agents, for example, parabens, chlorobutanol, phenol, sorbic acid, thimerosal, etc. In many cases, it may be preferable to include isotonic agents, for example, sugars or sodium chloride. Prolonged absorption of the injectable compositions may be achieved by the use of absorption delaying agents, for example, aluminum monostearate and gelatin, in the composition.

Sterile injectable solutions may be prepared by incorporating appropriate amounts of conjugates into a solvent along with any other ingredients (e.g., as enumerated above) as desired. In general, dispersions are prepared by incorporating various sterilized active ingredients into a sterile vehicle which contains the basic dispersion medium and other desired ingredients, e.g., as enumerated above. In the case of sterile powders for the preparation of sterile injectable solutions, the preferred preparation methods include vacuum-drying and freeze-drying techniques which yield a powder of the active ingredients added with any additional desired ingredient from a previously sterile-filtered solution thereof.

Upon formulation, solutions are preferably administered in a manner compatible with the dosage formulation and in such amount as is therapeutically effective. The formulations may easily be administered in a variety of dosage forms such as injectable solutions, drug release capsules, etc. For parenteral administration in an aqueous solution, for example, the solution is generally suitably buffered, and the liquid diluent is first rendered isotonic, for example, with sufficient saline or glucose. Such aqueous solutions may be used, for example, for intravenous, intramuscular, subcutaneous, and intraperitoneal administration. Preferably, sterile aqueous media are employed as is known to those of skill in the art, particularly in light of the present disclosure. For example, a single dose may be dissolved in 1 ml of isotonic NaCl solution and either added to 1000 ml of hypodermoclysis fluid or injected at the proposed site of infusion (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for administration to humans, preparations should meet sterility, pyrogenicity, general safety, and purity standards as required by the FDA Office of Biologics standards.

In an embodiment, there is provided a method for delivering oligonucleotides to a cell (e.g., as part of the composition or formulation described herein), and a method for treating, ameliorating, or preventing the progression of a condition in a subject. As used herein, the term "subject" or "patient" refers to any vertebrate including, without limitation, humans and other primates (e.g., chimpanzees and other apes and monkey species), farm animals (e.g., cattle, sheep, pigs, goats, and horses), domestic mammals (e.g., dogs and cats), laboratory animals (e.g., rodents such as mice, rats, and guinea pigs), and birds (e.g., domestic, wild, and game birds such as chickens, turkeys, and other gallinaceous birds, ducks, geese, etc.). In some embodiments, the subject is a mammal.

In other embodiments, the mammal is a human.

In an embodiment, the oligonucleotide or pharmaceutical composition may be contacted with a target cell in vitro or in vivo (e.g., a mammalian cell). In some embodiments, the cell may be a liver cell.

Further, in an embodiment, there is provided a method for screening a therapeutic agent for hepatitis B, including contacting hepatitis B virus (HBV) with a candidate material, and confirming whether the HBV forms a G-quadruplex with the candidate material.

In the screening method, it can be judged that the candidate material is effective in treating hepatitis B when the HBV forms a G-quadruplex with the candidate material.

In an embodiment, the formation of a G-quadruplex by HBV and the candidate material may be confirmed by electrophoretic mobility shift assay (EMSA), circular dichroism (CD), nuclear magnetic resonance (NMR), or a method of using G-quadruplex-specific antibodies, but any method capable of confirming the binding between DNA and protein may be used without limitation.

The candidate material may include four or more guanines (G). As the candidate material includes four or more guanines, a G-quadruplex, in which four helices form a single structure based on four guanine bonds, may be formed.

The G-quadruplex may be formed by binding an enhancer II region of HBV with a candidate material. The enhancer II may have a nucleic acid sequence of SEQ ID NO: 19.

In the following Examples, it was confirmed that the oligonucleotide having a nucleic acid sequence of SEQ ID NO: 2 physically binds to the enhancer II region of HBV to partially form a G-quadruplex, thereby inhibiting the HBV enhancer activity.

In some embodiments, the candidate material may be an oligonucleotide represented by a nucleic acid sequence of SEQ ID NO: 1, 2, or 6, or a complementary nucleic acid sequence thereof, or an oligonucleotide having at least one chemical modification on the oligonucleotide, or may include both oligonucleotides.

The aforementioned description of the oligonucleotides may be directly applied thereto.

In some embodiments, there is provided a method for treating or preventing hepatitis B, including administering the pharmaceutical composition for treating or preventing hepatitis B orally or parenterally to an individual.

For clinical use, the oligonucleotides may be administered alone via any suitable administration route effective to achieve a desired therapeutic result or may be formulated into a pharmaceutical composition. The administration "route" of the oligonucleotides may include enteral, parenteral, and topical administration or inhalation. The enteral administration route of the oligonucleotides includes oral, gastrointestinal, intestinal, and rectal routes. Parenteral routes include intravenous, intraperitoneal, intramuscular, intraspinal, subcutaneous, topical injection, vaginal, topical, nasal, mucosal, and pulmonary administrations. The topical administration route of the oligonucleotides refers to external application of the oligonucleotides into the epidermis, mouth and ears, eyes, and nose.

As used herein, the term "prevention" refers to all actions that suppress or delay an inflammatory disease or immune disease by the administration of a pharmaceutical composition to an individual.

As used herein, the term "treatment" refers to all actions that alleviate or beneficially change the symptoms of hepatitis by the administration of a pharmaceutical composition to an individual suspected of having hepatitis B.

As used herein, the term "improvement" refers to all actions that at least reduce a parameter related to the condition to be treated, for example, the degree of a symptom.

The present invention is further illustrated by the following additional Examples that should not be construed as limiting. One of ordinary skill in the art should, in light of the present invention, appreciate that many changes can be made to the specific embodiments which are disclosed herein and still obtain a like or similar result without departing from the spirit and scope of the invention.

Unless otherwise defined, all technical and scientific terms used herein have the same meaning as commonly understood by one of ordinary skill in the technical field to which the present invention belongs. In general, the nomenclature used herein are well known and commonly used in the art.

Hereinafter, the present invention will be described in detail by way of Examples. However, these Examples are given for illustrative purposes only, and the scope of the invention is not intended to be limited by these Examples.

Example 1: Materials and Methods 1-1: Cell Culture and Transfection

Human liver cancer cell lines (HepG2 and Huh7 cells) were obtained from the American Type Culture Collection (Manassas, Va., USA). Plasmids capable of expressing the *Homo sapiens* solute carrier family 10 (sodium/bile acid cotransporter) or member 1 (SLC10A1) with the NCBI number of hNTCP [NM_003049.3] were transfected to HepG2 cells using Lipofectamine 2000 (Invitrogen) according to the manufacturer's instructions, in order to establish the HepG2-hNTCP cell lines. The cell lines were cultured in DMEM. DMEM was supplemented with 10% (v/v) FBS (Gibco BRL) and added with 1% penicillin and 1% streptomycin to be used. The HepG2 and Huh7 cells were cultured at 37° C. in an incubator which generates 5% $CO_2$. Primary human hepatocytes (PHHs) were isolated from the liver tissue of a patient from the Catholic University Hospital (Uijeongbu, Gyeonggi-do, Korea) with the approval of the IRB, and used. Primary maintenance media (Gibco BRL, Oregon, USA) were supplemented with CM4000 (Thermo, Rockford, USA) and added with 1% penicillin and 1% streptomycin, and PHHs were cultured therein. Transfection was performed when 80% of the cells were cultured using Lipofectamine 2000 according to the guidelines. After 15 hours of the transfection, the cells were replaced with fresh media. The cells were harvested 2 or 3 days after the transfection.

1-2. HBV Transfection Studies

In order to collect inoculable HBV, a culture supernatant of HepAD38 cells concentrated by approximately 100-fold was precipitated with 6% PEG8000. HBV particles were prepared in PBS containing 25% FBS. Infectious HBV stocks were stored at −80° C. HBV quantification was calculated using a dot blot assay. For HBV transfection, HepG2-NTCP cells and PHH cells were used together with PMM containing 4% PEG and 2.5% DMSO. After 15 hours of the transfection, the media were replaced with fresh PMM. The transfected cells were harvested 7 days after the transfection.

1-3. Southern Blot

Viral DNA was detected by Southern blot. Briefly, cell pellets were harvested by scraping 3 days after of the transfection. Then, the harvested cells were dissolved in 100 μl of cold HEPES (10 mM HEPES pH 7.5, 100 mM NaCl, 1 mM EDTA, 0.5% NP-40) buffer, and HBV core capsids in the lysate were precipitated with 26% PEG8000 buffer. Subsequently, the HBV core capsids were degraded with 0.5% SDS buffer (with 250 mg Proteinase K) for 3 hours at 37° C. HBV DNA was extracted with phenol-chloroform and precipitated with NaOAc and ethanol. Total DNA was separated by electrophoresis in 0.8% agarose gel at 90 V for 3 hours and transferred to an XL nitrocellulose membrane (GE Healthcare). Then, the HBV DNA was detected with a highly pure randomized HBV probe, and the relative HBV DNA replication level was quantified using a phospho-imager.

1-4. Northern Blot

HBV mRNA was detected by Northern blot. Briefly, total cell RNA was extracted using the TRIzol reagent (Invitrogen) according to the manufacturer's protocol. 20 μl of total RNA was separated by electrophoresis in a 1% formaldehyde agarose gel at 120 V for 3 hours and transferred to an XL nitrocellulose membrane (GE Healthcare) for 16 to 18 hours. In order to detect HBV-specific mRNA, the membrane was hybridized with a highly pure randomly primed HBV probe, and the relative HBV DNA replication level was quantified using a phospho-imager.

1-5: Western Blot

After 2 days of the transfection, the cells were harvested and lysed in RIPA buffer [20 mM Tris/HCl, 1% NP-40, 0.5% protease inhibitor cocktail (Sigma, St. Louis, Mo.), 150 mM NaCl, 2 mM KCl, pH 7.4] for 30 minutes at 4° C. Protein lysates were separated by SDS-PAGE. After the SDS-PAGE, proteins of polyacrylamide gel were transferred to a PVDF membrane. Antibodies were used at a ratio of 1:2000. Anti-actin (Sigma), HBsAg (Abcam) and HBcAg (DAKO, USA) were used as primary antibodies ($1^{st}$ antibodies).

1-6: Quantitative Analysis of rcDNA and cccDNA Using Real-Time PCR

In order to quantify HBV rcDNA, whole cellular DNA was extracted from PHH transfected with HBV using a QIAamp DNA Mini kit (Qiagen). Before amplifying cccDNA, DNA was treated with T5 exonuclease (NEB). Real-time PCR was carried out using 20 μl of LightCycler (roche) containing 20 ng of DNA, 0.5 μmol/L of forward and reverse primers, 0.2 μmol/L of a 3'-fluorescein (FL)-labeled probe, and 0.4 μmol/L of a 5'-Red640(R640)-labeled probe. The forward and reverse primers for the amplification of cccDNA have the structures of 5'-CTCCCCGTCTGTGCCTTCT-3' (SEQ ID NO: 10) and 5'-GCCCCAAAGCCACCCAAG-3'(SEQ ID NO: 11), respectively, and the forward and reverse primers of 5'-CTCGTGGTGGACTTCTCTC-3' (SEQ ID NO: 12) and 5'-CTGCAGGATGAAGAGGAA-3' (SEQ ID NO: 13) were used, respectively, for rcDNA amplification in the liver.

For FRET hybridization probes, the forward and reverse primers of 5'-GTTCACGGTGGTCTCCATGCAACGT-FL-3' (SEQ ID NO: 14) and 5'-R640-AGGT-GAAGCGAAGTGCACACGGACC-3' (SEQ ID NO: 15) were used, respectively, for the amplification of cccDNA, and the forward and reverse primers of 5'-CACTCAC-CAACCTCCTGTCCTCCAA-FL-3' (SEQ ID NO: 16) and 5'-R640 TGTCCTGGTTATCGCTGGATGTGTCT-3' (SEQ ID NO: 17) were used, respectively, for the amplification of rcDNA. Amplification of the total amount of HBV DNA was carried out as follows: DNA was treated at 95° C. for 10 minutes, and then treated at 95° C. for 10 seconds, at 58° C. for 10 seconds, and at 72° C. for 15 seconds, and this cycle was repeated 45 times. Amplification of cccDNA was carried out as follows: cccDNA was treated at 95° C. for 10 minutes, and then treated at 95° C. for 10 seconds, at 58° C. for 5 seconds, and at 72° C. for 20 seconds, and this cycle was repeated 45 times. For normalization, beta-globin genes were amplified using a LightCycler beta-Globin control kit (Roche). A plasmid containing an HBV monomer (pHBVEcoRI) was diluted stepwise and used as a quantitative standard.

1-7: Analysis of Luciferase Reporter

Figure 5A:
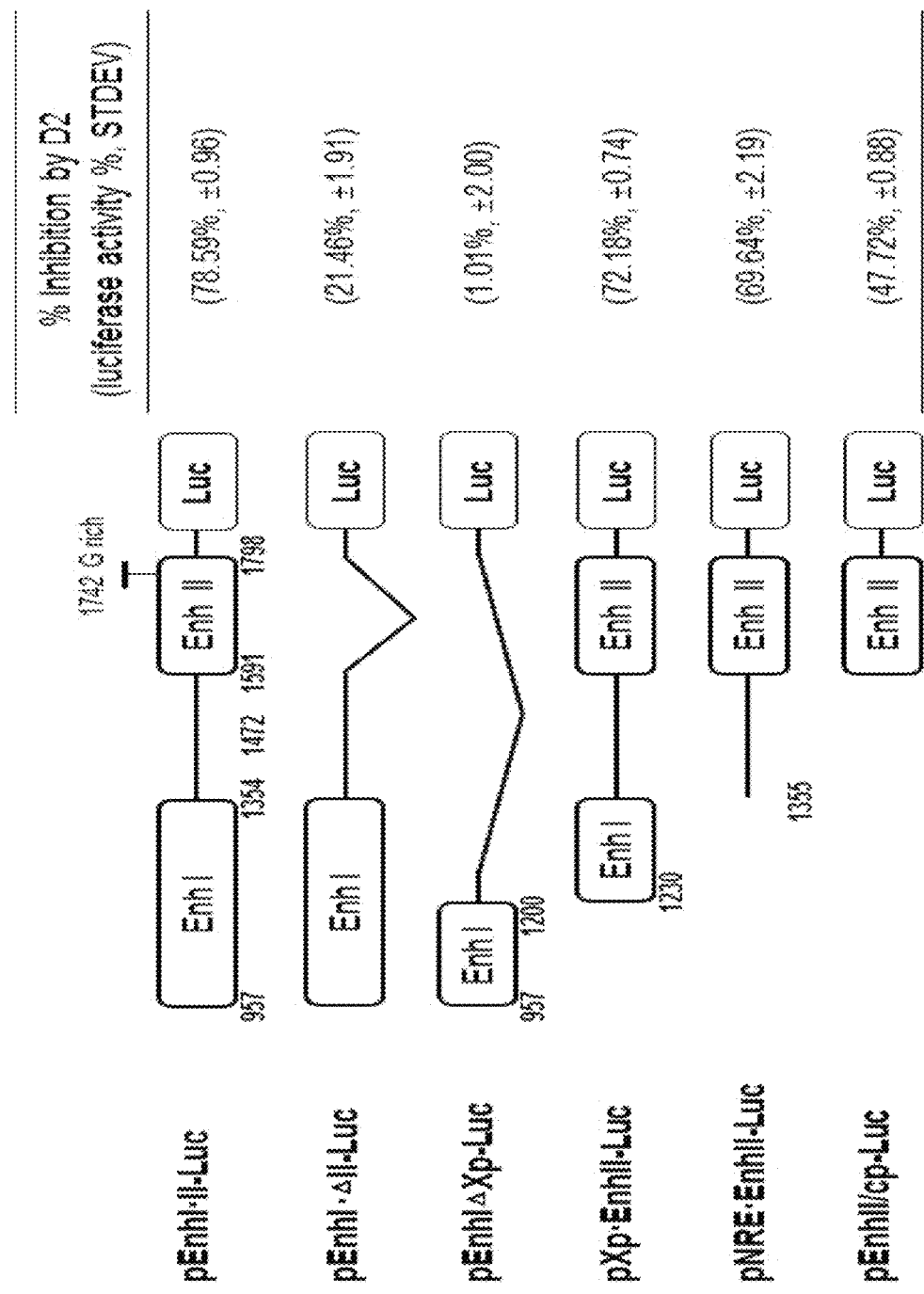
FIGS. 5A and 5B show the results of luciferase reporter assay, illustrating that the oligonucleotides inhibit the HBV enhancer activity.
Figure 5B:
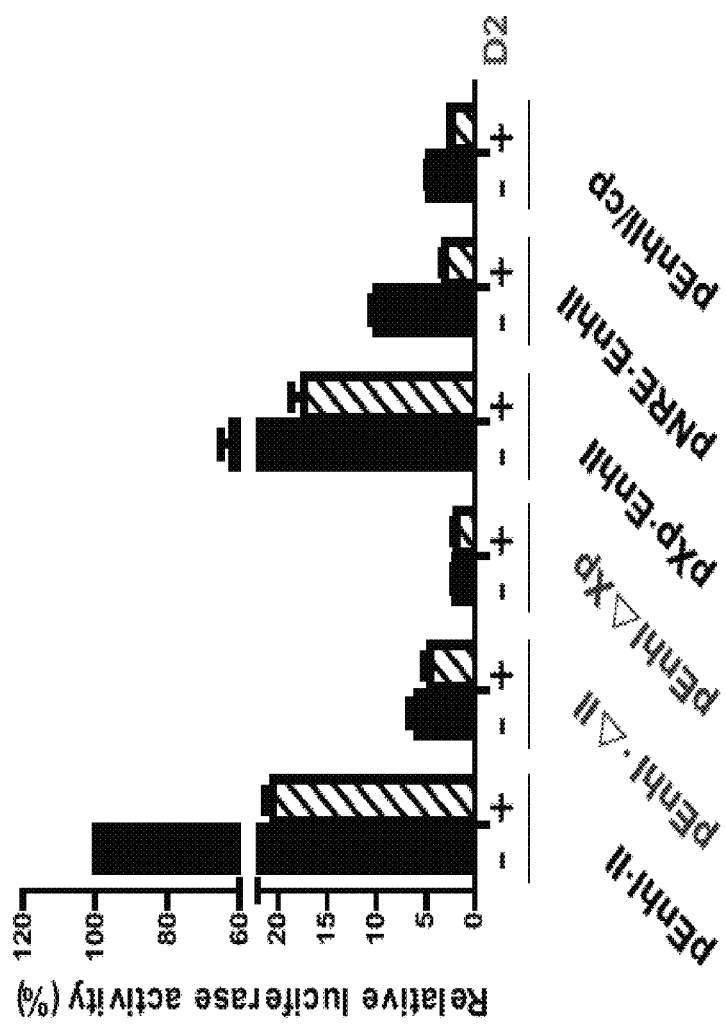
Figure 6A:
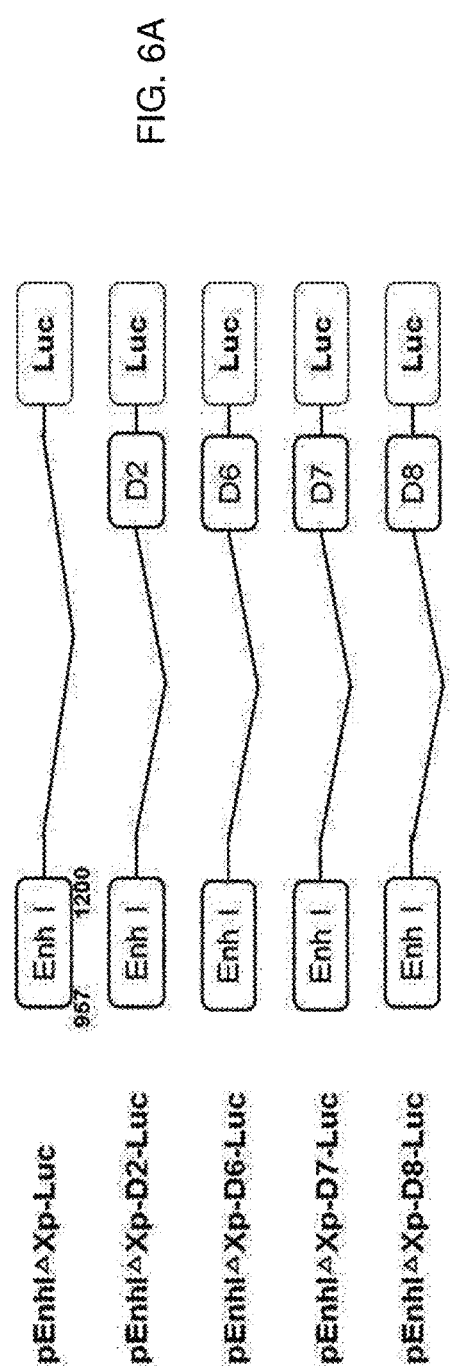
FIGS. 6A and 6B show that the oligonucleotides inhibit the HBV enhancer.
Figure 6B:
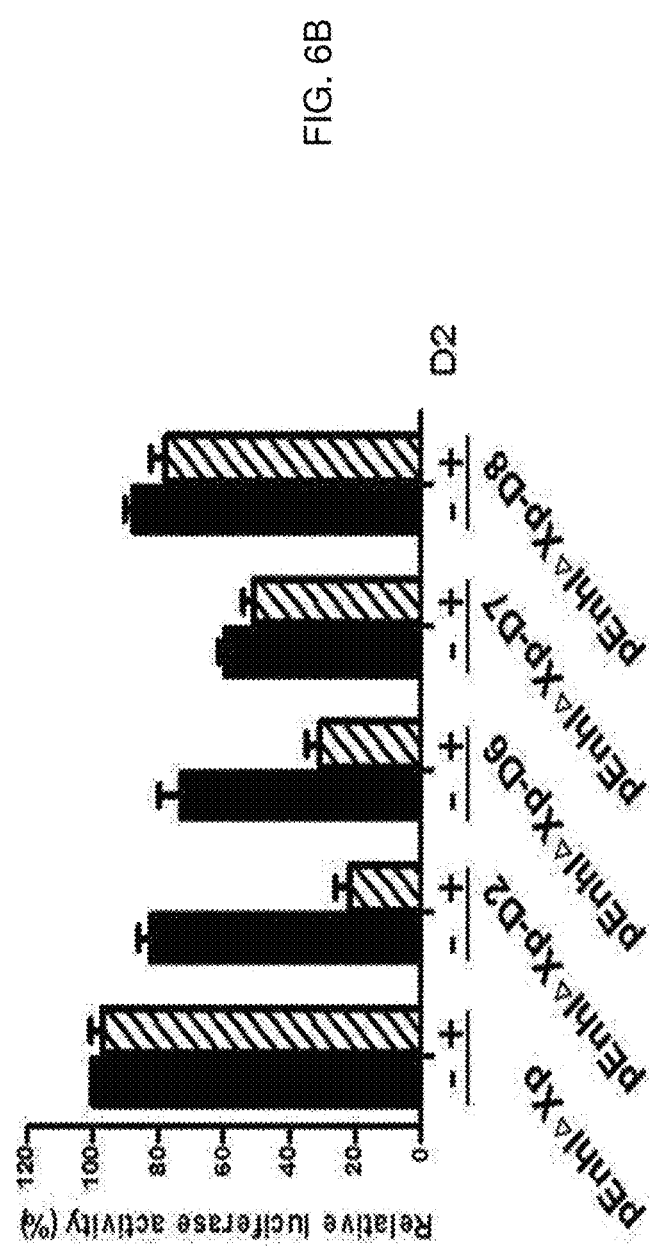

An enhancer luciferase assay was performed to confirm the HBV enhancer activity. 2×10⁵ HepG2 cell lines were prepared in a 12-well plate and transfected with 0.5 µg of Enhancer-Luc (pEnhI.II, pEnhI.ΔII, pEnhIXp, pXp.EnhII, pNRE.EnhII, pEnhII/cp, pEnhIΔXp-D2, pEnhIXp-D6, pEnhIΔXp-D7, and pEnhIXp-D8; see FIGS. 5 and 6) and 50 nM of D2. After 48 hours of the transfection, the cells were harvested and lysed in Promega lysis buffer, and then the enhancer luciferase activity was measured using a luciferase reagent (Promega, Madison, Wis.).

D1 to D9 are non-modified oligonucleotides. Among them, D2 was modified with PS (phosphorothioate), OMe (O-methyl), PNA (peptide nucleic acid), LNA (locked nucleic acid), PS-OMe, and PS-LNA to be used.

The oligonucleotides modified with PS can easily penetrate into cells and prevent degradation by an exonuclease. The oligonucleotides modified with OMe have similar characteristics to RNA but are characterized by increased stability against nuclease and hydrolysis in the cell. In addition, the $T_m$ of the double structure is increased by about 1° C. to 4° C. PNA is an artificially produced polymer, which has a structure similar to DNA or RNA, and its backbone has N-(2-aminoethyl)-glycine repeatedly linked by peptide bonds. The oligonucleotides modified with LNA have a structure in which 2'-oxygen and 4'-carbon are linked and locked, whose $T_m$ increases during hybridization, and are

TABLE 1

| Name | SEQ ID NO: | Sequence (5'-3') |
|---|---|---|
| Enhancer I (957-1354) | 18 | aaattgcct gtaaatagac ctattgattg gaaagtatgt caaagaattg tgggtctttt gggctttgct gcccctttta cacaatgtgg ctatcctgct ttgatgcctt tatatgcatg tatacaatct aagcaggctt tcactttctc gccaacttac aaggcctttc tgtgtaaaca atatctgcac cttttacccg ttgcccggca acggtcaggt ctctgccaag tgtttgctga cgcaacccc actggatggg gcttggccat tggccatcgg cgcatgcgtg gaacctttgt ggctcctctg ccgatccata ccgcggaact cctagcggct tgttttgctc gcagccggtc tggagcgaaa cttatcggga ctgacaactc tgttgtcct |
| Enhancer II (1591-1802) | 19 | cgct tcacctctgc acgtcgcatg gagaccaccg tgaacgccca ccaggtcttg cccaaggtct tacataagag gactcttgga ctctcagcaa tgtcaacgac cgaccttgag gcatacttca aagactgttt gtttaaagac tgggaggagt tggggagga gattaggtta aaggtctttg tattaggagg ctgtaggcat aaattggt |

Figure 1:
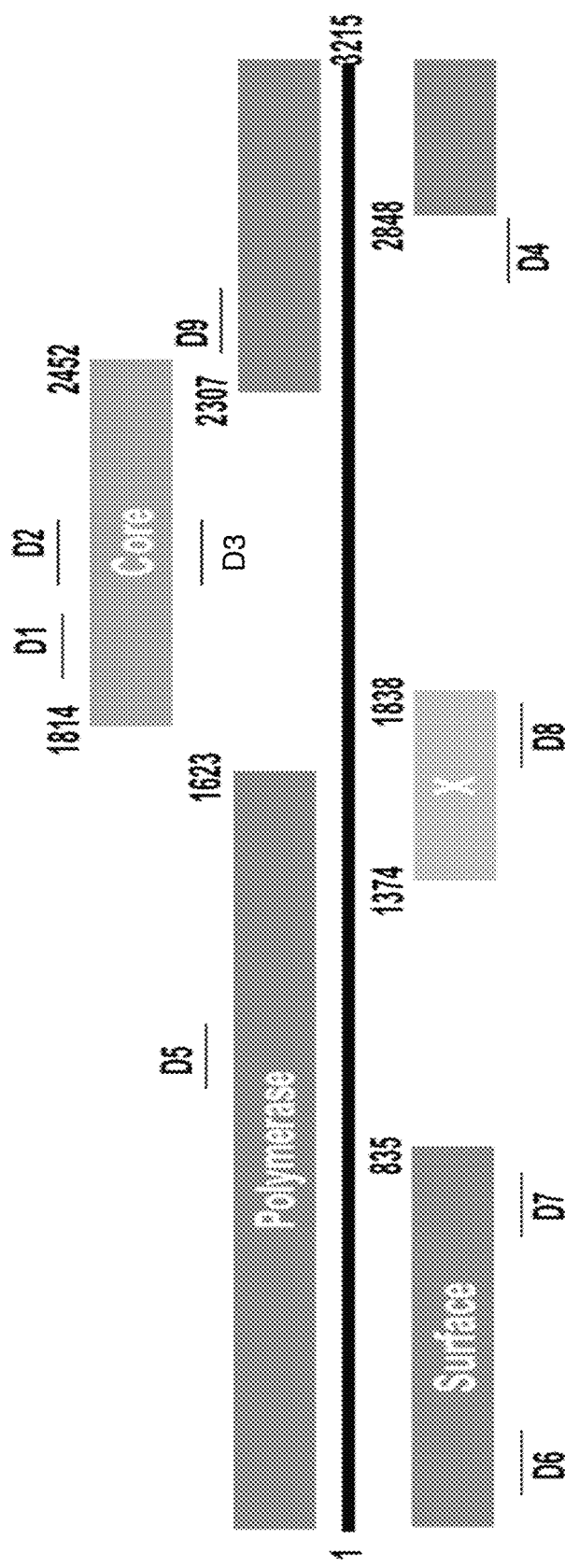
FIG. 1 schematically shows a sequence screening diagram and D1 to D9 of HBV DNA regions by genome analysis of HBV.

1-8: Construction of Oligonucleotides 1-8-1: Construction of Non-Modified Oligonucleotides FIG. 1 shows a sequence screening diagram capable of exhibiting an antiviral effect by forming a specific structure such as a G-quadruplex through genome analysis of HBV.

Oligo compounds D1 to D9 used in the present invention were synthesized by Cosmogenetech (Seoul, Korea) or Bio Basic (Canada). The detailed description of each compound is shown in Table 2 below.

stable against degradation. Partially modified D2 was partially modified at 5' and 3' end sequences. For example, PS-LNA (4,4) means an oligonucleotide whose entire backbone is PS and in which 4 nucleotides at each of the 5' and 3' ends are modified with LNA. Examples of D2 constructed by such partial modifications include PS-OMe (4,4), PS-OMe (5,5), PS-LNA (2,2) PS-LNA (3,3) (SEQ ID NO: 76), PS-LNA (4,4) (SEQ ID NO: 77), and PS-LNA (5,5).

TABLE 2

| Name | SEQ ID NO: | Sequence | Binding Regions |
|---|---|---|---|
| D1 | 1 | AAGCCTCCAAGCTGTGCCTTGGGTGGCT | ε structure (1866-1894); upper stream |
| D2 | 2 | TGCTGGGGGGAATTGA | core gene (2079-2094) |
| D3 | 3 | TGCTGGGTGGAATTGA | core gene (2079-2094), D2 mutant |
| D4 | 4 | ACTAGACACTATTTAA | SPI (2736-2751) |
| D5 | 5 | CGTTGATGCCTTTGTA | Pol. gene (1049-1064) |
| D6 | 6 | TTCTAGGGGGAACTAC | (276-291) |
| D7 | 7 | GATGTGGTATTGGGGG | (745-760) |
| D8 | 8 | AGGAGTTGGGGGAGGA | (1735-1750) |
| D9 | 9 | CATAAGGTGGGGAACT | (2466-2481) |

1-8-2: Construction of Modified Oligonucleotides

In order to optimize the antiviral effect, various types of oligonucleotides were prepared using D2 of 1-8-1 by the following nomenclature. DNA was named using A, G, C, and T in capital letters, and RNA was named using a, g, c, and t in lowercase letters. The lowercase letter m was added in front of the nucleic acid when the 2'-position of the pentose in the nucleotide was modified with O-methyl, a letter l was added in front of the nucleic acid when the oligonucleotides were modified with LNA. The DNA backbone was indicated by brackets ([ ]), when the backbone was phosphorothioate (PS). The normal DNA has no brackets. The above nomenclature is shown in Table 3.

A total of 58 oligonucleotides were synthesized according to the above nomenclature rules and are shown in Tables 4 and 5. In the present invention, the oligonucleotides shown in Tables 4 and 5 are represented by SEQ ID NO: 20 to SEQ ID NO: 77 sequentially, and the numbers assigned to the nucleic acid sequences in the Tables 4 and 5 are the oligo modification #.

TABLE 3

| | 2'-ribo | | 2'-deoxy | | 2'-O-Methyl | | LNA | |
|---|---|---|---|---|---|---|---|---|
| Adenosine | a | Adenosine | A | Adenosine | m(A or a) | Adenosine | l(A or a) |
| Guanosine | g | Guanosine | G | Guanosine | m(G or g) | Guanosine | l(G or g) |
| Cytidine | c | Cytidine | C | Cytidine | m(C or c) | Cytidine | l(C or c) |
| Uridine | u | Thymidine | T | Uridine | mu | Uridine | lu |
| Phosphorothioate | [ ] | | | Thymidine | mT | Thymidine | lT |

TABLE 4

| | | | | | | | | | | | | | | | | |
|---|---|---|---|---|---|---|---|---|---|---|---|---|---|---|---|---|
| 1 | [mT | mG | mC | mT | mG | lG | lG | mG | mG | mG | mA | mA | mT | mT | mG | mA] |
| 2 | [mT | mG | mC | mT | lG | lG | lG | lG | mG | mG | mA | mA | mT | mT | mG | mA] |
| 3 | [mT | mG | mC | mT | lG | lG | lG | lG | lG | mA | mA | mA | mT | mT | mG | mA] |
| 4 | [mT | mG | mC | lT | lG | lG | lG | lG | lG | lA | mA | mT | mT | mG | mA] |
| 5 | [mT | mG | mC | lT | lG | lG | lG | lG | lG | lA | lA | lT | mT | mG | mA] |
| 6 | [mT | mG | lC | lT | lG | lG | lG | lG | lG | lG | lA | lA | lT | lT | mG | mA] |
| 7 | [lT | lG | mC | mT | mG | mG | mG | mG | mG | mG | mA | mA | lT | lT | lG | lA] |
| 8 | [lT | lG | lC | mT | mG | mG | mG | mG | mG | mG | mA | lA | lT | lT | lG | lA] |
| 9 | [lT | lG | lC | lT | mG | mG | mG | mG | mG | lA | lA | lT | lT | lG | lA] |
| 10 | [lT | lG | lC | lT | lG | mG | mG | mG | mG | lG | lA | lT | lT | lG | lA] |
| 11 | [lT | lG | lC | lT | lG | mG | mG | lG | lG | lA | lA | lT | lT | lG | lA] |
| 12 | [T | G | C | T | G | G | lG | lG | G | G | A | A | T | T | G | A] |
| 13 | [T | G | C | T | G | lG | lG | lG | lG | G | A | A | T | T | G | A] |
| 14 | [T | G | C | T | lG | lG | lG | lG | lG | lG | A | A | T | T | G | A] |
| 15 | [T | G | C | lT | lG | lG | lG | lG | lG | lA | A | T | T | G | A] |
| 16 | [T | G | C | lT | lG | lG | lG | lG | lG | lA | lA | lT | lT | T | G | A] |
| 17 | [T | G | lC | lT | lG | lG | lG | lG | lG | lA | lA | lT | lT | G | A] |
| 18 | [lT | lG | C | T | G | G | G | G | G | G | A | A | lT | lT | lG | lA] |
| 19 | [lT | lG | lC | T | G | G | G | G | G | G | A | lA | lT | lT | lG | lA] |
| 20 | [lT | lG | lC | lT | G | G | G | G | G | lA | lA | lT | lT | lG | lA] |
| 21 | [lT | lG | lC | lT | lG | G | G | G | G | lG | lA | lA | lT | lT | lG | lA] |
| 22 | [lT | lG | lC | lT | lG | lG | G | G | lG | lG | lA | lA | lT | lT | lG | lA] |
| 23 | [lT | mG | lC | mT | lG | mG | lG | mG | lG | mG | lA | mA | lT | mT | lG | mA] |
| 24 | [mT | lG | mC | lT | mG | lG | mG | lG | mG | lG | mA | lA | mT | lT | mG | lA] |
| 25 | [lT | G | lC | T | lG | G | lG | G | lG | G | lA | A | lT | T | lG | A] |
| 26 | [T | lG | C | lT | G | lG | G | lG | G | lG | A | lA | T | lT | G | lA] |
| 27 | [mT | mG | mC | mT | mG | mG | mG | mG | mG | mG | lA | lA | lT | lT | lG | lA] |
| 28 | [lT | lG | lC | lT | lG | lG | lG | lG | lG | mA | mA | mT | mT | mG | mA] |
| 29 | [T | G | C | T | G | G | G | G | G | G | lA | lA | lT | lT | lG | lA] |
| 30 | [lT | lG | lC | lT | lG | lG | lG | lG | lG | lG | A | A | T | T | G | A] |

TABLE 5

| | | | | | | | | | | | | | | | | |
|---|---|---|---|---|---|---|---|---|---|---|---|---|---|---|---|---|
| 31 | [mT | mG | mC | mT | mG | mG | mG | mG | mG | mG | A | A | T | T | G | A] |
| 32 | [T | G | C | T | G | G | G | G | G | G | mA | mA | mT | mT | mG | mA] |
| 33 | [mT | mG | mC | mT | lG | lG | lG | lG | lG | lG | A | A | T | T | G | A] |
| 34 | [mT | mG | mC | mT | G | G | G | G | G | G | lA | lA | lT | lT | lG | lA] |
| 35 | [T | G | C | T | lG | lG | lG | lG | lG | lG | mA | mA | mT | mT | mG | mA] |
| 36 | [T | G | C | T | mG | mG | mG | mG | mG | mG | lA | lA | lT | lT | lG | lA] |
| 37 | [lT | lG | lC | lT | mG | mG | mG | mG | mG | mG | A | A | T | T | G | A] |
| 38 | [lT | lG | lC | lT | G | G | G | G | G | G | mA | mA | mT | mT | mG | mA] |
| 39 | [lT | lG | lC | lT | lG | lG | lG | lG | lG | lG | lA | lA | lT | lT | lG | lA] |
| 40 | lT | lG | lC | lT | lG | lG | lG | lG | lG | lG | lA | lA | lT | lT | lG | lA |
| 41 | [mT | mG | mC | mT] | lG | lG | lG | lG | lG | lG | [mA | mA | mT | mT | mG | mA] |
| 42 | [lT | lG | lC | lT] | mG | mG | mG | mG | mG | mG | [lA | lA | lT | lT | lG | lA] |
| 43 | [T | G | C | T] | lG | lG | lG | lG | lG | lG | [A | A | T | T | G | A] |
| 44 | [lT | lG | lC | lT] | G | G | G | G | G | G | [lA | lA | lT | lT | lG | lA] |
| 45 | [mT | mG | mC | mT] | lG | lG | lG | lG | lG | lG | [A | A | T | T | G | A] |

TABLE 5-continued

| | | | | | | | | | | | | | | | |
|---|---|---|---|---|---|---|---|---|---|---|---|---|---|---|---|
| 46 | [mT | mG | mC | mT] | G | G | G | G | G | G | [lA | lA | lT | lT | lG | lA] |
| 47 | [T | G | C | T] | lG | lG | lG | lG | lG | lG | [mA | mA | mT | mT | mG | mA] |
| 48 | [T | G | C | T] | mG | mG | mG | mG | mG | mG | [lA | lA | lT | lT | lG | lA] |
| 49 | [lT | lG | lC | lT] | mG | mG | mG | mG | mG | mG | [A | A | T | T | G | A] |
| 50 | [lT | lG | lC | lT] | G | G | G | G | G | G | [mA | mA | mT | mT | mG | mA] |
| 51 | T | G | C | T | [lG | lG | lG | lG | lG | lG] | A | A | T | T | G | A |
| 52 | [mu | mG | mC | mu | lG | lG | lG | lG | lG | lG | mA | mA | mu | mu | mG | mA] |
| 53 | [u | G | C | u | G | G | lG | lG | G | G | A | A | u | u | G | A] |
| 54 | [lu | mG | lC | mu | lG | mG | lG | mG | lG | mG | lA | mA | lu | mu | lG | lA] |
| 55 | [lu | lG | lC | lu | lG | lG | lG | lG | lG | lG | lA | lA | lu | lu | lG | lA] |
| 56 | [mu | mG | mC | mu] | lG | lG | lG | lG | lG | lG | [A | A | u | u | G | A] |
| (3, 3) | [lT | lG | lC] | T | G | G | G | G | G | G | A | A | T | [lT | lG | lA] |
| (4, 4) | [lT | lG | lC | lT] | G | G | G | G | G | G | A | A | [lT | lT | lG | lA] |

1-9: Electrophoretic Mobility Shift Assay (EMSA)

30 ng of HBV enhancer DNA was used and labeled with [32P]-gamma isotope. 500 ng of D2 was used to form a G-quadruplex. DNA (D2, pEnhIΔXp, pEnhIΔXp-D2, and enhancer I and II) was mixed with a buffer solution (10 mM Tris-HCl pH 7.5, 0.1 M KCl, 1 mM DTT, and 10 mM MgCl$_2$) and heated, and then cooled so that the DNA could be folded. After reaction with the DNA mixture, BG4 antibody (Absolute Antibody, United Kingdom) was added to identify specific G-quadruplex DNA through DNA-protein binding. After a binding reaction at room temperature, the DNA-DNA complex was subjected to electrophoresis at a cold temperature using 6% polyacrylamide gel. After electrophoresis, the gel was dried at 70° C. for 30 minutes. The results were analyzed using a phospho-imager.

1-10: Experiments Using Hydrodynamic Injection in Mice

Plasmid DNA (25 μg of HBV 1.2, 25 μg of D2, and 5 μg of b-gal) was delivered to 6-week-old mice (BALB/C) using the hydrodynamic injection method. PBS in a volume corresponding to 10% of the weight of the mice was prepared and intravenously injected into the tails of the mice. The modified D2 (50 μg) were also intravenously injected into the tails of the mice. PBS containing DNA was injected intravenously at a rapid rate using a syringe for 4 to 6 seconds. All animal experiments were approved by the Konkuk University Animal Care Committee.

1-11: Analysis Method of G-Quadraplex in Cells Using Microscope

A cover glass was laid on the bottom of a 6-well plate and the cells were cultured therein. The cells were transfected with HBV and treated with 500 nM of modified D2. The cells were fixed with acetone, washed three times with PBS, and blocked by PBS containing 3% BSA. After washing three times with PBS, BG4 (Absolute Antibody, Ab00174-1.1) antibody was mixed at a ratio of 1:300 and reacted overnight in a cold room. After washing 3 times with PBS, a cover glass was laid on the bottom of a 6-well plate and the cells were cultured therein using anti-mouse Alexa 568 for 1 hour. The cells were transfected with HBV and treated with 500 nM of modified D2. The cells were fixed with acetone, washed three times with PBS, and blocked by PBS containing 3% BSA. After washing three times with PBS, BG4 (Absolute Antibody, Ab00174-1.1) antibody was mixed at a ratio of 1:300 and reacted overnight in a cold room. After washing 3 times with PBS, the cells were reacted with anti-mouse Alexa 568 for 1 hour. After washing 3 times with PBS, the nuclei were stained with DAPI for 30 minutes. After washing three times with PBS, the cover glass was mounted on a glass slide and dried.

1-12: In Vivo Experiment Using Chitosan Nanoparticles

Plasmid DNA (25 μg of HBV 1.2 and 5 μg of b-gal) was delivered to 6-week-old mice (BALB/C) using a hydrodynamic injection method. PBS in a volume corresponding to 10% of the weight of the mice was prepared and intravenously injected into the tails thereof. PBS containing DNA was injected intravenously at a rapid rate using a syringe for 4 to 6 seconds. On the next day, 8 μg of chitosan nanoparticle D2 was also intravenously injected into the tails of the mice. Chitosan nanoparticles are molecules having low cytotoxicity and immunogenicity as well as efficient biocompatibility and have a feature of efficiently delivering oligonucleotides such as siRNA (Targeted Gene Silencing Using RGD-Labeled Chitosan Nanoparticles, Hee Dong Han, Clin Cancer Res. 2010).

The chitosan nanoparticles used in the above experiment were prepared based on the ionic gelation between chitosan (MW 50 kDa to 190 kDa) and D2. TPP (0.25% w/v) and D2 (1 μg/μl) were added to a 1% (w/v) chitosan solution. A continuous reaction took place at room temperature, and after the incubation reaction, pellets were obtained by centrifugation at 13,000 RPM for 40 minutes at 4° C. The thus-obtained pellets were washed 3 times with DW and stored at 4° C. until use. All animal experiments were approved by the Konkuk University Animal Care Committee.

Example 2: Confirmation of Antiviral Effect 2-1: Confirmation of Oligonucleotides Showing Antiviral Effect The D1 to D9 oligonucleotides were transfected with liver cancer cell lines as HBV, and the antiviral effect was judged by the inhibition of formation of viral proteins (HBsAg and HBeAg) and the inhibition of replication.

Specifically, HBV 1.2 plasmid and oligonucleotides (D1 to D9, SEQ ID NOS: 1 to 9, respectively) were transfected to HepG2. The cells and supernatants were cultured for 3 days after the transfection. Secreted HBeAg and HBsAg were measured in order to determine HBV protein expression. HBeAg and HBsAg in the culture media were analyzed using HBeAg and HBsAg ELSIA kits (Wantai Pharm Inc., Beijing, China). HBV DNA was measured by Southern blot.

Figure 2A:
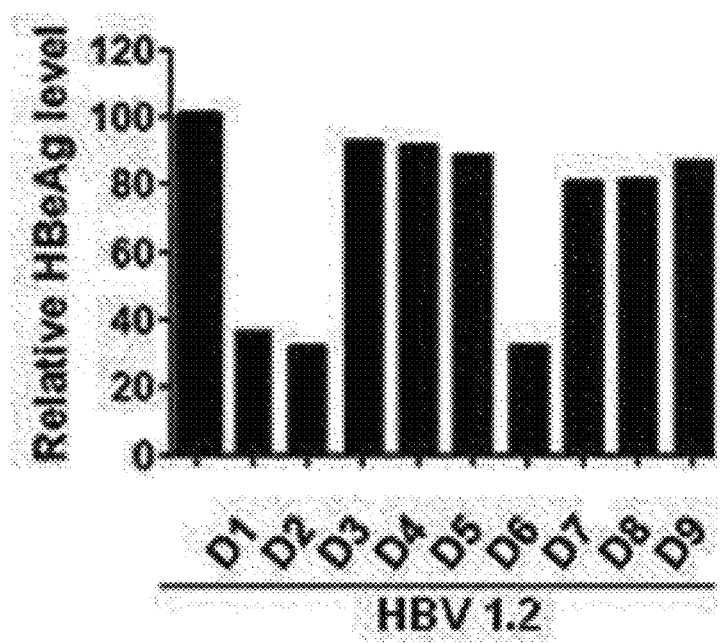
FIGS. 2A-C show that oligonucleotides (D1, D2, and D6) have an inhibitory effect against protein expression (FIGS. 2A and 2B) and HBV replication (FIG. 2C).
Figure 2B:
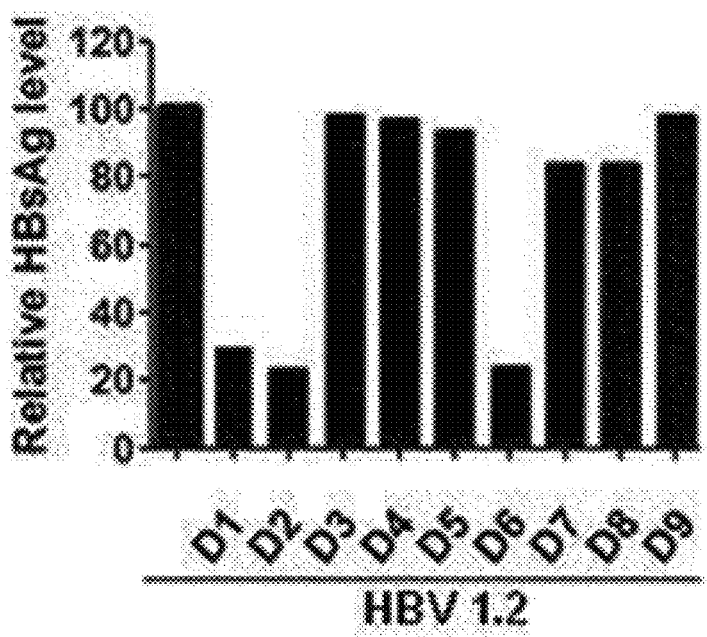
Figure 2C:
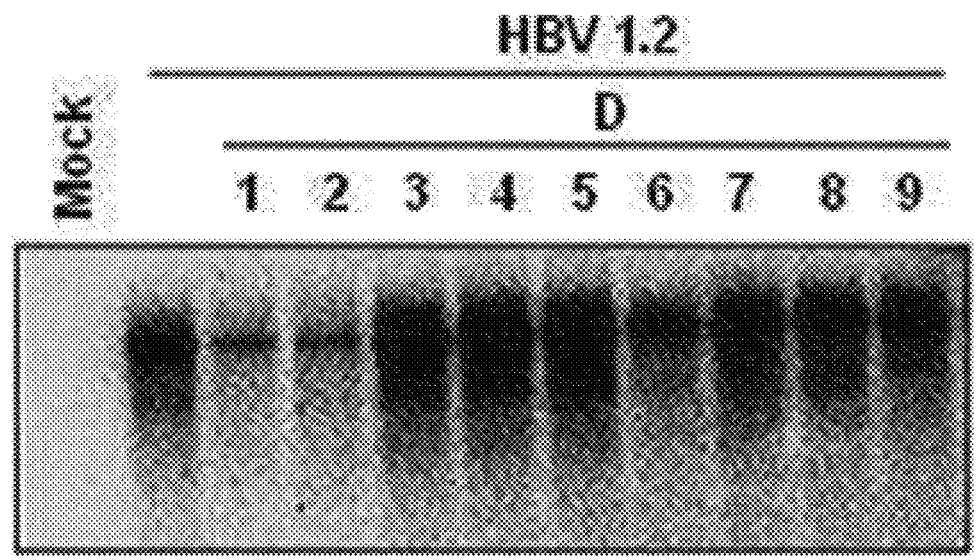

As a result, D1, D2, and D6 exhibited an antiviral effect, as shown in FIG. 2.

2-2: Inhibition of HBV RNA Expression

An experiment was conducted to confirm the inhibition of HBV RNA expression using D2 oligonucleotide, which showed the most superior antiviral efficacy among D1, D2, and D6 oligonucleotides, as confirmed in Example 2-1. Specifically, in order to determine what stage of HBV life cycle was inhibited by the D2 oligonucleotide, Huh7 cells were transfected with HBV 1.2-mer, and the HBV mRNA level was analyzed by Northern blot.

Figure 3:
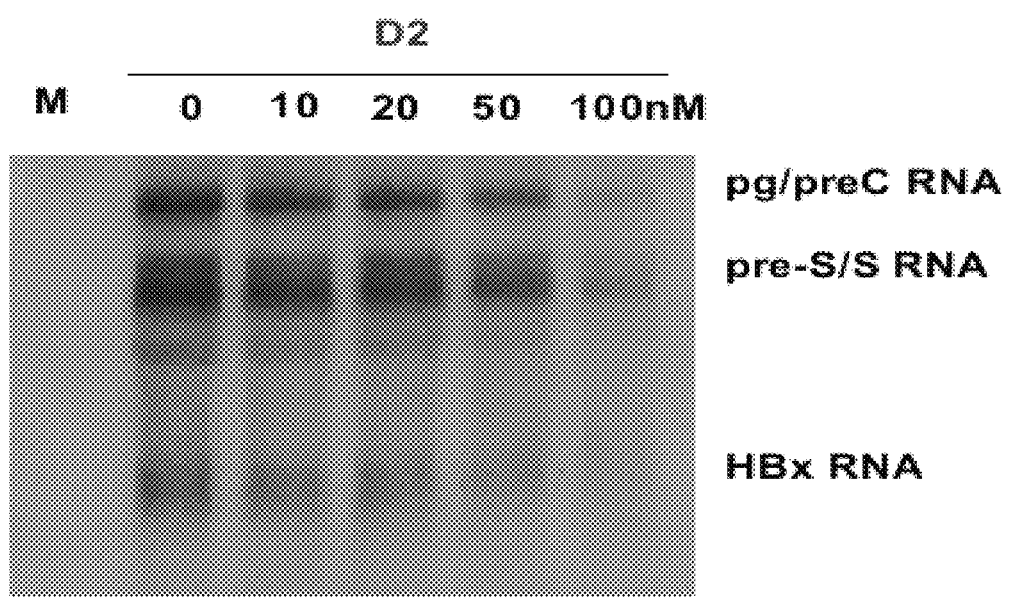
FIG. 3 shows that the oligonucleotides inhibit the transcription of viral mRNAs. pg/preC RNA represents pregenomic and precore RNA; pre-S/S RNA represents surface RNA; and HBx RNA represents RNA that produces HBx protein.

As a result, it was confirmed that the D2 oligonucleotide inhibited HBV RNA in a dose-dependent manner, as shown in FIG. 3. Therefore, it was confirmed that the D2 oligonucleotide also inhibited the HBV RNA expression, thereby confirming that the D2 oligonucleotide inhibited the expression by acting at the RNA transcription stage of the virus.

2-3: Confirmation of Inhibition of HBV Protein Expression

In order to confirm whether D2 oligonucleotide inhibits HBV protein expression, Huh7 cells were transfected with HBV 1.2-mer and D2 oligonucleotide, and then the surface protein expression level was measured by Western blot analysis.

Figure 4:
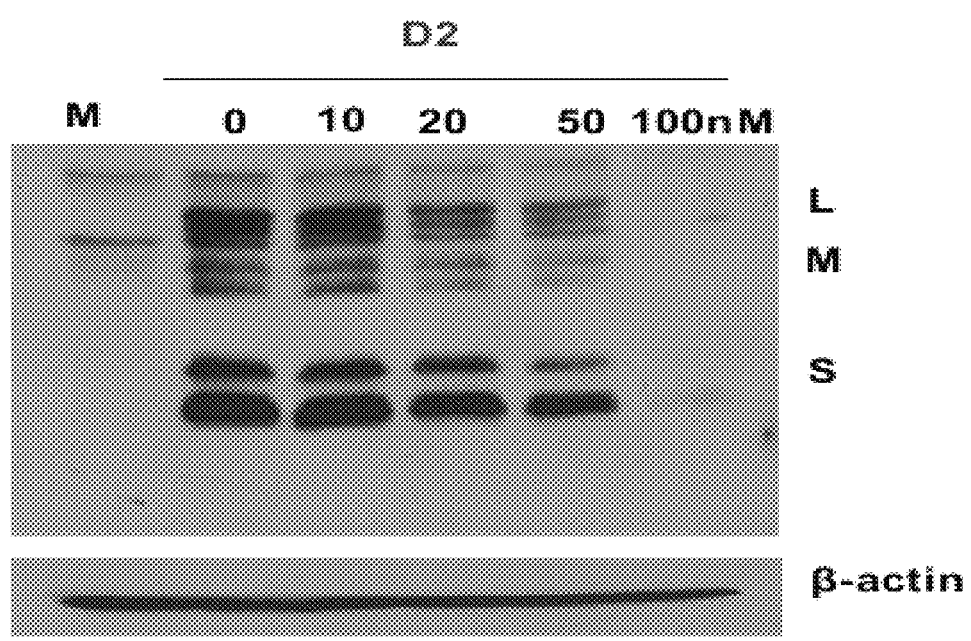
FIG. 4 shows that the oligonucleotides inhibit viral surface proteins. Beta-actin is a loading control, and L, M, and S represent three kinds of surface proteins, wherein L represents large, M represents medium, and S represents small.

As a result, it was confirmed that the D2 oligonucleotide inhibited the expression of surface protein, one of the HBV proteins, in a concentration-dependent manner, as shown in FIG. 4.

2-4: Inhibition of HBV Enhancer/Promoter Activity

In order to investigate how D2 oligonucleotide reduces HBV mRNA level, a luciferase reporter assay was performed using HBV enhancers.

As a result, it was confirmed that about 80% of the activity of HBV enhancers I and II was inhibited by the D2 oligonucleotide transfection, as shown in FIGS. 5 (*a*) and (*b*). These results confirmed that the D2 oligonucleotide inhibited the activity of both enhancers I and II. However, no effect was observed upstream of enhancer I (EnhI) and pEnhIΔXp. HBV enhancer II (EnhII) was inhibited by about 48% by the D2 oligonucleotide transfection. Based on these results, it was confirmed that 1742 G-rich regions (regions from 1742 to 1747) of HBV enhancer II are important for inhibiting enhancer activity by D2 oligonucleotide.

Consequently, the results of FIG. 5 confirmed that the D2 oligonucleotide reduced the activity of the enhancer I and II, thereby exhibiting an antiviral effect at the transcription stage.

In order to investigate how D2 oligonucleotide reduces the activity of HBV enhancers, the aforementioned reporter plasmids were constructed, and the reporter activity was measured. As shown in FIG. 6 (*a*), the base G-rich HBV motifs of D2, D6, D7, and D8 shown in Table 2 were introduced into the reporter plasmid promoter regions.

As a result, it was confirmed that the pEnhIΔXp luciferase clone had no effect, but the pEnhIΔXp luciferase clone containing a D2 or D6 motif strongly inhibited luciferase activity, as shown in FIG. 6 (*b*).

Therefore, it was confirmed that although the D2 oligonucleotide did not function at all in the pEnhIΔXp reporter, which was upstream of enhancer I (EnhI), it exhibited a strong inhibitory effect when the reporter plasmids were constructed by adding the same nucleotide sequence to D2, and it was further confirmed that the reporter containing D6 oligonucleotide having the nucleotide sequence similar to D2 oligonucleotide was also inhibited. These results imply that the D2 oligonucleotide recognizes and inhibits its nucleotide sequence.

Example 3: Formation of G-Quadruplex Structure 3-1: Confirming that D2 Oligonucleotide Forms G-Quadruplex by Recognizing HBV Enhancer I and II Regions An in vitro electrophoretic mobility shift assay (EMSA) was performed using the D2 oligonucleotide and the P32-labeled HBV enhancer sequence, in order to confirm whether the D2 oligonucleotide forms a G-quadruplex with the sequences of enhancers I and II (FIG. 7 (*a*)).

Figure 7A:
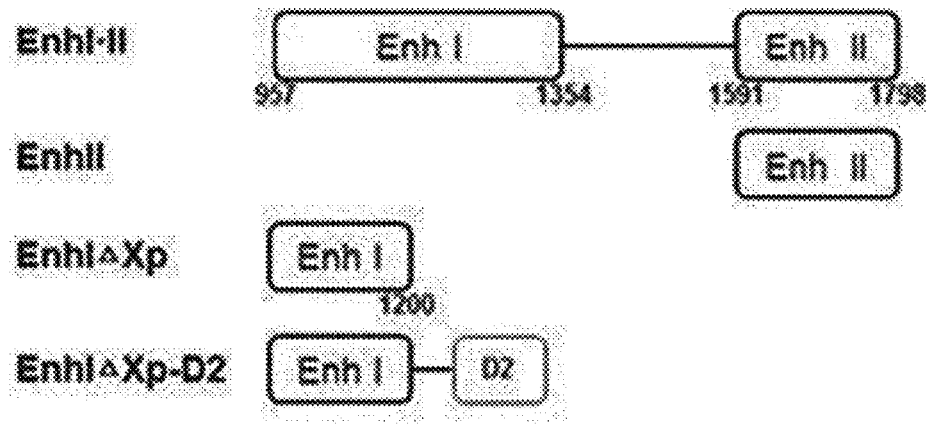
FIG. 7 shows the results of electrophoretic mobility shift assay (EMSA) of oligonucleotides, illustrating that the oligonucleotides bind to the HBV enhancer I and II sequences to form a G-quadruplex.
Figure 7B:
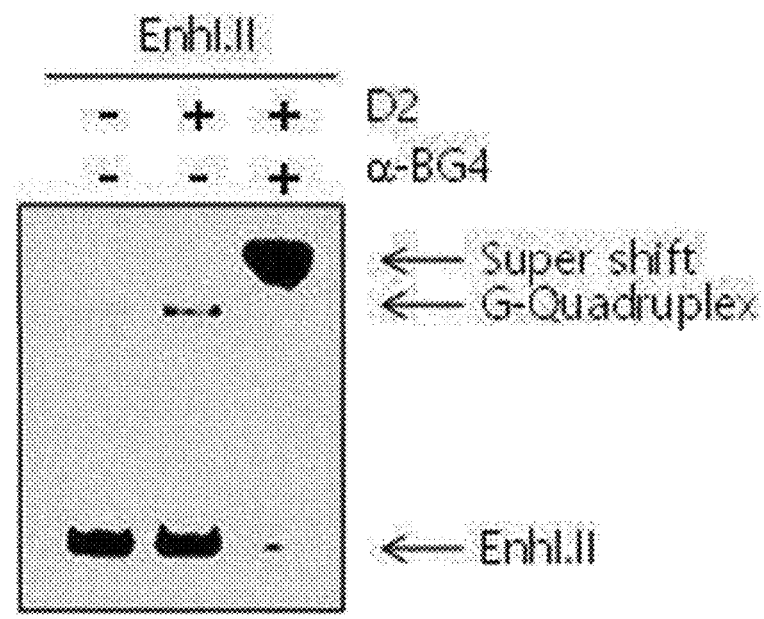

As a result, it was confirmed that the D2 oligonucleotide partially formed a G-quadruplex with the sequences of enhancers I and II through EMSA. As shown in FIG. 7 (*b*), the formation of the G-quadruplex was confirmed by band super shifts using G-quadruplex-specific BG4 antibodies. This is the result obtained by visualizing the gel with phosphor-imaging. That is, it was confirmed through FIG. 7 that the D2 oligonucleotide physically binds to the HBV enhancer regions to form a G-quadruplex, thereby inhibiting the HBV enhancer activity.

3-2: Confirming that D2 Oligonucleotides Forms G-Quadruplex with HBV Enhancer II Region An in vitro EMSA was performed using D2 and HBV in order to confirm whether the D2 oligonucleotide forms a G-quadruplex with the enhancer II region.

Figure 8:
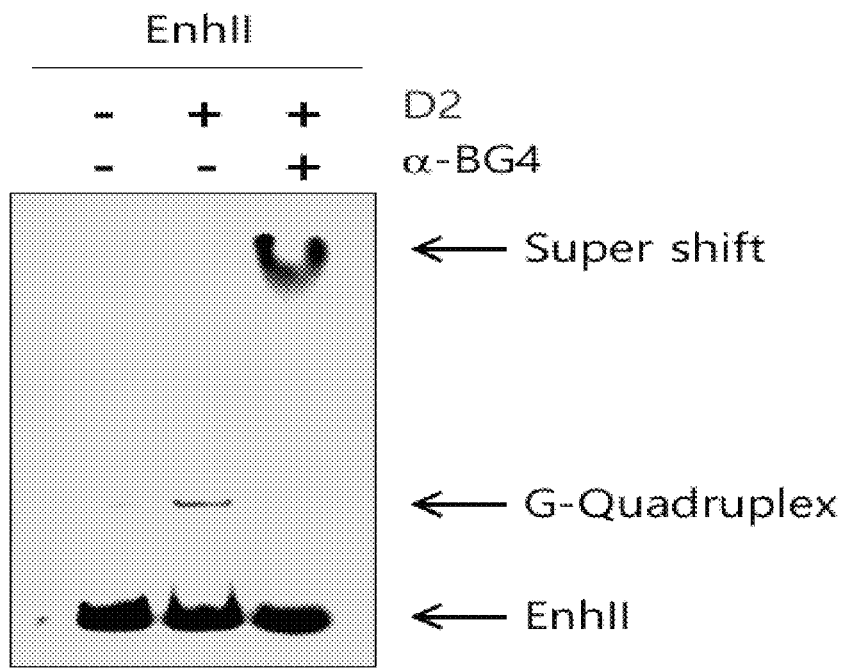
FIG. 8 shows the results of electrophoretic mobility shift assay (EMSA) of oligonucleotides, illustrating that the oligonucleotides partially form a G-quadruplex with the HBV enhancer II region.

As a result, it was confirmed that the D2 oligonucleotide partially formed a G-quadruplex with the enhancer II sequence through EMSA. The formation of the G-quadruplex was confirmed by band super shifts using G-quadruplex-specific BG4 antibodies. In addition, it was confirmed through FIG. 8 that the D2 oligonucleotide formed a G-quadruplex through the HBV enhancer II region.

3-3: Confirming that D2 Oligonucleotide Forms Complete G-Quadruplex Structure with Region Having Nucleotide Sequence of its Own An in vitro EMSA was performed in order to confirm whether the D2 oligonucleotide forms a complete G-quadruplex with the HBV genome through the sequence of its own.

Figure 9:
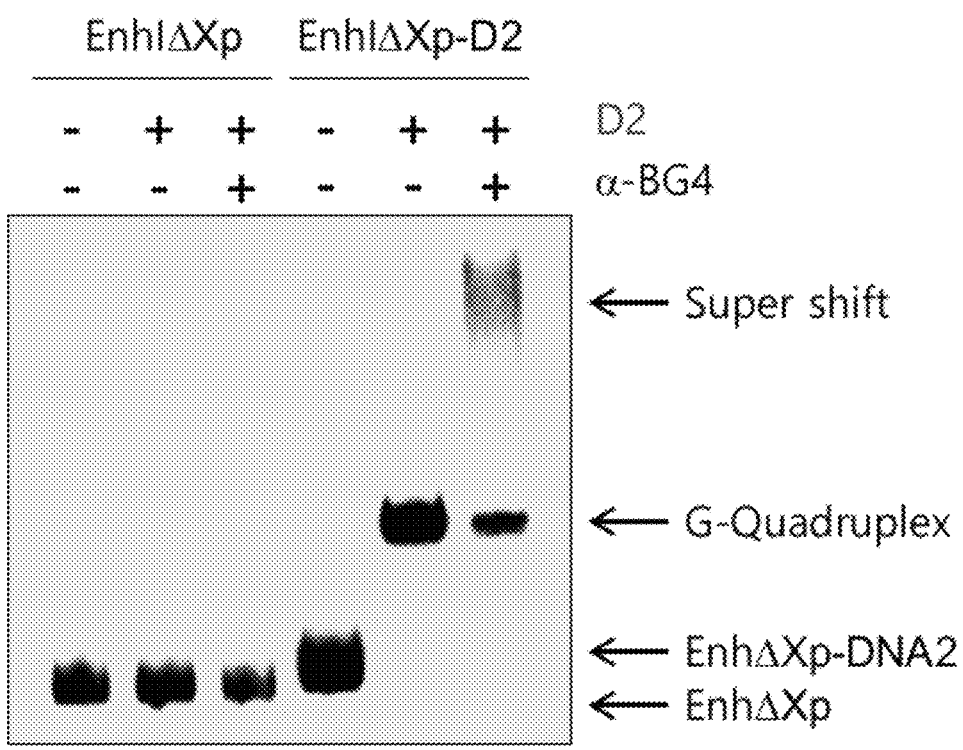
FIG. 9 shows the results of electrophoretic mobility shift assay (EMSA) of oligonucleotides, illustrating that the oligonucleotides recognize nucleotide sequences of their own and form a G-quadruplex structure.

As a result, it was confirmed that the D2 oligonucleotide formed a complete G-quadruplex with the HBV genome through the sequence of its own, as shown in FIG. 9. The formation of the G-quadruplex was confirmed by band super shifts using G-quadruplex-specific BG4 antibodies, and the gel was visualized with phosphor-imaging.

According to FIG. 9, the D2 oligonucleotide did not bind to the enhancer I region (EnhIΔXp), but formed a complete G-quadruplex structure with the region to which the sequence of its own was introduced (EnhIΔXp-D2). These results imply that the D2 oligonucleotide recognizes the nucleotide sequence of its own and forms a G-quadruplex structure, and thus are associated with the inhibition of the virus.

Figure 10:
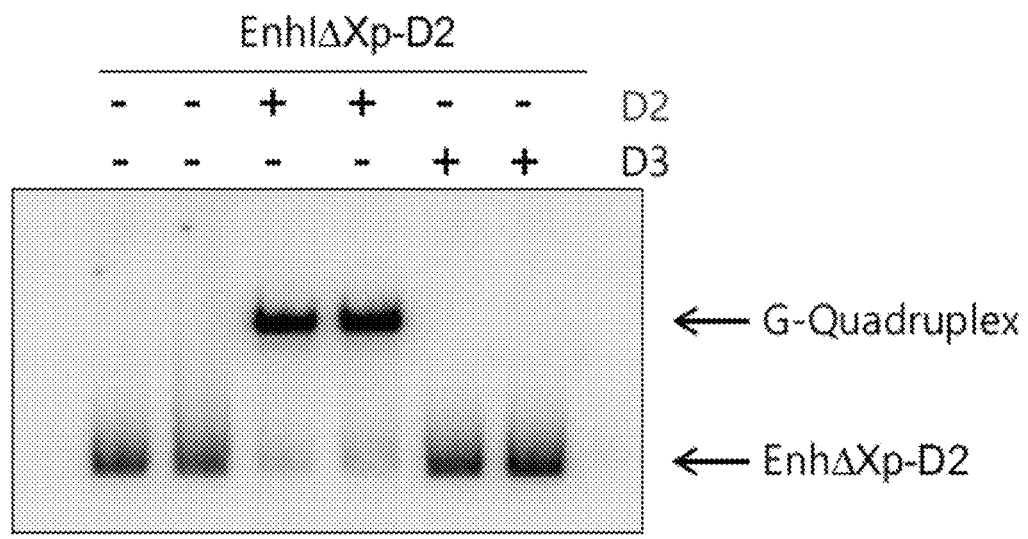
FIG. 10 shows the EMSA results for investigating whether a mutant nucleotide that caused a point mutation in the oligonucleotides forms a G-quadruplex. The oligonucleotides with the point mutation do not form a G-quadruplex.

3-4: Confirming that D3 Oligonucleotide Introduced with a Point Mutation in the Nucleotide Sequence of D2 Oligonucleotide does not Form G-Quadruplex Structure As shown in FIG. 10, it was confirmed that D3 oligonucleotide in which a point mutation was introduced in the nucleotide sequence of the D2 oligonucleotide through in vitro EMSA did not form a G-quadruplex structure. Specifically, the D3 oligonucleotide in which the conservative GGGGGG was point-mutated to GGGTGG in the middle region of the D2 oligonucleotide sequence did not form a G-quadruplex with the HBV genome. From these results, it can be seen that the G-rich region of the D2 oligonucleotide is very important for the formation of the G-quadruplex.

In addition, as can be seen in FIG. 2, the D3 oligonucleotide did not exhibit a virus inhibitory activity at all. With reference to the results showing that the D3 oligonucleotide did not form a G-quadruplex, which was confirmed by EMSA shown in FIG. 10, the formation of the G-quadruplex structure is essential for the antiviral action.

Example 4: Inhibition of HBV Activity 4-1: Confirming that Modified D2 Oligonucleotides Inhibit HBV Enhancer Activity by Penetrating into Cells Plasmids of HBV enhancers I and II were transfected with HepG2 cells. Prior to transfection, a plurality of modified D2 oligonucleotides (PS, OMe, PNA, LNA, PS-OMe, PS-LNA) were pre-treated with HepG2 cells (at a final concentration of 500 nM). On the next day, the cells were replaced with fresh media (DMEM) containing 500 nM of the modified D2 oligonucleotides. Then, the cells were cultured for 24 hours after the transfection, and the luciferase activity was analyzed using the Steady Glo-Luciferase system.

Figure 11:
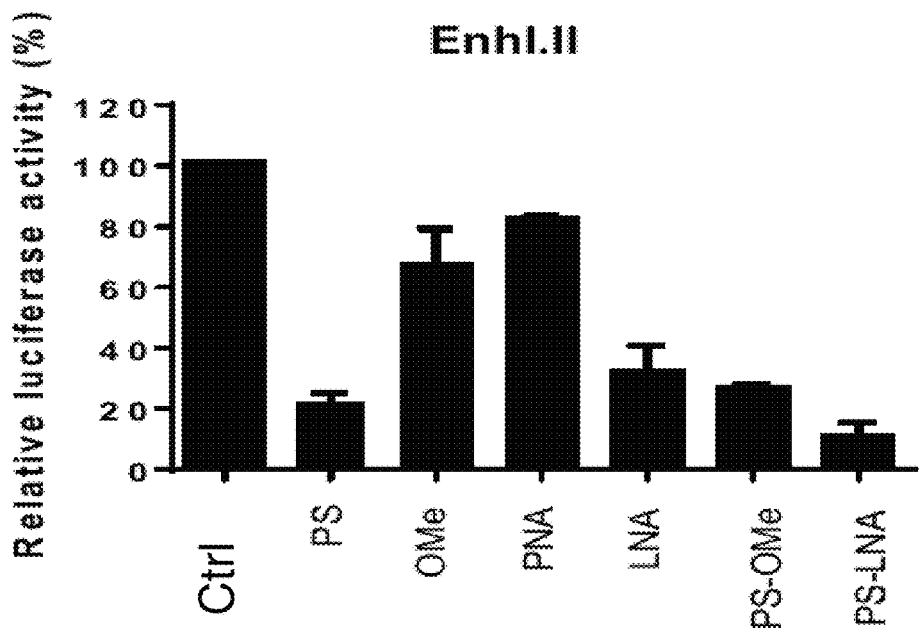
FIG. 11 shows the results of measuring HBV inhibitory activity of oligonucleotides through a luciferase activity assay. PS represents a D2 modified with phosphorothioate, OMe represents a D2 modified with O-methyl, PNA represents a D2 modified with PNA, PS-OMe represents a D2 modified with phosphorothioate and O-methyl, and PS-LNA represents a D2 modified with phosphorothioate and LNA.

As a result, it was confirmed that the modified oligonucleotides showed superior cell penetration and HBV inhibitory activity with the PS modification, as shown in FIG. 11. According to the above results, the modification in the backbone of the oligonucleotides with phosphorothioate (PS) or locked nucleic acids (LNA) improves the permeability of the oligonucleotides and consequently increases the antiviral effect of the oligonucleotides.

4-2: Confirming that Modified D2 Oligonucleotides Inhibit HBV in HBV-Transfected Model In order to investigate whether the modified D2 oligonucleotides also show an inhibitory effect in an HBV-transfected model, HepG2-NTCP cell line, which is an HBV-infectious cell line, was transfected with HBV and then treated with D2 oligonucleotides modified with PS (PS, PS-OMe, PS-LNA). Specifically, as HBV transfection and viral protein analysis of HepG2-NTCP cells of FIG. 12 (a) are shown in the schematic diagram, the experimental procedure is as follows: HepG2-NTCP cells were transfected with 2000 HBV genome equivalent per cells (Geq/cell) cultured in PMM (PHH maintain media, Gibco) containing 2% DMSO and 4% PEG8000 for 16 to 20 hours. Then, the cells were washed three times with 500 µl of PBS, maintained in PMM (2% DMSO), and cultured for 7 days after the transfection. In order to analyze HBV protein expression, secreted HBeAg and HBsAg were measured. HBeAg and HBsAg in the culture media were analyzed using HBeAg and HBsAg ELISA kits (Wantai Pharm Inc, Beijing, China). The transfection of D2 oligonucleotide (D1, T.F) was used as a positive control for the anti-HBV effect. Unmodified D2 oligonucleotide treatment (D2 Tr) was used as a negative control. LMV is lamivudine.

Figure 12A:
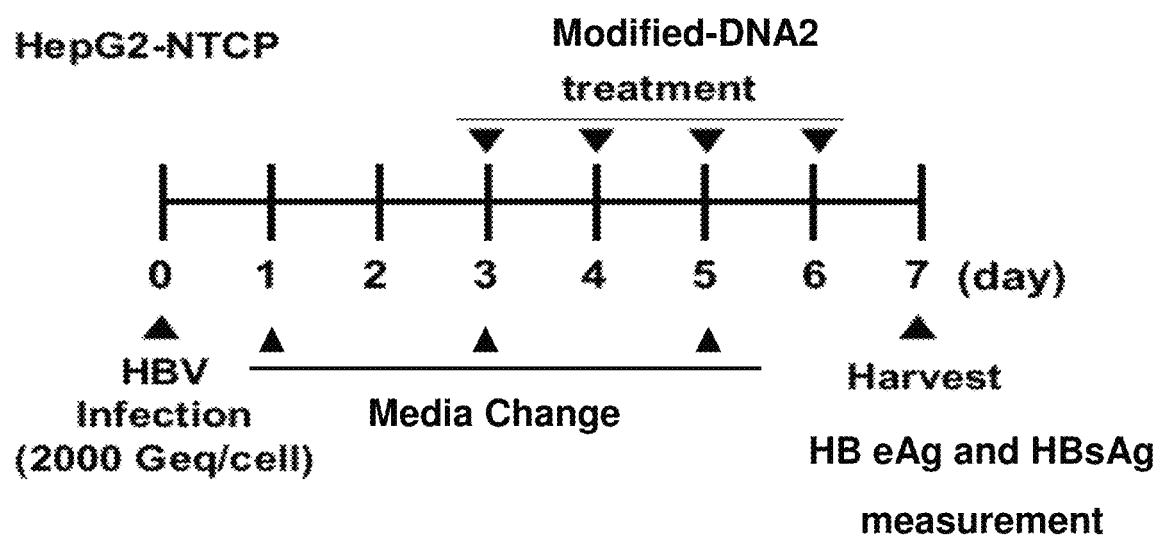
FIG. 12A schematically shows HBV transfection and viral protein analysis of HepG2-NTCP cells.
Figure 12B:
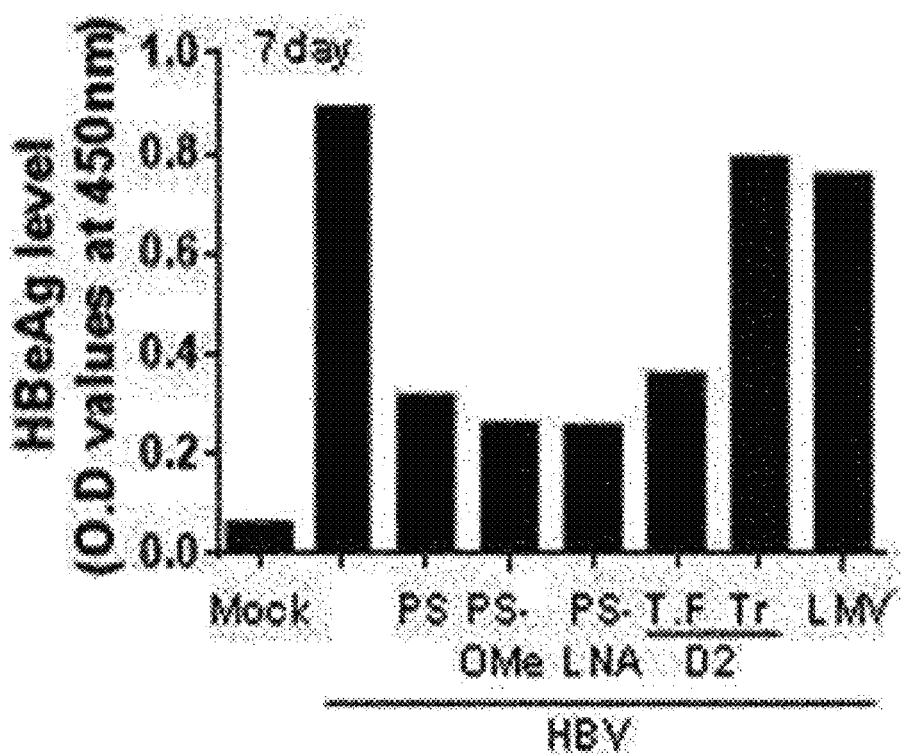

As a result of the HBV protein expression, it was confirmed that the D2 oligonucleotides modified with PS (PS, PS-OMe, PS-LNA) also inhibited HBV in HepG2-NTCP, which is an HBV-infectious cell line, thereby confirming that an antiviral effect was exhibited upon treatment with the modified D2 oligonucleotides, as shown in FIGS. 12 (b) and (c).

4-3: Confirming that Modified D2 Oligonucleotides Inhibit HBV in Primary Human Hepatocytes (PHH)

In order to confirm whether the D2 oligonucleotides modified with PS inhibit HBV in primary human hepatocyte (PHH), PHHs were isolated from the liver tissue of a patient after liver operation, and then the cells were transfected with HBV to investigate the antiviral effect of the modified D2 oligonucleotides. Specifically, as HBV transfection and viral protein analysis of PHH of FIG. 13 (a) are shown in the schematic diagram, the experimental procedure is as follows: PHHs were transfected with 5000 HBV genome equivalent per cells (Geq/cell) cultured in PMM (PHH maintain media, Gibco) containing 2% DMSO and 4% PEG8000 for 16 to 20 hours. Then, the cells were washed three times with 500 µl of PBS, maintained in PMM (2% DMSO), and cultured for 7 days after the transfection. In order to analyze HBV protein expression, secreted HBeAg and HBsAg were measured. HBeAg and HBsAg in the culture media were analyzed using HBeAg and HBsAg ELISA kits (Wantai Pharm Inc, Beijing, China). Unmodified D2 oligonucleotides were used as a negative control. LMV is lamivudine.

As a result of the HBV protein expression analysis, it was confirmed that the modified D2 oligonucleotides had an excellent antiviral effect, and in particular, the D2 oligonucleotides modified with PS-LNA inhibited the virus by more than 90%, showing the strongest inhibitory effect, as shown in FIG. 13. These results confirmed that an antiviral effect was exhibited when the modified D2 oligonucleotides were treated to human cells.

4-4: Analysis of D2 Oligonucleotides

In order to find the modified forms that exhibit the most optimal effect, three (3,3), four (4,4), or five (5,5) nucleotides at the end of D2 oligonucleotide were modified. For analysis, the structures of the HBV enhancers I and II were transfected with HepG2 cells. Prior to transfection, a plurality of modified D2 (PS, PS-OMe (4,4), PS-OMe (5,5), PS-OMe (all), PS-LNA (2,2), PS-LNA (3,3), PS-LNA (4,4), PS-LNA (5,5), PS-LNA (all)) were pre-treated with HepG2 cells (at a final concentration of 500 nM). On the next day, the cells were replaced with fresh media (DMEM) containing 500 nM of the modified D2 oligonucleotide. After two days of the transfection, the luciferase activity of the HBV enhancers was assayed according to the protocol using the luciferase assay system (Promega; Madison, Wis.).

As a result, it was confirmed that the modified D2 oligonucleotides showed superior antiviral effects, as shown in FIG. 14. Among them, PS-LNA (4,4), in which 4 nucleotides at both the 5' and 3' ends were modified with LNA, showed the strongest antiviral effect.

4-5: Confirmation of Antiviral Effect of Modified Oligonucleotides in HepG2 Cells The oligonucleotides prepared in 1-8-2 were inserted into HepG2 cells together with HBV. 58 oligonucleotides were used at a concentration of 50 nM, and were added to 2 ml of media together with 1 µg of HBV to transfect the cells. On the next day, the media was replaced with fresh media (DMEM) and the cells were cultured for 72 hours. Subsequently, HBeAg and HBsAg in the culture media were analyzed using HBeAg and HBsAg ELISA kits (Wantai Pharm Inc., Beijing, China). The results for HBeAg and HBsAg are shown in FIG. 15 and FIG. 16, respectively.

As a result, it was confirmed that a plurality of oligonucleotides inhibited HBeAg, as shown in FIG. 15. In particular, the substances that effectively reduced HBeAg in HepG2 cells were 9, 17, 18, 20, 21, 34, 37, 40, 41, 42, 43, 44, 46, 47, 50, 51, 54, 55, (3,3), and (4,4).

In addition, as shown in FIG. 16, it was confirmed that a plurality of oligonucleotides inhibited HBsAg. In particular, the substances that effectively reduced HBsAg in HepG2 cells were 9, 10, 18, 20, 21, 24, 28, 34, 37, 40, 41, 44, 48, and (3,3).

4-6: Confirmation of Effect of Modified Oligonucleotides in HepG2-NTCP Cells

In order to confirm the effect of the oligonucleotides prepared in 1-8-2 in an HBV-transfected model, HepG2-NTCP cells, which are HBV infectious cells, were used. Specifically, HBV was transfected with 2000 HBV genome equivalent per cells (Geq/cell) cultured in PMM (PHH maintain media, Gibco) containing 2% DMSO and 4% PEG8000 for 16 to 20 hours. Then, the cells were washed three times with 500 µl of PBS, maintained in PMM (2% DMSO), and then cultured for 7 days. From 3 days after the transfection, the cells were treated with 58 modified oligonucleotides daily. The treatment concentration was 500 nM. On day 7 after the transfection, HBV protein expression was analyzed by measuring secreted HBeAg and HBsAg. HBeAg and HBsAg in the culture media were analyzed using HBeAg and HBsAg ELISA kits. The results for HBeAg and HBsAg are shown in FIG. 17 and FIG. 18, respectively.

As a result, it was confirmed that a plurality of oligonucleotides inhibited HBeAg, as shown in FIG. 17. In particular, the substances that effectively reduced HBeAg in HepG2-NTCP cells were 8, 17, 18, 19, 20, 21, 27, 40, 44, 47, 55, (3,3), and (4,4). In addition, as shown in FIG. 18, it was confirmed that a plurality of oligonucleotides also inhibited HBsAg. In particular, the substances that effectively reduced HBsAg in HepG2-NTCP cells were 7, 8, 9, 18, 19, 20, 40, 42, 44, 45, (3,3), and (4,4).

4-7: Confirmation of Effects of Modified Oligonucleotide in PHH (Primary Human Hepatocyte) Cells In order to confirm whether the oligonucleotides prepared in 1-8-2 inhibit HBV in primary human hepatocyte (PHH), PHHs were isolated from the liver tissue of a patient after liver operation and transfected with HBV to confirm the antiviral effects of 58 modified oligonucleotides. Specifically, HBV transfection and viral protein analysis of PHHs are as follows: HBV was transfected with 2000 HBV genome equivalent per cells (Geq/cell) cultured in PMM (PHH maintain media, Gibco) containing 2% DMSO and 4% PEG8000 for 16 to 20 hours. Then, as HepG2-NTCP cells, the PHH cells were washed three times with 500 µl of PBS, maintained in PMM (2% DMSO), and then cultured for 11 days. From 5 days after the transfection, the cells were treated with 58 modified oligonucleotides daily. The treatment concentration was 500 nM. On day 11 after the transfection, HBV protein expression was analyzed by measuring secreted HBeAg and HBsAg. The results for HBeAg and HBsAg are shown in FIG. 19 and FIG. 20, respectively.

As a result, it was confirmed that a plurality of oligonucleotides inhibited HBeAg. In particular, the substances that effectively reduced HBeAg in PHH cells were 7, 8, 18, 19, 20, 52, (3,3), and (4,4), as shown in FIG. 19. In addition, as shown in FIG. 20, it was confirmed that a plurality of oligonucleotides also inhibited HBsAg. In particular, the substances that effectively reduced HBsAg in PHH cells were 6, 7, 8, 15, 16, 18, 19, 42, (3,3), and (4,4).

As a result of the HBV protein expression analysis, it was confirmed that the modified D2 oligonucleotides had an excellent antiviral effect as shown in the gapmers in the respective results, and in particular, among the gapmers of various types, D2 partially modified with PS-LNA showed the strongest inhibitory effect. HBeAg and HBsAg inhibitory effects were excellent especially in the region where G was repeatedly present when the region is not modified as (3, 3) or (4, 4). This implies that the cost required for the synthesis of oligonucleotides can be reduced, and further, it was confirmed that antiviral effects were exhibited when partially or fully modified D2 oligonucleotides were treated to human cells.

Example 5: In Vivo Model 5-1: Confirming that D2 Oligonucleotides Inhibit HBV in In Vivo Mouse Model In order to investigate whether the D2 oligonucleotides also function in vivo, an experiment was carried out using an HBV mouse model. The experiment was carried out according to FIG. 21 (*a*). Male 6-week-old mice were used for each group. PBS was injected as a control (Mock). DNAs injected (HI) by the hydrodynamic injection method are as follows: 25 µg of HBV-1.2mer, 25 µg of empty vector or D2 oligonucleotide, and 5 µg of b-gal. The b-gal was used as an injection control. Mice were sacrificed to obtain a blood sample. The mouse serum was diluted with PBS (at 1:50 for HBeAg and at 1:2000 for HBsAg). Viral proteins (HBeAg and HBsAg) were measured with an ELISA kit.

As a result, it was confirmed that a strong antiviral effect was exhibited in the mice injected with D2 oligonucleotides as shown in FIGS. 21 (*b*) and (*c*). In addition, as shown in FIG. 21 (*d*), it was confirmed that HBV DNA was greatly reduced in the mice injected with D2 oligonucleotides using Southern blot.

5-2: Confirming that Modified D2 Oligonucleotides Inhibit HBV when Injected Intravenously into In Vivo Mouse Model In order to investigate whether the modified D2 oligonucleotides function in vivo when injected, an experiment was carried out using an HBV mouse model. The in vivo experiment was carried out according to FIG. 22 (*a*). Male 6-week-old mice were used for each group. Mice only injected with HBV were used as a control. Plasmids containing 25 µg of HBV-1.2mer and 5 µg of b-gal were injected by the hydrodynamic injection method. Then, 50 µg of modified DNAs (PS, PS-OMe, and PS-LNA) were intravenously injected for 3 days. After 4 days of the injection, the mice were sacrificed to obtain a blood sample. The b-gal was used as an injection control. The mouse serum was diluted with PBS (at 1:50 for HBeAg and at 1:2000 for HBsAg). Viral proteins (HBeAg and HBsAg) were measured with an ELISA kit.

As a result, a strong antiviral effect was exhibited in the mice injected with the modified D2 oligonucleotides, as shown in FIGS. 22 (*b*) and (*c*). In addition, as shown in FIG. 22 (*d*), it was confirmed that the antiviral effect was also exhibited at the HBV DNA level. These results confirmed that when the modified D2 oligonucleotides were injected, they were delivered to the liver of the mice and exhibited a virus inhibitory action.

5-3: Confirming that D2 Oligonucleotides Inhibit HBV when Encapsidated with Nanoparticles (Chitosan) and Intravenously Injected into In Vivo Mouse Model In order to investigate whether the D2 oligonucleotides function in vivo when encapsidated with nanoparticles (chitosan) and injected, an experiment was carried out using an HBV mouse model. When the D2 oligonucleotides are encapsidated by nanoparticles, they are efficiently delivered to the liver. An in vivo experiment was carried out according to FIG. 23 (*a*). Male 6-week-old mice were used for each group. Plasmids containing 25 µg of HBV-1.2mer and 5 µg of b-gal were injected by the hydrodynamic injection method. Then, 8 µg of nanoparticle D2 was transfected with HBV and intravenously injected once. After 4 days of the injection, the mice were sacrificed to obtain a blood sample. The b-gal was used as an injection control. The mouse serum was diluted with PBS (at 1:50 for HBeAg and at 1:2000 for HBsAg). Viral proteins (HBeAg and HBsAg) were measured with an ELISA kit.

As a result, an antiviral effect was exhibited in the mice injected with the nanoparticle D2, as shown in FIGS. 23 (*b*) and (*c*). Herein, the first bar represents mock, the second bar represents HBV, the third bar represents HBV and chitosan nanoparticle D2, and the fourth bar represents HBV and chitosan nanoparticle D4. The chitosan nanoparticle D4 was used as a negative control that did not inhibit HBV at all. As shown in FIG. 23 (*d*), the antiviral effect was also exhibited at the HBV DNA level. These results confirmed that when the chitosan nanoparticle D2 was injected, it was delivered to the liver of the mice and strongly inhibited the virus activity.

Example 6: Inhibition of HBV cccDNA in PHH (Primary Human Hepatocyte)

6-1: Confirming that Modified D2 Inhibit HBV when Treated from the Beginning

In order to investigate whether the D2 oligonucleotides remove HBV cccDNA from PHH, an experiment was carried out by transfecting PHH with HBV. In this experiment, the cells were treated with the modified D2 oligonucleotides from the next day after the HBV transfection, and this method was schematized in FIG. 24 (a) as the procedure of transfecting PHH with HBV. At this time, IFN-α was used as a positive control, and unmodified D2 oligonucleotides were used as a negative control because they could not inhibit HBV at all when treated with the unmodified D2 oligonucleotides. The experiment was quantitatively performed using real-time PCR, and the results are shown in FIGS. 24 (d) and (e).

As a result, it was confirmed in FIGS. 24 (b) and (c) that when the cells were treated with the D2 oligonucleotides partially modified with PS-LNA (3,3), PS-LNA (4,4), and PS-LNA (all), HBeAg and HBsAg were decreased. In addition, as shown in FIG. 24 (d), HBV rcDNAs were efficiently reduced in the D2 oligonucleotides partially modified with PS-LNA (3,3), PS-LNA (4,4), and PS-LNA (all). In order to ultimately treat HBV, cccDNA must be removed. In this regard, HBV cccDNAs were reduced when the cells were treated with the D2 oligonucleotides partially modified with PS-LNA (3,3), PS-LNA (4,4), and PS-LNA (all), as shown in FIG. 24 (e).

6-2: Confirming that Modified D2 Oligonucleotides Inhibit HBV Even when Sufficient cccDNA is Generated In order to investigate whether the D2 oligonucleotides remove HBV cccDNA from PHH even under sufficient re-transfection conditions for 5 days after the HBV transfection, an experiment was carried out. In this experiment, the cells were treated with the modified D2 oligonucleotides (0.5 μM of PS-LNA (all), 1 μM of PS-LNA (all)) from 5 days after the HBV transfection, and this method was schematized in FIG. 25 (a) as the procedure of transfecting PHH with HBV. At this time, IFN-α was used as a positive control for inhibiting HBeAg, HBsAg, rcDNA, and cccDNA, and unmodified D2 oligonucleotides were used as a negative control because they could not inhibit HBV at all when the cells were treated with the unmodified D2 oligonucleotides.

As a result, FIGS. 25 (b) and (c) showed that HBeAg and HBsAg were decreased when the cells were treated with the modified D2 oligonucleotides at different concentrations. FIG. 25 (d) confirmed the difference in the amount of HBV DNA and cccDNA by DNA electrophoresis after performing general PCR. In addition, as shown in FIG. 25 (d), the HBV rcDNA and cccDNA were decreased in a concentration-dependent manner in the partially modified D2 oligonucleotides.

Example 7: Confirmation of G-Quadruplex Formed by D2 Oligonucleotides and HBV cccDNA in HepG2-NTCP In order to investigate whether the D2 oligonucleotides modified with PS-LNA efficiently recognize HBV cccDNA in HepG2-NTCP and form a G-quadruplex, NTCP cells were transfected with HBV and treated with the D2 oligonucleotides, and then observed under a microscope. In this experiment, the cells were treated with the modified D2 oligonucleotides from 5 days after the HBV transfection, and the cells were fixed on day 7. Then, a slide glass was prepared so as to display a red signal so that the G-quadruplex could be observed using BG4 antibodies.

As a result, FIG. 26 (a) confirmed that the D2 oligonucleotides and cccDNA formed a G-quadruplex by the BG4 antibody that recognizes the G-quadruplex when the cells were treated with HBV cccDNA produced from transfection in NTCP and the modified D2 oligonucleotides. In addition, by confirming that HBeAg was normally expressed in HBV, but the HBeAg level was reduced when treated with the modified D2, the antiviral effect of the modified D2 oligonucleotides was also examined. When the graphs shown in FIG. 26 (b) and the number of foci by BG4 summarized at the bottom of FIG. 26 (a) were examined, approximately five endogenous forms of G-quadruplex signals were identified under normal cell conditions, in the case of Mock. Approximately 6 signals were identified when the cells were treated with the modified D2 oligonucleotides alone. Approximately 7 signals were identified when the cells were transfected with HBV alone. Above all, approximately 16 signals were identified when the cells were treated with HBV and modified D2 oligonucleotides. These results showed that HBV cccDNA forms a G-quadruplex due to the modified D2 oligonucleotides.

The invention claimed is:

1. A method for treating hepatitis B, comprising: administering an effective dose of a pharmaceutical composition for treating hepatitis B comprising at least one oligonucleotide selected from the group consisting of an oligonucleotide represented by the nucleic acid sequence of SEQ ID NO: 2 or a nucleic acid sequence complementary thereto; and an oligonucleotide having at least one chemical modification on the oligonucleotide represented by the nucleic acid sequence of SEQ ID NO: 2 or a nucleic acid sequence complementary thereto, as an active ingredient, to an individual, wherein the oligonucleotide having a chemical modification has at least one chemically modified internucleoside linkage in which the phosphate group of a nucleotide is replaced with a phosphorothioate, phosphorodithioate, phosphoramidate, or boranophosphate group.

2. The method of claim 1, wherein the oligonucleotide having a chemical modification further has at least one chemically modified sugar moiety.

3. The method of claim 2, wherein the sugar moiety is modified such that the —H group at the 2' position of the pentose in a nucleotide is substituted with methoxyethyl (MOE), dimethylaminooxyethoxy (DMAOE), dimethylaminoethoxyethyl (DMAEOE), methyl (OMe), aminopropoxy (AP), or fluorine (F), or the sugar moiety is substituted with F-ANA.

4. The method of claim 2, wherein the sugar moiety is chemically modified in the form of LNA (locked nucleic acid) or PNA (peptide nucleic acid).

5. The method of claim 1, wherein the oligonucleotide is in a state where GalNAc (N-acetylgalactosamine) is bound to the 3' or 5' end via a linker.

6. The method of claim 1, wherein the oligonucleotide having a chemical modification has two or more chemical modifications selected from the group consisting of a chemical modification of the internucleoside linkage and a chemical modification of the sugar moiety.

7. The method of 6, wherein the oligonucleotide having two or more chemical modifications has a chemical modification in which the phosphate group of a nucleotide is replaced with phosphorothioate, phosphorodithioate, phosphoramidate, or boranophosphate, and further has a chemical modification in which the —H group at the 2' position of the pentose in a nucleotide is substituted with methoxyethyl (MOE), dimethylaminooxyethoxy (DMAOE), dimethylaminoethoxyethyl (DMAEOE), methyl (OMe), aminopropoxy (AP), or fluorine (F), or the sugar moiety of a nucleotide is substituted with F-ANA.

8. The method of claim 6, wherein the oligonucleotide having two or more chemical modifications has a chemical modification in which the phosphate group of a nucleotide is replaced with phosphorothioate, phosphorodithioate, phosphoramidate, or boranophosphate, and further has a chemical modification in which the sugar moiety is chemically modified in the form of LNA (locked nucleic acid) or PNA (peptide nucleic acid).

9. The method of claim 1, wherein the oligonucleotide forms a G-quadruplex with HBV.

10. The method of claim 1, wherein the composition for treating hepatitis B reduces cccDNA (covalently closed circular DNA) of HBV.

11. The method of claim 1, wherein the composition for treating hepatitis B further comprises a pharmaceutically acceptable carrier.

12. The method of claim 11, wherein the pharmaceutically acceptable carrier comprises chitosan nanoparticles, colloidal dispersion systems, polymer complexes, nanocapsules, nanoparticles, microspheres, beads, oil-in-water emulsions, micelles, mixed micelles, or liposomes.

13. The method of claim 12, wherein the pharmaceutically acceptable carrier is a chitosan nanoparticle, and the chitosan has a molecular weight of 50 kDa to 190 kDa.

14. The method of claim 1, wherein the composition for treating hepatitis B is administered orally, parenterally, intraperitoneally, intravenously, percutaneously, sublingually, intramuscularly, intranasally, or subcutaneously to an individual.

15. A method for screening a therapeutic agent for hepatitis B, comprising: contacting hepatitis B virus (HBV) with a candidate material and confirming whether the HBV forms a G-quadruplex with the candidate material.

16. The method of claim 15, further comprising selecting the candidate material as a therapeutic agent for hepatitis B if HBV forms a G-quadruplex with the candidate material.

17. The method of claim 15, wherein the formation of G-quadruplex is confirmed by a method selected from the group consisting of electrophoretic mobility shift assay (EMSA), circular dichroism (CD), nuclear magnetic resonance (NMR), and a method of using G-quadruplex-specific antibodies.

18. The method of claim 15, wherein the candidate material comprises 4 or more guanines (G).

19. The method of claim 15, wherein the G-quadruplex is formed by binding an enhancer II region having a nucleic acid sequence of SEQ ID NO: 19 of HBV with a candidate material.

* * * * *

SEQUENCE LISTING

<160> NUMBER OF SEQ ID NOS: 77

<210> SEQ ID NO 1
<211> LENGTH: 28
<212> TYPE: DNA
<213> ORGANISM: Artificial Sequence
<220> FEATURE:
<223> OTHER INFORMATION: Synthetic Construct

<400> SEQUENCE: 1
aagcctccaa gctgtgcctt gggtggct                28

<210> SEQ ID NO 2
<211> LENGTH: 16
<212> TYPE: DNA
<213> ORGANISM: Artificial Sequence

```
<220> FEATURE:
<223> OTHER INFORMATION: Synthetic Construct

<400> SEQUENCE: 2
tgctgggggg aattga                                                    16

<210> SEQ ID NO 3
<211> LENGTH: 16
<212> TYPE: DNA
<213> ORGANISM: Artificial Sequence
<220> FEATURE:
<223> OTHER INFORMATION: Synthetic Construct

<400> SEQUENCE: 3
tgctgggtgg aattga                                                    16

<210> SEQ ID NO 4
<211> LENGTH: 16
<212> TYPE: DNA
<213> ORGANISM: Artificial Sequence
<220> FEATURE:
<223> OTHER INFORMATION: Synthetic Construct

<400> SEQUENCE: 4
actagacact atttaa                                                    16

<210> SEQ ID NO 5
<211> LENGTH: 16
<212> TYPE: DNA
<213> ORGANISM: Artificial Sequence
<220> FEATURE:
<223> OTHER INFORMATION: Synthetic Construct

<400> SEQUENCE: 5
cgttgatgcc tttgta                                                    16

<210> SEQ ID NO 6
<211> LENGTH: 16
<212> TYPE: DNA
<213> ORGANISM: Artificial Sequence
<220> FEATURE:
<223> OTHER INFORMATION: Synthetic Construct

<400> SEQUENCE: 6
ttctaggggg aactac                                                    16

<210> SEQ ID NO 7
<211> LENGTH: 16
<212> TYPE: DNA
<213> ORGANISM: Artificial Sequence
<220> FEATURE:
<223> OTHER INFORMATION: Synthetic Construct

<400> SEQUENCE: 7
gatgtggtat tggggg                                                    16

<210> SEQ ID NO 8
<211> LENGTH: 16
<212> TYPE: DNA
<213> ORGANISM: Artificial Sequence
<220> FEATURE:
<223> OTHER INFORMATION: Synthetic Construct

<400> SEQUENCE: 8
aggagttggg ggagga                                                    16
```

<210> SEQ ID NO 9
<211> LENGTH: 16
<212> TYPE: DNA
<213> ORGANISM: Artificial Sequence
<220> FEATURE:
<223> OTHER INFORMATION: Synthetic Construct

<400> SEQUENCE: 9
cataaggtgg ggaact                                                    16

<210> SEQ ID NO 10
<211> LENGTH: 19
<212> TYPE: DNA
<213> ORGANISM: Artificial Sequence
<220> FEATURE:
<223> OTHER INFORMATION: Synthetic Construct

<400> SEQUENCE: 10
ctccccgtct gtgccttct                                                 19

<210> SEQ ID NO 11
<211> LENGTH: 18
<212> TYPE: DNA
<213> ORGANISM: Artificial Sequence
<220> FEATURE:
<223> OTHER INFORMATION: Synthetic Construct

<400> SEQUENCE: 11
gccccaaagc cacccaag                                                  18

<210> SEQ ID NO 12
<211> LENGTH: 19
<212> TYPE: DNA
<213> ORGANISM: Artificial Sequence
<220> FEATURE:
<223> OTHER INFORMATION: Synthetic Construct

<400> SEQUENCE: 12
ctcgtggtgg acttctctc                                                 19

<210> SEQ ID NO 13
<211> LENGTH: 18
<212> TYPE: DNA
<213> ORGANISM: Artificial Sequence
<220> FEATURE:
<223> OTHER INFORMATION: Synthetic Construct

<400> SEQUENCE: 13
ctgcaggatg aagaggaa                                                  18

<210> SEQ ID NO 14
<211> LENGTH: 25
<212> TYPE: DNA
<213> ORGANISM: Artificial Sequence
<220> FEATURE:
<223> OTHER INFORMATION: Synthetic Construct

<400> SEQUENCE: 14
gttcacggtg gtctccatgc aacgt                                          25

<210> SEQ ID NO 15
<211> LENGTH: 25
<212> TYPE: DNA
<213> ORGANISM: Artificial Sequence
<220> FEATURE:
<223> OTHER INFORMATION: Synthetic Construct

<400> SEQUENCE: 15
aggtgaagcg aagtgcacac ggacc                                        25

<210> SEQ ID NO 16
<211> LENGTH: 25
<212> TYPE: DNA
<213> ORGANISM: Artificial Sequence
<220> FEATURE:
<223> OTHER INFORMATION: Synthetic Construct

<400> SEQUENCE: 16
cactcaccaa cctcctgtcc tccaa                                        25

<210> SEQ ID NO 17
<211> LENGTH: 26
<212> TYPE: DNA
<213> ORGANISM: Artificial Sequence
<220> FEATURE:
<223> OTHER INFORMATION: Synthetic Construct

<400> SEQUENCE: 17
tgtcctggtt atcgctggat gtgtct                                       26

<210> SEQ ID NO 18
<211> LENGTH: 398
<212> TYPE: DNA
<213> ORGANISM: Artificial Sequence
<220> FEATURE:
<223> OTHER INFORMATION: Synthetic Construct

<400> SEQUENCE: 18
aaattgcctg taaatagacc tattgattgg aaagtatgtc aaagaattgt gggtcttttg     60
ggctttgctg cccctttac acaatgtggc tatcctgctt tgatgccttt atatgcatgt    120
atacaatcta agcaggcttt cactttctcg ccaacttaca aggcctttct gtgtaaacaa   180
tatctgcacc tttaccccgt tgcccggcaa cggtcaggtc tctgccaagt gtttgctgac   240
gcaaccccca ctggatgggg cttggccatt ggccatcggc gcatgcgtgg aacctttgtg   300
gctcctctgc cgatccatac cgcggaactc ctagcggctt gttttgctcg cagccggtct   360
ggagcgaaac ttatcgggac tgacaactct gttgtcct                          398

<210> SEQ ID NO 19
<211> LENGTH: 212
<212> TYPE: DNA
<213> ORGANISM: Artificial Sequence
<220> FEATURE:
<223> OTHER INFORMATION: Synthetic Construct

<400> SEQUENCE: 19
cgcttcacct ctgcacgtcg catggagacc accgtgaacg cccaccaggt cttgcccaag     60
gtcttacata agaggactct tggactctca gcaatgtcaa cgaccgacct tgaggcatac   120
ttcaaagact gtttgtttaa agactgggag gagttggggg aggagattag gttaaaggtc   180
tttgtattag gaggctgtag gcataaattg gt                                212

<210> SEQ ID NO 20
<211> LENGTH: 16
<212> TYPE: DNA
<213> ORGANISM: Artificial Sequence
<220> FEATURE:
<223> OTHER INFORMATION: Synthetic Construct
<220> FEATURE:

<220> FEATURE:
<221> NAME/KEY: misc_feature
<222> LOCATION: (1)..(1)
<223> OTHER INFORMATION: T represents a 2'OMe thymidine wherein phosphate of T is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)
<223> OTHER INFORMATION: T represents a 2'OMe thymidine.
<220> FEATURE:
<221> NAME/KEY: misc_feature
<222> LOCATION: (5)..(5)
<223> OTHER INFORMATION: G represents a 2'OMe guanosine.
<220> FEATURE:
<221> NAME/KEY: misc_feature
<222> LOCATION: (6)..(7)
<223> OTHER INFORMATION: G represents a guanosine of locked nucleic acid.
<220> FEATURE:
<221> NAME/KEY: misc_feature
<222> LOCATION: (8)..(10)
<223> OTHER INFORMATION: G represents a 2'OMe guanosine.
<220> FEATURE:
<221> NAME/KEY: misc_feature
<222> LOCATION: (11)..(12)
<223> OTHER INFORMATION: A represents a 2'OMe adenosine.
<220> FEATURE:
<221> NAME/KEY: misc_feature
<222> LOCATION: (13)..(14)
<223> OTHER INFORMATION: T represents a 2'OMe thymidine.
<220> FEATURE:
<221> NAME/KEY: misc_feature
<222> LOCATION: (15)..(15)
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a 2'OMe adenosine wherein phosphate of A is a modified as phosphorothioate.

<400> SEQUENCE: 20
tgctgggggg aattga                                              16

<210> SEQ ID NO 21
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a 2'OMe thymidine wherein phosphate of T is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)
<223> OTHER INFORMATION: T represents a 2'OMe thymidine.
<220> FEATURE:
<221> NAME/KEY: misc_feature
<222> LOCATION: (5)..(8)
<223> OTHER INFORMATION: G represents a guanosine of locked nucleic acid.
<220> FEATURE:
<221> NAME/KEY: misc_feature
<222> LOCATION: (9)..(10)
<223> OTHER INFORMATION: G represents a 2'OMe guanosine.
<220> FEATURE:
<221> NAME/KEY: misc_feature
<222> LOCATION: (11)..(12)
<223> OTHER INFORMATION: A represents a 2'OMe adenosine.
<220> FEATURE:
<221> NAME/KEY: misc_feature
<222> LOCATION: (13)..(14)
<223> OTHER INFORMATION: T represents a 2'OMe thymidine.
<220> FEATURE:
<221> NAME/KEY: misc_feature
<222> LOCATION: (15)..(15)
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a 2'OMe adenosine wherein
      phosphate of A is a modified as phosphorothioate.

<400> SEQUENCE: 21
tgctgggggg aattga                                                   16

<210> SEQ ID NO 22
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a 2'OMe thymidine wherein
      phosphate of T is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)
<223> OTHER INFORMATION: T represents a 2'OMe thymidine.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(12)
<223> OTHER INFORMATION: A represents a 2'OMe adenosine.
<220> FEATURE:
<221> NAME/KEY: misc_feature
<222> LOCATION: (13)..(14)
<223> OTHER INFORMATION: T represents a 2'OMe thymidine.
<220> FEATURE:
<221> NAME/KEY: misc_feature
<222> LOCATION: (15)..(15)
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a 2'OMe adenosine wherein
      phosphate of A is a modified as phosphorothioate.

<400> SEQUENCE: 22 tgctggggggg aattga                                                  16

```
<210> SEQ ID NO 23
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a 2'OMe thymidine wherein
      phosphate of T is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(11)
<223> OTHER INFORMATION: A represents a adenosine of locked nucleic
      acid.
<220> FEATURE:
<221> NAME/KEY: misc_feature
<222> LOCATION: (12)..(12)
<223> OTHER INFORMATION: A represents a 2'OMe adenosine.
<220> FEATURE:
<221> NAME/KEY: misc_feature
<222> LOCATION: (13)..(14)
<223> OTHER INFORMATION: T represents a 2'OMe thymidine.
<220> FEATURE:
<221> NAME/KEY: misc_feature
<222> LOCATION: (15)..(15)
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a 2'OMe adenosine wherein
      phosphate of A is a modified as phosphorothioate.

<400> SEQUENCE: 23
tgctgggggg aattga                                                 16

<210> SEQ ID NO 24
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a 2'OMe thymidine wherein
      phosphate of T is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)
```

```
<223> OTHER INFORMATION: T represents a thymidine of locked nucleic
      acid.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(13)
<223> OTHER INFORMATION: T represents a thymidine of locked nucleic
      acid.
<220> FEATURE:
<221> NAME/KEY: misc_feature
<222> LOCATION: (14)..(14)
<223> OTHER INFORMATION: T represents a 2'OMe thymidine.
<220> FEATURE:
<221> NAME/KEY: misc_feature
<222> LOCATION: (15)..(15)
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a 2'OMe adenosine wherein
      phosphate of A is a modified as phosphorothioate.

<400> SEQUENCE: 24
tgctgggggg aattga                                                  16

<210> SEQ ID NO 25
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a 2'OMe thymidine wherein
      phosphate of T is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a 2'OMe guanosine.
```

```
<220> FEATURE:
<221> NAME/KEY: misc_feature
<222> LOCATION: (16)..(16)
<223> OTHER INFORMATION: A represents a 2'OMe adenosine wherein
      phosphate of A is a modified as phosphorothioate.

<400> SEQUENCE: 25
tgctgggggg aattga                                                   16

<210> SEQ ID NO 26
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)
<223> OTHER INFORMATION: T represents a 2'OMe thymidine.
<220> FEATURE:
<221> NAME/KEY: misc_feature
<222> LOCATION: (5)..(10)
<223> OTHER INFORMATION: G represents a 2'OMe guanosine.
<220> FEATURE:
<221> NAME/KEY: misc_feature
<222> LOCATION: (11)..(12)
<223> OTHER INFORMATION: A represents a 2'OMe adenosine.
<220> FEATURE:
<221> NAME/KEY: misc_feature
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 26
tgctgggggg aattga                                                   16

<210> SEQ ID NO 27
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
```

```
          acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a 2'OMe thymidine.
<220> FEATURE:
<221> NAME/KEY: misc_feature
<222> LOCATION: (5)..(10)
<223> OTHER INFORMATION: G represents a 2'OMe guanosine.
<220> FEATURE:
<221> NAME/KEY: misc_feature
<222> LOCATION: (11)..(11)
<223> OTHER INFORMATION: A represents a 2'OMe adenosine.
<220> FEATURE:
<221> NAME/KEY: misc_feature
<222> LOCATION: (12)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 27
tgctgggggg aattga                                                    16

<210> SEQ ID NO 28
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (5)..(10)
<223> OTHER INFORMATION: G represents a 2'OMe guanosine.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
```

```
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 28
tgctgggggg aattga                                                       16

<210> SEQ ID NO 29
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (5)..(5)
<223> OTHER INFORMATION: G represents a guanosine of locked nucleic
      acid.
<220> FEATURE:
<221> NAME/KEY: misc_feature
<222> LOCATION: (6)..(9)
<223> OTHER INFORMATION: G represents a 2'OMe guanosine.
<220> FEATURE:
<221> NAME/KEY: misc_feature
<222> LOCATION: (10)..(10)
<223> OTHER INFORMATION: G represents a guanosine of locked nucleic
      acid.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.
```

<400> SEQUENCE: 29
tgctgggggg aattga                                                        16

<210> SEQ ID NO 30
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (5)..(6)
<223> OTHER INFORMATION: G represents a guanosine of locked nucleic
      acid.
<220> FEATURE:
<221> NAME/KEY: misc_feature
<222> LOCATION: (7)..(8)
<223> OTHER INFORMATION: G represents a 2'OMe guanosine.
<220> FEATURE:
<221> NAME/KEY: misc_feature
<222> LOCATION: (9)..(10)
<223> OTHER INFORMATION: G represents a guanosine of locked nucleic
      acid.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 30
tgctgggggg aattga                                                        16

<210> SEQ ID NO 31
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)

```
<223> OTHER INFORMATION: T represents a thymidine wherein phosphate of T
      is modified as phosphorothioate.
<220> FEATURE:
<221> NAME/KEY: misc_feature
<222> LOCATION: (7)..(8)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine wherein phosphate of A
      is modified as phosphorothioate.

<400> SEQUENCE: 31
tgctgggggg aattga                                                    16

<210> SEQ ID NO 32
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(9)
<223> OTHER INFORMATION: G represents a guanosine of locked nucleic
      acid.
<220> FEATURE:
<221> NAME/KEY: misc_feature
<222> LOCATION: (11)..(1)
<223> OTHER INFORMATION: T represents a thymidine wherein phosphate of T
      is modified as phosphorothioate.
<220> FEATURE:
<221> NAME/KEY: misc_feature
<222> LOCATION: (16)..(16)
<223> OTHER INFORMATION: A represents a adenosine wherein phosphate of A
      is modified as phosphorothioate.

<400> SEQUENCE: 32
tgctgggggg aattga                                                    16

<210> SEQ ID NO 33
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine wherein phosphate of T
      is modified as phosphorothioate.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine wherein phosphate of A
      is modified as phosphorothioate.

<400> SEQUENCE: 33
tgctgggggg aattga                                                    16

<210> SEQ ID NO 34
<211> LENGTH: 16
<212> TYPE: DNA
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: (1)..(1)
<223> OTHER INFORMATION: T represents a thymidine wherein phosphate of T
      is modified as phosphorothioate.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(11)
<223> OTHER INFORMATION: A represents a adenosine of locked nucleic
      acid.
<220> FEATURE:
<221> NAME/KEY: misc_feature
<222> LOCATION: (16)..(16)
<223> OTHER INFORMATION: A represents a adenosine wherein phosphate of A
      is modified as phosphorothioate.

<400> SEQUENCE: 34
tgctgggggg aattga                                                    16

<210> SEQ ID NO 35
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine wherein phosphate of T
      is modified as phosphorothioate.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(13)
<223> OTHER INFORMATION: T represents a thymidine of locked nucleic
      acid.
<220> FEATURE:
<221> NAME/KEY: misc_feature
<222> LOCATION: (16)..(16)
<223> OTHER INFORMATION: A represents a adenosine wherein phosphate of A
      is modified as phosphorothioate.

<400> SEQUENCE: 35
tgctgggggg aattga                                                    16

<210> SEQ ID NO 36
<211> LENGTH: 16
<212> TYPE: DNA
<213> ORGANISM: Artificial Sequence
<220> FEATURE:
<223> OTHER INFORMATION: Synthetic Construct
<220> FEATURE:
```

<221> NAME/KEY: misc_feature
<222> LOCATION: (1)..(1)
<223> OTHER INFORMATION: T represents a thymidine wherein phosphate of T
       is modified as phosphorothioate.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic
       acid.
<220> FEATURE:
<221> NAME/KEY: misc_feature
<222> LOCATION: (5)..(10)
<223> OTHER INFORMATION: G represents a guanosine of locked nucleic
       acid.
<220> FEATURE:
<221> NAME/KEY: misc_feature
<222> LOCATION: (11)..(12)
<223> OTHER INFORMATION: A represents a adenosine of locked nucleic
       acid.
<220> FEATURE:
<221> NAME/KEY: misc_feature
<222> LOCATION: (13)..(14)
<223> OTHER INFORMATION: T represents a thymidine of locked nucleic
       acid.
<220> FEATURE:
<221> NAME/KEY: misc_feature
<222> LOCATION: (16)..(16)
<223> OTHER INFORMATION: A represents a adenosine wherein phosphate of A
       is modified as phosphorothioate.

<400> SEQUENCE: 36
tgctgggggg aattga                                                 16

<210> SEQ ID NO 37
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
       wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
       acid.
<220> FEATURE:
<221> NAME/KEY: misc_feature
<222> LOCATION: (13)..(14)
<223> OTHER INFORMATION: T represents a thymidine of locked nucleic
       acid.
<220> FEATURE:
<221> NAME/KEY: misc_feature
<222> LOCATION: (15)..(15)
<223> OTHER INFORMATION: G represents a guanosine of locked nucleic
       acid.
<220> FEATURE:
<221> NAME/KEY: misc_feature
<222> LOCATION: (16)..(16)
<223> OTHER INFORMATION: A represents a adenosine of locked nucleic acid
       wherein phosphate of A is modified as phosphorothioate.

<400> SEQUENCE: 37
tgctggggcg aattga                                                 16

<210> SEQ ID NO 38
<211> LENGTH: 16
<212> TYPE: DNA

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (12)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 38
tgctgggggg aattga                                                     16

<210> SEQ ID NO 39
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic
      acid.
<220> FEATURE:
```

<221> NAME/KEY: misc_feature
<222> LOCATION: (15)..(15)
<223> OTHER INFORMATION: G represents a guanosine of locked nucleic acid.
<220> FEATURE:
<221> NAME/KEY: misc_feature
<222> LOCATION: (16)..(16)
<223> OTHER INFORMATION: A represents a adenosine of locked nucleic acid wherein phosphate of A is modified as phosphorothioate.

<400> SEQUENCE: 39
tgctgggggg aattga          16

<210> SEQ ID NO 40
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic acid.
<220> FEATURE:
<221> NAME/KEY: misc_feature
<222> LOCATION: (5)..(5)
<223> OTHER INFORMATION: G represents a guanosine of locked nucleic acid.
<220> FEATURE:
<221> NAME/KEY: misc_feature
<222> LOCATION: (10)..(10)
<223> OTHER INFORMATION: G represents a guanosine of locked nucleic acid.
<220> FEATURE:
<221> NAME/KEY: misc_feature
<222> LOCATION: (11)..(12)
<223> OTHER INFORMATION: A represents a adenosine of locked nucleic acid.
<220> FEATURE:
<221> NAME/KEY: misc_feature
<222> LOCATION: (13)..(14)
<223> OTHER INFORMATION: T represents a thymidine of locked nucleic acid.
<220> FEATURE:
<221> NAME/KEY: misc_feature
<222> LOCATION: (15)..(15)
<223> OTHER INFORMATION: G represents a guanosine of locked nucleic acid.
<220> FEATURE:
<221> NAME/KEY: misc_feature
<222> LOCATION: (16)..(16)
<223> OTHER INFORMATION: A represents a adenosine of locked nucleic acid wherein phosphate of A is modified as phosphorothioate.

<400> SEQUENCE: 40
tgctgggggg aattga          16

<210> SEQ ID NO 41
<211> LENGTH: 16
<212> TYPE: DNA

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (5)..(6)
<223> OTHER INFORMATION: G represents a guanosine of locked nucleic
      acid.
<220> FEATURE:
<221> NAME/KEY: misc_feature
<222> LOCATION: (9)..(10)
<223> OTHER INFORMATION: G represents a guanosine of locked nucleic
      acid.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 41
tgctgggggg aattga                                                   16

<210> SEQ ID NO 42
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
```

```
<222> LOCATION: (4)..(4)
<223> OTHER INFORMATION: T represents a 2'OMe thymidine.
<220> FEATURE:
<221> NAME/KEY: misc_feature
<222> LOCATION: (5)..(5)
<223> OTHER INFORMATION: G represents a guanosine of locked nucleic
      acid.
<220> FEATURE:
<221> NAME/KEY: misc_feature
<222> LOCATION: (6)..(6)
<223> OTHER INFORMATION: G represents a 2'OMe guanosine.
<220> FEATURE:
<221> NAME/KEY: misc_feature
<222> LOCATION: (7)..(7)
<223> OTHER INFORMATION: G represents a guanosine of locked nucleic
      acid.
<220> FEATURE:
<221> NAME/KEY: misc_feature
<222> LOCATION: (8)..(8)
<223> OTHER INFORMATION: G represents a 2'OMe guanosine.
<220> FEATURE:
<221> NAME/KEY: misc_feature
<222> LOCATION: (9)..(9)
<223> OTHER INFORMATION: G represents a guanosine of locked nucleic
      acid.
<220> FEATURE:
<221> NAME/KEY: misc_feature
<222> LOCATION: (10)..(10)
<223> OTHER INFORMATION: G represents a 2'OMe guanosine.
<220> FEATURE:
<221> NAME/KEY: misc_feature
<222> LOCATION: (11)..(11)
<223> OTHER INFORMATION: A represents a adenosine of locked nucleic
      acid.
<220> FEATURE:
<221> NAME/KEY: misc_feature
<222> LOCATION: (12)..(12)
<223> OTHER INFORMATION: A represents a 2'OMe adenosine.
<220> FEATURE:
<221> NAME/KEY: misc_feature
<222> LOCATION: (13)..(13)
<223> OTHER INFORMATION: T represents a thymidine of locked nucleic
      acid.
<220> FEATURE:
<221> NAME/KEY: misc_feature
<222> LOCATION: (14)..(14)
<223> OTHER INFORMATION: T represents a 2'OMe thymidine.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a 2'OMe adenosine wherein
      phosphate of A is modified as phosphorothioate.

<400> SEQUENCE: 42
tgctgggggg aattga                                              16

<210> SEQ ID NO 43
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a 2'OMe thymidine wherein
      phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
```

```
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (5)..(5)
<223> OTHER INFORMATION: G represents a 2'OMe guanosine.
<220> FEATURE:
<221> NAME/KEY: misc_feature
<222> LOCATION: (6)..(6)
<223> OTHER INFORMATION: G represents a guanosine of locked nucleic
      acid.
<220> FEATURE:
<221> NAME/KEY: misc_feature
<222> LOCATION: (7)..(7)
<223> OTHER INFORMATION: G represents a 2'OMe guanosine.
<220> FEATURE:
<221> NAME/KEY: misc_feature
<222> LOCATION: (8)..(8)
<223> OTHER INFORMATION: G represents a guanosine of locked nucleic
      acid.
<220> FEATURE:
<221> NAME/KEY: misc_feature
<222> LOCATION: (9)..(9)
<223> OTHER INFORMATION: G represents a 2'OMe guanosine.
<220> FEATURE:
<221> NAME/KEY: misc_feature
<222> LOCATION: (10)..(10)
<223> OTHER INFORMATION: G represents a guanosine of locked nucleic
      acid.
<220> FEATURE:
<221> NAME/KEY: misc_feature
<222> LOCATION: (11)..(11)
<223> OTHER INFORMATION: A represents a 2'OMe adenosine.
<220> FEATURE:
<221> NAME/KEY: misc_feature
<222> LOCATION: (12)..(12)
<223> OTHER INFORMATION: A represents a adenosine of locked nucleic
      acid.
<220> FEATURE:
<221> NAME/KEY: misc_feature
<222> LOCATION: (13)..(13)
<223> OTHER INFORMATION: T represents a 2'OMe thymidine.
<220> FEATURE:
<221> NAME/KEY: misc_feature
<222> LOCATION: (14)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 43
tgctgggggg aattga                                                    16

<210> SEQ ID NO 44
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
``` wherein phosphate of T is modified as phosphorothioate.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (5)..(5)
<223> OTHER INFORMATION: G represents a guanosine of locked nucleic
        acid.
<220> FEATURE:
<221> NAME/KEY: misc_feature
<222> LOCATION: (7)..(7)
<223> OTHER INFORMATION: G represents a guanosine of locked nucleic
        acid.
<220> FEATURE:
<221> NAME/KEY: misc_feature
<222> LOCATION: (9)..(9)
<223> OTHER INFORMATION: G represents a guanosine of locked nucleic
        acid.
<220> FEATURE:
<221> NAME/KEY: misc_feature
<222> LOCATION: (11)..(11)
<223> OTHER INFORMATION: A represents a adenosine of locked nucleic
        acid.
<220> FEATURE:
<221> NAME/KEY: misc_feature
<222> LOCATION: (13)..(13)
<223> OTHER INFORMATION: T represents a thymidine of locked nucleic
        acid.
<220> FEATURE:
<221> NAME/KEY: misc_feature
<222> LOCATION: (15)..(15)
<223> OTHER INFORMATION: G represents a guanosine of locked nucleic
        acid.
<220> FEATURE:
<221> NAME/KEY: misc_feature
<222> LOCATION: (16)..(16)
<223> OTHER INFORMATION: A represents a adenosine wherein phosphate of A
        is modified as phosphorothioate.

<400> SEQUENCE: 44
tgctgggggg aattga                                                     16

<210> SEQ ID NO 45
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine wherein phosphate of T
        is modified as phosphorothioate.
<220> FEATURE:
<221> NAME/KEY: misc_feature
<222> LOCATION: (2)..(2)
<223> OTHER INFORMATION: G represents a guanosine of locked nucleic
        acid.
<220> FEATURE:
<221> NAME/KEY: misc_feature
<222> LOCATION: (4)..(4)
<223> OTHER INFORMATION: T represents a thymidine of locked nucleic
        acid.
<220> FEATURE:
<221> NAME/KEY: misc_feature
<222> LOCATION: (6)..(6)
<223> OTHER INFORMATION: G represents a guanosine of locked nucleic
        acid.
<220> FEATURE:
<221> NAME/KEY: misc_feature
<222> LOCATION: (8)..(8)
<223> OTHER INFORMATION: G represents a guanosine of locked nucleic
        acid.
<220> FEATURE:
<221> NAME/KEY: misc_feature
<222> LOCATION: (10)..(10)
<223> OTHER INFORMATION: G represents a guanosine of locked nucleic
      acid.
<220> FEATURE:
<221> NAME/KEY: misc_feature
<222> LOCATION: (12)..(12)
<223> OTHER INFORMATION: A represents a adenosine of locked nucleic
      acid.
<220> FEATURE:
<221> NAME/KEY: misc_feature
<222> LOCATION: (14)..(14)
<223> OTHER INFORMATION: T represents a thymidine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 45
tgctgggggg aattga                                                    16

<210> SEQ ID NO 46
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a 2'OMe thymidine wherein
      phosphate of T is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)
<223> OTHER INFORMATION: T represents a 2'OMe thymidine.
<220> FEATURE:
<221> NAME/KEY: misc_feature
<222> LOCATION: (5)..(10)
<223> OTHER INFORMATION: G represents a 2'OMe guanosine.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 46
tgctgggggg aattga                                                    16

<210> SEQ ID NO 47
<211> LENGTH: 16

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(12)
<223> OTHER INFORMATION: A represents a 2'OMe adenosine.
<220> FEATURE:
<221> NAME/KEY: misc_feature
<222> LOCATION: (13)..(14)
<223> OTHER INFORMATION: T represents a 2'OMe thymidine.
<220> FEATURE:
<221> NAME/KEY: misc_feature
<222> LOCATION: (15)..(15)
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a 2'OMe adenosine wherein
      phosphate of A is modified as phosphorothioate.

<400> SEQUENCE: 47
tgctgggggg aattga                                                   16

<210> SEQ ID NO 48
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine wherein phosphate of T
      is modified as phosphorothioate.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
```

```
<222> LOCATION: (16)..(16)
<223> OTHER INFORMATION: A represents a adenosine of locked nucleic acid
      wherein phosphate of A is modified as phosphorothioate.

<400> SEQUENCE: 48
tgctgggggg aattga                                               16

<210> SEQ ID NO 49
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine wherein phosphate of A
      is modified as phosphorothioate.

<400> SEQUENCE: 49 tgctggggggg aattga                                              16

<210> SEQ ID NO 50
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a 2'OMe thymidine wherein
      phosphate of T is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)
<223> OTHER INFORMATION: T represents a 2'OMe thymidine.
<220> FEATURE:
<221> NAME/KEY: misc_feature
<222> LOCATION: (5)..(10)
<223> OTHER INFORMATION: G represents a 2'OMe guanosine.
<220> FEATURE:
<221> NAME/KEY: misc_feature
```

```
<222> LOCATION: (16)..(16)
<223> OTHER INFORMATION: A represents a adenosine wherein phosphate of A
      is modified as phosphorothioate.

<400> SEQUENCE: 50
tgctgggggg aattga                                                    16

<210> SEQ ID NO 51
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine wherein phosphate of T
      is modified as phosphorothioate.
<220> FEATURE:
<221> NAME/KEY: misc_feature
<222> LOCATION: (11)..(12)
<223> OTHER INFORMATION: A represents a 2'OMe adenosine.
<220> FEATURE:
<221> NAME/KEY: misc_feature
<222> LOCATION: (13)..(14)
<223> OTHER INFORMATION: T represents a 2'OMe thymidine.
<220> FEATURE:
<221> NAME/KEY: misc_feature
<222> LOCATION: (15)..(15)
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a 2'OMe adenosine wherein
      phosphate of A is modified as phosphorothioate.

<400> SEQUENCE: 51
tgctgggggg aattga                                                    16

<210> SEQ ID NO 52
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a 2'OMe thymidine wherein
      phosphate of T is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)
<223> OTHER INFORMATION: T represents a 2'OMe thymidine.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine wherein phosphate of A
      is modified as phosphorothioate.

<400> SEQUENCE: 52
```

```
tgctgggggg aattga                                                          16

<210> SEQ ID NO 53
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a 2'OMe thymidine wherein
      phosphate of T is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)
<223> OTHER INFORMATION: T represents a 2'OMe thymidine.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 53
tgctgggggg aattga                                                          16

<210> SEQ ID NO 54
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine wherein phosphate of T
      is modified as phosphorothioate.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(12)
<223> OTHER INFORMATION: A represents a 2'OMe adenosine.
<220> FEATURE:
<221> NAME/KEY: misc_feature
<222> LOCATION: (13)..(14)
<223> OTHER INFORMATION: T represents a 2'OMe thymidine.
<220> FEATURE:
<221> NAME/KEY: misc_feature
<222> LOCATION: (15)..(15)
```

```
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a 2'OMe adenosine wherein
      phosphate of A is modified as phosphorothioate.

<400> SEQUENCE: 54
tgctgggggg aattga                                                    16

<210> SEQ ID NO 55
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine wherein phosphate of T
      is modified as phosphorothioate.
<220> FEATURE:
<221> NAME/KEY: misc_feature
<222> LOCATION: (5)..(10)
<223> OTHER INFORMATION: G represents a 2'OMe guanosine.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 55
tgctgggggg aattga                                                    16

<210> SEQ ID NO 56
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
```

```
<221> NAME/KEY: misc_feature
<222> LOCATION: (5)..(10)
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a adenosine wherein phosphate of A
      is modified as phosphorothioate.

<400> SEQUENCE: 56
tgctgggggg aattga                                                      16

<210> SEQ ID NO 57
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (11)..(12)
<223> OTHER INFORMATION: A represents a 2'OMe adenosine.
<220> FEATURE:
<221> NAME/KEY: misc_feature
<222> LOCATION: (13)..(14)
<223> OTHER INFORMATION: T represents a 2'OMe thymidine.
<220> FEATURE:
<221> NAME/KEY: misc_feature
<222> LOCATION: (15)..(15)
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a 2'OMe adenosine wherein
      phosphate of A is modified as phosphorothioate.

<400> SEQUENCE: 57
tgctgggggg aattga                                                      16

<210> SEQ ID NO 58
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
```

```
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 58
tgctgggggg aattga                                                     16

<210> SEQ ID NO 59
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic
      acid.
```

```
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 59
tgctgggggg aattga                                                     16

<210> SEQ ID NO 60
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a 2'OMe thymidine wherein
      phosphate of T is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)
<223> OTHER INFORMATION: T represents a 2'OMe thymidine.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(12)
<223> OTHER INFORMATION: A represents a 2'OMe adenosine.
<220> FEATURE:
<221> NAME/KEY: misc_feature
<222> LOCATION: (13)..(14)
<223> OTHER INFORMATION: T represents a 2'OMe thymidine.
<220> FEATURE:
<221> NAME/KEY: misc_feature
<222> LOCATION: (15)..(15)
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a 2'OMe adenosine wherein
      phosphate of A is modified as phosphorothioate.

<400> SEQUENCE: 60
tgctgggggg aattga                                                     16

<210> SEQ ID NO 61
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
```

```
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic
      acid.
<220> FEATURE:
<221> NAME/KEY: misc_feature
<222> LOCATION: (5)..(10)
<223> OTHER INFORMATION: G represents a 2'OMe guanosine.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 61
tgctgggggg aattga                                                    16

<210> SEQ ID NO 62
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine wherein phosphate of T
      is modified as phosphorothioate.
<220> FEATURE:
<221> NAME/KEY: misc_feature
<222> LOCATION: (4)..(4)
<223> OTHER INFORMATION: T represents a thymidine wherein phosphate of T
      is modified as phosphorothioate.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(11)
<223> OTHER INFORMATION: A represents a adenosine wherein phosphate of A
      is modified as phosphorothioate.
<220> FEATURE:
<221> NAME/KEY: misc_feature
<222> LOCATION: (16)..(16)
<223> OTHER INFORMATION: A represents a adenosine wherein phosphate of A
      is modified as phosphorothioate.

<400> SEQUENCE: 62
tgctgggggg aattga                                                    16
```

<210> SEQ ID NO 63
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic acid wherein phosphate of T is modified as phosphorothioate.
<220> FEATURE:
<221> NAME/KEY: misc_feature
<222> LOCATION: (11)..(11)
<223> OTHER INFORMATION: A represents a adenosine of locked nucleic acid wherein phosphate of A is modified as phosphorothioate.
<220> FEATURE:
<221> NAME/KEY: misc_feature
<222> LOCATION: (12)..(12)
<223> OTHER INFORMATION: A represents a adenosine of locked nucleic acid.
<220> FEATURE:
<221> NAME/KEY: misc_feature
<222> LOCATION: (13)..(14)
<223> OTHER INFORMATION: T represents a thymidine of locked nucleic acid.
<220> FEATURE:
<221> NAME/KEY: misc_feature
<222> LOCATION: (15)..(15)
<223> OTHER INFORMATION: G represents a guanosine of locked nucleic acid.
<220> FEATURE:
<221> NAME/KEY: misc_feature
<222> LOCATION: (16)..(16)
<223> OTHER INFORMATION: A represents a adenosine of locked nucleic acid wherein phosphate of A is modified as phosphorothioate.

<400> SEQUENCE: 63
tgctgggggg aattga         16

<210> SEQ ID NO 64
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a 2'OMe thymidine wherein phosphate of T is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)

```
<223> OTHER INFORMATION: T represents a 2'OMe thymidine wherein
      phosphate of T is modified as phosphorothioate.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(11)
<223> OTHER INFORMATION: A represents a adenosine wherein phosphate of A
      is modified as phosphorothioate.
<220> FEATURE:
<221> NAME/KEY: misc_feature
<222> LOCATION: (16)..(16)
<223> OTHER INFORMATION: A represents a adenosine wherein phosphate of A
      is modified as phosphorothioate.

<400> SEQUENCE: 64
tgctgggggg aattga                                                    16

<210> SEQ ID NO 65
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a 2'OMe thymidine wherein
      phosphate of T is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)
<223> OTHER INFORMATION: T represents a 2'OMe thymidine wherein
      phosphate of T is modified as phosphorothioate.
<220> FEATURE:
<221> NAME/KEY: misc_feature
<222> LOCATION: (11)..(11)
<223> OTHER INFORMATION: A represents a adenosine of locked nucleic acid
      wherein phosphate of A is modified as phosphorothioate.
<220> FEATURE:
<221> NAME/KEY: misc_feature
<222> LOCATION: (12)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: T represents a thymidine of locked nucleic acid
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 65
tgctgggggg aattga                                                    16

<210> SEQ ID NO 66
<211> LENGTH: 16
```

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine wherein phosphate of T
      is modified as phosphorothioate.
<220> FEATURE:
<221> NAME/KEY: misc_feature
<222> LOCATION: (4)..(4)
<223> OTHER INFORMATION: T represents a thymidine wherein phosphate of T
      is modified as phosphorothioate.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(11)
<223> OTHER INFORMATION: A represents a 2'OMe adenosine wherein
      phosphate of A is modified as phosphorothioate.
<220> FEATURE:
<221> NAME/KEY: misc_feature
<222> LOCATION: (12)..(12)
<223> OTHER INFORMATION: A represents a 2'OMe adenosine.
<220> FEATURE:
<221> NAME/KEY: misc_feature
<222> LOCATION: (13)..(14)
<223> OTHER INFORMATION: T represents a 2'OMe thymidine.
<220> FEATURE:
<221> NAME/KEY: misc_feature
<222> LOCATION: (15)..(15)
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a 2'OMe adenosine wherein
      phosphate of A is modified as phosphorothioate.

<400> SEQUENCE: 66
tgctgggggg aattga                                                      16

<210> SEQ ID NO 67
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine wherein phosphate of T
      is modified as phosphorothioate.
<220> FEATURE:
<221> NAME/KEY: misc_feature
<222> LOCATION: (4)..(4)
<223> OTHER INFORMATION: T represents a thymidine wherein phosphate of T
      is modified as phosphorothioate.
<220> FEATURE:
<221> NAME/KEY: misc_feature
<222> LOCATION: (5)..(10)
<223> OTHER INFORMATION: G represents a 2'OMe guanosine.
<220> FEATURE:
<221> NAME/KEY: misc_feature
<222> LOCATION: (11)..(11)
<223> OTHER INFORMATION: A represents a adenosine of locked nucleic acid
      wherein phosphate of A is modified as phosphorothioate.
<220> FEATURE:
<221> NAME/KEY: misc_feature
<222> LOCATION: (12)..(12)
<223> OTHER INFORMATION: A represents a adenosine of locked nucleic
      acid.
<220> FEATURE:
<221> NAME/KEY: misc_feature
```

```
<222> LOCATION: (13)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 67
tgctgggggg aattga                                                    16

<210> SEQ ID NO 68
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (5)..(10)
<223> OTHER INFORMATION: G represents a 2'OMe guanosine.
<220> FEATURE:
<221> NAME/KEY: misc_feature
<222> LOCATION: (11)..(11)
<223> OTHER INFORMATION: A represents a adenosine wherein phosphate of A
      is modified as phosphorothioate.
<220> FEATURE:
<221> NAME/KEY: misc_feature
<222> LOCATION: (16)..(16)
<223> OTHER INFORMATION: A represents a adenosine wherein phosphate of A
      is modified as phosphorothioate.

<400> SEQUENCE: 68
tgctgggggg aattga                                                    16

<210> SEQ ID NO 69
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
```

```
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (11)..(12)
<223> OTHER INFORMATION: A represents a 2'OMe adenosine wherein
      phosphate of A is modified as phosphorothioate.
<220> FEATURE:
<221> NAME/KEY: misc_feature
<222> LOCATION: (13)..(14)
<223> OTHER INFORMATION: T represents a 2'OMe thymidine.
<220> FEATURE:
<221> NAME/KEY: misc_feature
<222> LOCATION: (15)..(15)
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a 2'OMe adenosine wherein
      phosphate of A is modified as phosphorothioate.

<400> SEQUENCE: 69
tgctgggggg aattga                                                     16

<210> SEQ ID NO 70
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: G represents a guanosine of locked nucleic acid
      wherein phosphate of G is modified as phosphorothioate.
<220> FEATURE:
<221> NAME/KEY: misc_feature
<222> LOCATION: (6)..(9)
<223> OTHER INFORMATION: G represents a guanosine of locked nucleic
      acid.
<220> FEATURE:
<221> NAME/KEY: misc_feature
<222> LOCATION: (10)..(10)
<223> OTHER INFORMATION: G represents a guanosine of locked nucleic acid
      wherein phosphate of G is modified as phosphorothioate.

<400> SEQUENCE: 70
tgctgggggg aattga                                                     16

<210> SEQ ID NO 71
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: u represents a 2'OMe uridine wherein phosphate
      of u is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
```

```
<223> OTHER INFORMATION: C represents a 2'OMe cytidine.
<220> FEATURE:
<221> NAME/KEY: misc_feature
<222> LOCATION: (4)..(4)
<223> OTHER INFORMATION: u represents a 2'OMe uridine.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(12)
<223> OTHER INFORMATION: A represents a 2'OMe adenosine.
<220> FEATURE:
<221> NAME/KEY: misc_feature
<222> LOCATION: (14)..(14)
<223> OTHER INFORMATION: u represents a 2'OMe uridine.
<220> FEATURE:
<221> NAME/KEY: misc_feature
<222> LOCATION: (15)..(15)
<223> OTHER INFORMATION: G represents a 2'OMe guanosine.
<220> FEATURE:
<221> NAME/KEY: misc_feature
<222> LOCATION: (16)..(16)
<223> OTHER INFORMATION: A represents a 2'OMe adenosine wherein
      phosphate of A is modified as phosphorothioate.

<400> SEQUENCE: 71 ugcuggggggg aauuga                                                    16

<210> SEQ ID NO 72
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: u represents a uridine wherein phosphate of u
      is modified as phosphorothioate.
<220> FEATURE:
<221> NAME/KEY: misc_feature
<222> LOCATION: (7)..(8)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 72 ugcuggggggg aauuga                                                    16

<210> SEQ ID NO 73
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: u represents a uridine of locked nucleic acid
      wherein phosphate of u is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a cytidine of locked nucleic acid.
```

<220> FEATURE:
<221> NAME/KEY: misc_feature
<222> LOCATION: (4)..(4)
<223> OTHER INFORMATION: u represents a 2'OMe uridine.
<220> FEATURE:
<221> NAME/KEY: misc_feature
<222> LOCATION: (5)..(5)
<223> OTHER INFORMATION: G represents a guanosine of locked nucleic acid.
<220> FEATURE:
<221> NAME/KEY: misc_feature
<222> LOCATION: (6)..(6)
<223> OTHER INFORMATION: G represents a 2'OMe guanosine.
<220> FEATURE:
<221> NAME/KEY: misc_feature
<222> LOCATION: (7)..(7)
<223> OTHER INFORMATION: G represents a guanosine of locked nucleic acid.
<220> FEATURE:
<221> NAME/KEY: misc_feature
<222> LOCATION: (8)..(8)
<223> OTHER INFORMATION: G represents a 2'OMe guanosine.
<220> FEATURE:
<221> NAME/KEY: misc_feature
<222> LOCATION: (9)..(9)
<223> OTHER INFORMATION: G represents a guanosine of locked nucleic acid.
<220> FEATURE:
<221> NAME/KEY: misc_feature
<222> LOCATION: (10)..(10)
<223> OTHER INFORMATION: G represents a 2'OMe guanosine.
<220> FEATURE:
<221> NAME/KEY: misc_feature
<222> LOCATION: (11)..(11)
<223> OTHER INFORMATION: A represents a adenosine of locked nucleic acid.
<220> FEATURE:
<221> NAME/KEY: misc_feature
<222> LOCATION: (12)..(12)
<223> OTHER INFORMATION: A represents a 2'OMe adenosine.
<220> FEATURE:
<221> NAME/KEY: misc_feature
<222> LOCATION: (13)..(13)
<223> OTHER INFORMATION: u represents a uridine of locked nucleic acid.
<220> FEATURE:
<221> NAME/KEY: misc_feature
<222> LOCATION: (14)..(14)
<223> OTHER INFORMATION: u represents a 2'OMe uridine.
<220> FEATURE:
<221> NAME/KEY: misc_feature
<222> LOCATION: (15)..(15)
<223> OTHER INFORMATION: G represents a guanosine of locked nucleic acid.
<220> FEATURE:
<221> NAME/KEY: misc_feature
<222> LOCATION: (16)..(16)
<223> OTHER INFORMATION: A represents a adenosine of locked nucleic acid wherein phosphate of A is modified as phosphorothioate.

<400> SEQUENCE: 73
ugcugggggg aauuga        16

<210> SEQ ID NO 74
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: u represents a uridine of locked nucleic acid wherein phosphate of u is modified as phosphorothioate.
<220> FEATURE:
<221> NAME/KEY: misc_feature
<222> LOCATION: (2)..(2)
<223> OTHER INFORMATION: G represents a guanosine of locked nucleic

```
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: u represents a uridine of locked nucleic acid.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(12)
<223> OTHER INFORMATION: A represents a adenosine of locked nucleic
      acid.
<220> FEATURE:
<221> NAME/KEY: misc_feature
<222> LOCATION: (13)..(14)
<223> OTHER INFORMATION: u represents a uridine of locked nucleic acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 74
ugcugggggg aauuga                                                    16

<210> SEQ ID NO 75
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: u represents a 2'OMe uridine wherein phosphate
      of u is modified as phosphorothioate.
<220> FEATURE:
<221> NAME/KEY: misc_feature
<222> LOCATION: (2)..(2)
<223> OTHER INFORMATION: G represents a 2'OMe guanosine.
<220> FEATURE:
<221> NAME/KEY: misc_feature
<222> LOCATION: (3)..(3)
<223> OTHER INFORMATION: C represents a 2'OMe cytidine.
<220> FEATURE:
<221> NAME/KEY: misc_feature
<222> LOCATION: (4)..(4)
<223> OTHER INFORMATION: u represents a 2'OMe uridine wherein phosphate
      of u is modified as phosphorothioate.
<220> FEATURE:
<221> NAME/KEY: misc_feature
<222> LOCATION: (5)..(10)
<223> OTHER INFORMATION: G represents a guanosine of locked nucleic
      acid.
<220> FEATURE:
<221> NAME/KEY: misc_feature
<222> LOCATION: (11)..(11)
<223> OTHER INFORMATION: A represents a adenosine wherein phosphate of A
      is modified as phosphorothioate.
<220> FEATURE:
<221> NAME/KEY: misc_feature
<222> LOCATION: (16)..(16)
<223> OTHER INFORMATION: A represents a adenosine wherein phosphate of A
      is modified as phosphorothioate.
```

<400> SEQUENCE: 75 ugcuggggggg aauuga                                                    16

<210> SEQ ID NO 76
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid
      wherein phosphate of C is modified as phosphorothioate.
<220> FEATURE:
<221> NAME/KEY: misc_feature
<222> LOCATION: (14)..(14)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 76 tgctggggggg aattga                                                    16

<210> SEQ ID NO 77
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (2)..(2)
<223> OTHER INFORMATION: G represents a guanosine of locked nucleic
      acid.
<220> FEATURE:
<221> NAME/KEY: misc_feature
<222> LOCATION: (3)..(3)
<223> OTHER INFORMATION: C represents a cytidine of locked nucleic acid.
<220> FEATURE:
<221> NAME/KEY: misc_feature
<222> LOCATION: (4)..(4)
<223> OTHER INFORMATION: T represents a thymidine of locked nucleic acid
      wherein phosphate of T is modified as phosphorothioate.
<220> FEATURE:
<221> NAME/KEY: misc_feature
<222> LOCATION: (13)..(13)
<223> OTHER INFORMATION: T represents a thymidine of locked nucleic acid
      wherein phosphate of T is modified as phosphorothioate.
<220> FEATURE:
<221> NAME/KEY: misc_feature

```
<222> LOCATION: (14)..(14)
<223> OTHER INFORMATION: T represents a thymidine of locked nucleic
      acid.
<220> FEATURE:
<221> NAME/KEY: misc_feature
<222> LOCATION: (15)..(15)
<223> OTHER INFORMATION: G represents a guanosine of locked nucleic
      acid.
<220> FEATURE:
<221> NAME/KEY: misc_feature
<222> LOCATION: (16)..(16)
<223> OTHER INFORMATION: A represents a adenosine of locked nucleic acid
      wherein phosphate of A is modified as phosphorothioate.

<400> SEQUENCE: 77
tgctgggggg aattga                                                          16
```